US011664099B1

(12) United States Patent
Jain et al.

(10) Patent No.: US 11,664,099 B1
(45) Date of Patent: May 30, 2023

(54) DECENTRALIZED DATA COLLECTION FOR CLINICAL TRIALS

(71) Applicant: VigNet Incorporated, Fairfax, VA (US)

(72) Inventors: Praduman Jain, Fairfax, VA (US); Josh Schilling, Salem, OR (US); Dave Klein, Oakton, VA (US)

(73) Assignee: VigNet Incorporated, Fairfax, VA (US)

( * ) Notice: Subject to any disclaimer, the term of this patent is extended or adjusted under 35 U.S.C. 154(b) by 0 days.

(21) Appl. No.: 17/579,180

(22) Filed: Jan. 19, 2022

(51) Int. Cl.
*G16H 10/60* (2018.01)
*G16H 50/20* (2018.01)
*G16H 50/70* (2018.01)
*G16H 40/67* (2018.01)

(52) U.S. Cl.
CPC ............. *G16H 10/60* (2018.01); *G16H 40/67* (2018.01); *G16H 50/20* (2018.01); *G16H 50/70* (2018.01)

(58) Field of Classification Search
CPC ........ G16H 10/60; G16H 40/67; G16H 50/70; G16H 50/20
See application file for complete search history.

(56) References Cited

U.S. PATENT DOCUMENTS

| | | | |
|---|---|---|---|
| 10,231,077 B2 | 3/2019 | Raduchel et al. | |
| 10,366,204 B2 | 7/2019 | Tanner, Jr. et al. | |
| 10,726,098 B2 | 7/2020 | Brama | |
| 10,789,373 B2 | 9/2020 | Reid et al. | |
| 11,006,920 B2 | 5/2021 | Shah | |
| 11,227,675 B2 | 1/2022 | Bulleit et al. | |
| 11,244,059 B2 | 2/2022 | Yoon et al. | |
| 2004/0123109 A1 | 6/2004 | Choi | |
| 2011/0113050 A1 | 5/2011 | Youn et al. | |
| 2013/0227303 A1 | 8/2013 | Kadatch et al. | |
| 2014/0068270 A1 | 3/2014 | Shenoy | |
| 2015/0154418 A1 | 6/2015 | Redberg | |

(Continued)

OTHER PUBLICATIONS

Banerjee et al., "A Blockchain Future for Internet of Things Security: A Position Paper," Digital Communications and Networks, Aug. 2018, 4(3): 149-160.

(Continued)

*Primary Examiner* — Michael Tomaszewski
*Assistant Examiner* — Mohmad Muqueeth
(74) *Attorney, Agent, or Firm* — Fish & Richardson P.C.

(57) ABSTRACT

Methods, systems, and apparatus, including computer-readable media encoded with computer program instructions, for customized monitoring by remote devices. In some implementations, a system provides access to an application to a user through a device. The system receives an identifier for a secured data storage area of the user. Before receiving authorization to access the data in the data storage area, the system uses the identifier to obtain metadata indicating data classifications for the data stored in the data storage area, the metadata being obtained from a server system over a communication network. Based on the metadata, the system generates a second set of types of data to collect from the user. The system customizes interaction of the application with the user based on the set of second set of types of data, which is customized for the user based on the data classifications indicated by the metadata.

27 Claims, 18 Drawing Sheets

(56) References Cited

U.S. PATENT DOCUMENTS

| | | | |
|---|---|---|---|
| 2016/0134599 A1 | 5/2016 | Ross et al. | |
| 2017/0039324 A1 | 2/2017 | Francois et al. | |
| 2017/0185622 A1 | 6/2017 | Prahlad et al. | |
| 2018/0060496 A1* | 3/2018 | Bulleit | G16H 40/63 |
| 2018/0350451 A1 | 12/2018 | Ohnemus et al. | |
| 2019/0027237 A1 | 1/2019 | McFarlane | |
| 2019/0172566 A1 | 6/2019 | Schulman et al. | |
| 2019/0205563 A1 | 7/2019 | Gonzales, Jr. | |
| 2019/0243944 A1 | 8/2019 | Jain et al. | |
| 2019/0327239 A1 | 10/2019 | Ferguson | |
| 2019/0334884 A1 | 10/2019 | Ross et al. | |
| 2020/0242557 A1 | 7/2020 | Carey et al. | |
| 2020/0394334 A1* | 12/2020 | Bulut | G06F 21/6254 |

OTHER PUBLICATIONS

Bodin et al., "Evaluating Information Security Investments Using the Analytic Hierarchy Process," Communications of the ACM, Feb. 2005, 48(2):78-83.

Builtin.com [online], "35 Blockchain Applications and Real-World Use Cases Disrupting the Status Quo," Aug. 18, 2021, retrieved on Mar. 21, 2022, retrieved from URL<httpsL//builtin.com/blockchain/blockchain-applications>, 31 pages.

Cheng et al., "Healthcare Services Across China—On Implementing An Extensible Universally Unique Patient Identifier System," Journal of Healthcare Management, Nov. 7, 2017, 11(3):210-216.

Coindesk.com [online], "What Is A Dapp? Decentralized Apps Explained," Jan. 12, 2022, retrieved on Mar. 21, 2022, retrieved from URL<https://www.coindesk.com/learn/what-is-a-dapp-decentralized-apps-explained/>, 5 pages.

Computerworld.com [online], "10 Top Distributed Apps (dApps) for Blockchain," Dec. 30, 2019, retrieved on Mar. 21, 2022, retrieved from URL<https://www.computerworld.com/article/3510457/10-top-distributed-apps-dapps-for-blockchain.html>, 8 pages.

Cyran et al., "Blockchain as a Foundation for Sharing Healthcare Data," Blockchain in Healthcare Today, Mar. 23, 2018, 6 pages.

Dagher et al., "Ancile: Privacy-Preserving Framework for Access Control and Interoperability of Electronic Health Records Using Blockchain Technology," Sustainable Cities and Society, May 2018, 39:283-297.

dhaj7-cepo.com [online], "Blockchain Potential in Healthcare", Aug. 22, 2019, retrieved on Mar. 21, 2022, retrieved from URL<https://www.dhaj7-cepo.com/sites/default/files/S06_Presentation_2019AUGCCSS_Boodoo.pdf>, 61 pages.

Dubovitskaya et al., "Secure and Trustable Electronic Medical Records Sharing using Blockchain," Presented at AMIA Annual Symposium Proceedings, Washington, DC, Nov. 6-8, 2017, pp. 650-659.

Ekblaw et al., "A Case Study for Blockchain in Healthcare: "MedRec" Prototype for Electronic Health Records and Medical Research Data", IEEE Proceedings Open Big Data Conference, Aug. 2016, 13:1-13.

Fan et al., "Blockchain-based Efficient Privacy Preserving and Data Sharing Scheme of Content-Centric Network in 5G", IET Communications, Feb. 28, 2018, 12(5):527-532.

Fiercehealthcare.com [online], "Blockchain in Healthcare: 3 Promising Use Cases in A Sear of Skepticism," Aug. 22, 2018, retrieved on Mar. 21, 2022, retrieved from URL<https://www.fiercehealthcare.com/tech/blockchain-healthcare-3-promising-use-cases-and-some-not-so-promising-ones>, 7 pages.

Forrest et al., "Evidence-Based Decision Making in Action: Part 1—Finding the Best Clinical Evidence," The Journal of Contemporary Dental Pratice, Aug. 15, 2002, 1-21.

Gordan et al., "Blockchain Technology for Healthcare: Facilitating the Transition to Patient-Driven Interoperability," Computational and Structural Biotechnology Journal, Jun. 30, 2018, 16:224-230.

Grover et al., "Technology Enabled Health—Insights from Twitter Analytics with a Socio-Technicaly Perspective," International Journal of Information Management, Dec. 2018, 43:85-97.

Guidelines for performing systematic literature reviews in software engineering, EBSE Technical Report, Jul. 9, 2007, 65 pages.

Guo et al., "Secure Attribute-Based Signature Scheme with Multiple Authorities for Blockchain in Electronic Health Records Systems," IEEE Access, Feb. 2, 2018, 6:11676-11686.

Hashemi et al., "World of Empowerment IoT Users," Presented at 1st IEEE International Conference on Internet-of-Things Design and Implementation, IoTDI 2016, Berlin, Germany, Apr. 4-8, 2016, 12 pages.

Hill, "Book Review: M. Petticrew and H. Roberts. Systematic reviews in the social sciences: A practical guide. Oxford: Blackwell 2006. 352 pp. ISBN 1 4051 2110 6. £29.99," Counselling and Psychotherapy Research, Dec. 2006, 6(4):304-305.

IBM.com [online], "What Are Smart Contracts on Blockchain", Jan. 18, 2022, retrieved on Mar. 21, 2022, retrieved from URL<https://web.archive.org/web/20220118212540/https:/www.IBM.com/topics/smart-contracts>, 18 pages.

Ichikawa et al., "Tamper-Resistant Mobile Health Using Blockchain Technology," JMIR Mhealth Uhealth, Jul. 2017, 5(7):e111.

Jiang et al., "Blochie: A Blockchain-based Platform for Healthcare Information Exchange," Presented at 2018 IEEE International Conference on Smart Computing (Smartcomp), Taormina, Italy, Jun. 18-20, 2018, pp. 49-56.

Karafiloski, "Blockchain Solutions for Big Data Challenges", Presented at IEEE Eurocon, Ohrid, Macedonia, Jul. 6-8, 2017, 6 pages.

Keranews.com [online], "how Bitcoin Technology Could Securely Share Medical Records Among Your Doctors," Mar. 8, 2017, retrieved on Mar. 21, 2022, retrieved from URL<https://www.keranews.org/health-science-tech/2017-03-08/how-bitcoin-technology-could-securely-share-medical-records-among-your-doctors>, 9 pages.

Kleinaki et al., "A Blockchain-Based Notarization Service for Biomedical Knowledge Retrieval," Computational and Structural Biotechnology Journal, Aug. 17, 2018, 16:288-297.

Kshetri, "Blockchain's Roles in Strengthening Cybersecurity and Protecting Privacy," Telecommunications Policy, Nov. 2017, 41(10): 1027-1038.

Kuo et al., "Blockchain Distributed Ledger Technologies for Biomedical and Health Care Applications," Journal of Informatics in Health and Biomedicine, Sep. 2017, 24(6):1211-1220.

Lemieux, "A Typology of Blockchain Recordkeeping Solutions and Some Reflections on Their Implications for the Future of Archival Preservation," Presented at IEEE International Conference on Big Data, Boston, MA, USA, Dec. 11-14, 2017, pp. 2271-2278.

Linn et al., "Blockchain for Health Data and Its Potential Use in Health IT and Health Care Related Research," ONC/NIST Use of Blockchain for Healthcare and Research Workshop, 2016, 10 pages.

Liu et al., "Advanced Block-Chain Architecture for e-Health Systems," 2017 IEEE 19th International Conference on e-Health Networking, Applications and Services, Oct. 2017, 6 pages.

Mamoshina et al., "Converging Blockchain and Next-Generation Artificial Intelligence Technologies to Decentralize and Accelerate Biomedical Research and Healthcare," Oncotarget, Jan. 2018, 9(5):5665-5690.

Mannaro et al., "A Blockchain Approach Applied to a Teledermatoloy Platform in the Sardinian Region (Italy)," Information, Feb. 23, 2018, 9(2):44.

Mayer et al., "Electronic Health Records In A Blockchain: A Systematic Review," Health Informatics Journal, 2020, 26(2):1273-1288.

NCBI.nlm.nih.gov [online], "Guiding Principles for Sharing Clinical Trial Data," Dec. 10, 2015, retrieved on Mar. 21, 2022, retrieved from URL<https://www.ncbi.nlm.nih.gov/books/NBK285999/>, 14 pages.

NCBI.nlm.nih.gov [online], "The Benefits of Data Sharing", Mar. 29, 2013, retrieved on Mar. 21, 2022, retrieved from URL<https://www.ncbi.nlm.nih.gov/books/NBK137823/>, 5 pages.

Nichol et al., "Co-Creation of Trust for Healthcare: The Cryptocitizen Framework for Interoperability with Blockchain," Research Proposal, Jul. 2016, 10 pages.

Niranjanamurthy et al., "Analysis of Blockchain Technology: Pros, Cons and SWOT," Cluster Computing, Mar. 19, 2018, 20:1-15.

(56) References Cited

OTHER PUBLICATIONS

Patel et al., "A Framework for Secure and Decentralized Sharing of Medical Imaging Data via Blockchain Consensus," Health Informatics Journal, Dec. 2019, 25(4):1398-1411.

Pharmaphorum.com [online], "How Blockchain Can Revolutionise Medical Records and Save Lives," Sep. 6, 2021, retrieved on Mar. 21, 2022, retrieved from URL<https://pharmaphorum.com/digital/blockchain-healthcare-electronic-medical-records/>, 4 pages.

Priisalu et al., "Personal Control of Privacy and Data: Estonian Experience," Health and Technology, Jun. 15, 2017, 7:441-451.

Rabah, "Challenges & Opportunities for Blockchain Powered Healthcare ASystems: A review," Mara Res. J. Med. Health Sci., 2017, 1(1):45-52.

Rabah, "Opportunities and Challenges of Blockchain Technologies in Health Care," OECD Blockchain Policy Series, Dec. 2020, 12 pages.

Ribitzky et al., "Pragmatic, Interdisciplinary Perspectives on Blockchain and Distributed Ledger Technology: Paving the Future for Healthcare," Blockchain in Healthcare Today, Mar. 23, 2018, 15 pages.

Roehrs et al., "OmniPHR: A Distributed Architecture Model to Integrate Personal Health Records," Journal of Biomedical Informatics, Jul. 2017, 71:70-81.

Roman-Belmonte et al., "How Blockchain Technology Can Change Medicine," Postgraduate Medicine, May 2018, 130(4):420-427.

Ross, "Clinical Research Data Sharing: What An Open Science World Means for Researched Involved in Evidence Synthesis," Systematic Reviews, Sep. 20, 2016, 5:159.

Shae et al., "On the Design of a Blockchain Platform for Clinical Trial and Precision Medicine," Presented at IEEE 37th International Conference on Distributed Computing Systems, Atlanta, GA, USA, Jun. 5-8, 2017, 9 pages.

Smith et al., "Blockchain for Digital Crime Prevention: The Case of the Health Informatics," 23rd Americas Conference on Information Systems, Aug. 2017, 10 pages.

Thomason J. "Blockchain: An Accelerator for Women and Children's Health?" Glob Heal J., Jun. 2017; 1(1): 3-10.

Wang et al., "Secure Cloud Based HER System Using Attibute-Based Cryptosystem and Blockchain," Journal of Medical Systems, Jul. 2018, 42(8):1-9.

Wikipedia.org [online], "Decentralized Application," Jan. 17, 2022, retrieved on Mar. 21, 2022, retrieved from URL<https://web.archive.org/web/20220117113529/https:/en.wikipedia.org/wiki/Decentralized_application>, 7 pages.

Xia et al., "MeDShare: Trust-Less Medical Data Sharing Among Cloud Service Providers via Blockchain," IEEE Access, Jul. 24, 2017, 5:14757-14767.

Yang et al., "A Blockchain-based Approach to the Secure Sharing of Healthcare Data," Proceedings of the Norwegian Information Security Conference, 2017, pp. 100-111.

Yue et al., "Healthcare Data Gateways: Found Healthcare Intelligence on Blockchain with Novel Privacy Risk Control," Mobile and Wireless Health, Aug. 26, 2016, 40(218):1-8.

Zhang et al., "FHIRChain: Applying Blockchain to Securely and Scalably Share Clinical Data," Computational and Structural Biotechnology Journal, Jul. 2018, 16:267-278.

U.S. Appl. No. 17/578,917, filed Jan. 19, 2022, 108 pages.

\* cited by examiner

| Data | Data Classifier | Value Type | Coded Value |
|---|---|---|---|
| Activity (e.g. Steps) | ACTIVITY_MEASUREMENTS | GUID (128 bit) | 81428087-c211-4275-9eaa-0e0ef9ebfe87 |
| Sleep (e.g. time asleep) | SLEEP_MEASUREMENTS | GUID | 30d0ef62-89f4-41ef-907f-305d60bf534e |
| Fertility (e.g. ovulation) | FERTILITY_TRACKING | GUID | 1b682c81-760d-4b54-992c-e18168a3ee55 |
| Food (e.g. meals, sugar) | FOOD | GUID | 260ffb5c-3444-448e-885c-2296b63f229a |
| Pancreatic (e.g. Glucose) | PANCREATIC_MEASUREMENTS | GUID | 8ea525d9-46fc-41b9-a5c3-bf46b8642714 |
| Cardiovascular (e.g. heart rate) | CARDIOVASCULAR_MEASUREMENTS | GUID | 8ea525d9-46fc-41b9-a5c3-bf46b8642714 |
| Respiratory (e.g. Oximetry) | RESPIRATORY_MEASUREMENTS | GUID | 8ea525d9-46fc-41b9-a5c3-bf46b8642714 |
| Temp (e.g. body, skin, basal) | TEMP_MEASUREMENTS | GUID | 8ea525d9-46fc-41b9-a5c3-bf46b8642714 |
| Physical (e.g. weight, height, BMI) | PHYSICAL_MEASUREMENTS | GUID | 8ea525d9-46fc-41b9-a5c3-bf46b8642714 |
| Environment (e.g. air quality, dust) | ENVIRONMENT_MEASUREMENTS | GUID | 8ea525d9-46fc-41b9-a5c3-bf46b8642714 |
| Genomics (e.g. attributes) | GENOMICS | Hex - 160 bits (20 bytes) | 5e e6 d7 d1 d2 a7 76 5a a8 87 8e 9a 45 5b 7b e4 4b 7d 25 65 |
| EHR (e.g. encounters, surgeries, medication) | EHR_DATA | Hex - 160 bits (20 bytes) | 1d 12 e5 fb 5d 6f e8 85 8c a4 41 37 5c 3f f8 6a f6 2b 4d a1 |
| | ... | | |

FIG. 6

DECENTRALIZED DATA COLLECTION FOR CLINICAL TRIALS

BACKGROUND

The number of Internet-connected devices continues to grow, and so does the volume and variety of data generated. Nevertheless, in many cases users often do not have the tools to manage their data and control its use. Even as the number of devices proliferate and their capabilities expand, many data sets remain in separate proprietary systems where users cannot view the data collected about them or control how it is used.

As an example, large amounts of health data are generated in the medical field, but much of it remains inaccessible or unknown to the individuals that the data describes. While regulations may help keep health data private, too often the patients that the data is supposed to help do not have a platform to view or otherwise use their health data, much less control how or when their health data is shared. Frequently, patients are asked to fill out forms (e.g., to provide medical history, vaccination status, allergies and medication sensitivities, etc.) again and again, even though the patient has previously provided the information to the same healthcare provider or a different healthcare provider. If a user would like to share health data electronically, such as with a software application, a web page, a clinical trial, or even from one doctor to another, there is often no mechanism to do so.

The absence of effective and secure ways to share health data limits patients' access to their own health data and vastly underutilizes the rich collection of health data that is generated. The quality of medical care provided is also reduced by the inability of patients and doctors to determine what health data has been collected and access to that data. For example, treatment decisions are often made without the context of all of the health data available for a patient. In addition, medical staff often perform unnecessary duplicative tests and procedures, not realizing that testing has already been performed. Progress in health research is also limited when users cannot share data from their private clinical data and their data from studies they have previously participated in, leading each study to separately collect data that may already be collected for study participants.

SUMMARY

In some implementations, a computer system provides a data storage and data sharing platform that enhances data re-use and interoperability among a distributed ecosystem of applications. A computer system can provide the capability for individuals to have separately secured, access controlled data areas. The computer system can also provide application programming interfaces (APIs) that enable access to the various data storage areas, conditioned on authorization and permission levels granted by the users. Various different parties (e.g., third parties with respect to the computer system and the individual users) can all develop and contribute applications to the ecosystem, whether as web-based applications, native applications for computing devices, or in other forms.

In the system, individual users can retain personal ownership and control of their data, with the ability to set access permissions that are enforced by the system. The system can provide security and privacy features such as encryption and personal ownership and access control. The system gives users the tools to grant authorization to an application, as well as revoke access. The user's identity can also be concealed using deidentified identifiers for the data areas.

While preserving users' privacy and control of their data, the system enables users to authorize different applications and parties to selectively access some or all of the data in the data storage areas. The system can store data in standardized formats, for example, according to a predetermined taxonomy, or can include code to translate between data formats. For example, the system can include metadata in the data areas to designate the meaning and format used for different records, and also include mapping tables that the system can use to translate from the stored format to other formats needed. The system also and make data from the data storage areas available through a set of public APIs, to encourage interoperability and the use of data for any applications that the user authorizes to gain access.

The techniques can be applied to improve many aspects of healthcare and health research. For example, the data storage area for an individual can act as a digital wallet for the user's health data. Discrete portions of a person's health record are stored in cloud-computing-based storage, in a unique location (e.g., with a unique identifier) and secure format. The system also provides access control, configurable by the user, for specifying how and when the underlying health data can be accessed. The system can define data classifications (e.g., data types or categories), so that the system can track, store, and control access data at a fine-grained level. For example, the system can provide access to only some types of data in a data storage area and not others.

The system can also apply automated stored procedures, analogous to smart contracts in blockchains, for a user's health data. For example, a user or application can set alerts to be provided when certain actions affecting a data storage area occur or fail to occur (e.g., when a new record is added or is fails to be added). Similarly, the procedures can perform more complex workflows based on the values in the records, such as to detect when a blood pressure measurement exceeds a threshold value, and in response to trigger a particular application and provide the value to that application.

In many areas of health care and health research, large amount of duplicative data collection is performed. For example, patients often need to fill out forms to provide the same information (e.g., medical history, allergies, etc.) for every doctor they visit. Similarly, research studies often begin with little to no information about participants, and create new baseline data, history data, and so on for each participant. However, the present system provides techniques for users to maintain their data in a manner that is secure and private, but also easily sharable by the individual when the individual authorizes it. As a result, among other benefits, when a user provides access to a data storage area with his health data, researchers don't have to collect data already available and participants don't have to repeatedly share and repeatedly fill out forms.

For example, a computer system can storing health data for an individual in cloud-based data storage. The health data for the individual can be stored on one or more logical data storage areas, each with a unique identifier that distinguishes it from all others. In some cases, the user's health data is divided among multiple data storage areas that can be separate and independent, but may optionally be linked or connected if the user authorizes it. The data storage areas can be de-identified such that they are not associated with an identity of the individual. Different data storage areas can be encrypted using different encryption keys to provide security. The data storage areas each have corresponding unique identifiers, which generally are not linked to the individual's identity. The computer system provides the ability for the data storage areas to be separately accessible by third-party applications through an API. The data areas are selectively sharable, with the ability for users to set customized permissions for each instance of sharing. As a result, ownership and privacy of the data area are maintained by the individual. In some implementations, users or applications can set stored procedures smart contracts for the data areas. For example, data identifying or defining a set of rules or a workflow triggered by certain conditions can be stored in or associated with a data storage area. The computer system can monitor when the conditions for triggering the workflow are met, and can automatically perform the actions of the workflow in response.

The computer system provides access control to enable the individual to authorize selective access to the data areas. The system can generate tokens that grant access by a specific application to a specific data area. These tokens can be non-transferrable because the system checks that the application identifier, an application certificate (or other authentication data), and the data area identifier all match as indicated by a provided access token before the system permits access. In addition, an incorrect token will fail to include the cryptography elements needed to access the encrypted area of the data storage. The tokens can have embedded limitations on: the type of access to the data area (e.g., limits to permissions such as read, create, modify, etc.); the duration of access (e.g., set expiration times); the number of accesses permitted; scope of access (e.g., the data types that can be accessed, or sources of data from which data can be accessed, etc.). In some implementations, the system manages renewal or refreshing of tokens. The tokens or the data areas can indicate how often the token needs to be refreshed. The system can support a token auto-renewal protocol, so that the access token renews regularly (e.g., each week, each month, each year) until the participant switches it off. The tokens can be for a specific data type (e.g., access to blood pressure data for a data storage area may require a different token than one for heart rate data). Users can set some data (e.g., physical activity data) to be continuously shared, but can set other more sensitive data to be shared only once until requested again and authorized again by the user. For example, when an electronic health record (EHR) application is used, the system can allow it to write into an EHR record. However, another application (e.g., for data visualization, data sharing, etc.) may be restricted to only read the EHR data or read only a portion of it.

The computer system enables access to decentralized applications, including third-party applications that may be provided by or hosted by various different parties. The computer system can receive and respond to access requests that include access tokens, enforce token restrictions, perform the decryption and data transfer to applications subject to the token restrictions. The computer system can also aggregate data from different data areas through links between the data areas, to create a persistent logical data set without creating new storage copies the underlying data.

The computer system can perform various actions to manage data areas. These actions can include creating new data areas and assigning unique identifiers and issuing unique identifiers to third parties that create and store their own data areas. The system can enable multiple data storage systems and geographical locations, to allow interoperability across data lakes stored in different countries, to respect privacy and data security laws. The system can maintain mappings of data area identifiers or addresses to actual data storage in the cloud computing system. The computer system can also create and maintain a registry of trusted applications that meet a set of governance standards, and may provide an application gallery to users to select from among those applications and gain access. The system can also generate and store metadata for data areas based on contents of the data areas. This can include storing labels or classifications provided by applications that create the data, verifying or validating the accuracy of those labels, augmenting the labels with standardized labels (e.g., data classifications from a standardized taxonomy), or evaluating data after it is stored to classify the data. The computer system can also enforce data validity policies. For example, the system can use hashes, encryption, or version control to require data writes to be done so that each data storage area is a tamper-evident append-only ledger.

As discussed above and further below, the computer system provides an API that enables interoperability among a decentralized ecosystem of applications. The API can use a standardized taxonomy of data type classifications and defined request formats. The computer system can also abstract the boundaries of different data storage areas to provide automatic data aggregation across multiple data areas. For example, although a data set may be stored in many different data storage areas that reference each other in a chain or tree, the system can present the combined set of data to an application or viewer, doing the aggregation functions in the background, optionally not revealing the full structure of the data area relationships.

The system provides researcher tools that can enable researchers to view public metadata for data storage areas to understand a cohort candidate pool and select specific candidates. The system can aggregate data across data storage areas of multiple participants, and for multiple data areas of individual participants. The tools also enable researchers to share and aggregate data across different research studies, by providing authorization or links between the data storage areas for the different research studies. The tools can also de-duplicate or combine data records for the same individual.

In one general aspect, a method performed by one or more computers includes: storing, by the one or more computers, data for multiple individuals in one or more data storage devices, the data for each individual being stored in a different logical data storage area, wherein the data storage areas are respectively assigned unique identifiers and different data storage areas have contents encrypted using different encryption keys; storing, by the one or more computers, data indicating a set of predetermined data classifications; for each data storage area of at least some of the data storage areas: determining, by the one or more computers, data classifications for data stored in an encrypted form in the data storage area, the data classifications being determined from among the set of predetermined data classifications; and storing, by the one or more computers, data indicating the determined data classifications for the data storage area in metadata associated with the data storage area; and providing, by the one or more computers, an application programming interface (API) that enables multiple different applications to access the data storage areas over a communication network, wherein the one or more computers are configured to: provide access through the API to the data stored in an encrypted form in the data storage areas, wherein access to the data is conditioned on applications providing authorization tokens corresponding to the data storage areas accessed for which the data is accessed; and provide access through the API to the data classifications in the metadata corresponding to the respective data storage areas, wherein access to the data classifications is not conditioned on applications providing authorization tokens corresponding to the data storage areas for which the data classifiers are accessed.

In some implementations, the predetermined data classifications represent different types of data; determining the data classifications includes determining, for a particular data storage area, types of data present in the particular data storage area; and storing the data indicating the determined data classifications includes storing, for the particular data storage area, metadata that indicates the types of data determined to be present in the particular data storage area.

In some implementations, the predetermined data classifications represent predetermined aspects of physiology, behavior, or mental health; and the metadata that indicates the types of data determined to be present in the particular data storage area includes metadata that indicates the aspects of physiology, behavior, or mental described by the encrypted data in the particular data storage area.

In some implementations, the predetermined data classifications represent predetermined types of measurements of physiology, behavior, or mental health; and wherein the metadata that indicates the types of data determined to be present in the particular data storage area includes metadata that specifies types of measurements, from among the predetermined types of measurements, for which the encrypted data in the particular data storage area includes measurement values.

In some implementations, storing metadata that indicates the types of data determined to be present in the particular data storage area includes storing, in the metadata for the particular data storage area, identifiers for each of multiple types of data that are determined to be present in the encrypted data of the particular data storage area.

In some implementations, storing metadata that indicates the types of data determined to be present in the particular data storage area includes: for each of at least some of the predetermined data classifications, storing, in the metadata for the particular data storage area, a value that indicates whether the encrypted data of the particular data storage area includes information of the type represented by the predetermined data classification.

In some implementations, storing the data indicating the set of predetermined data classifications includes storing data indicating a hierarchy of categories that represent types of data at different levels of specificity; and storing metadata that indicates the types of data determined to be present in the particular data storage area includes storing, in the metadata for the particular data storage area, identifiers for elements in the hierarchy that describe types of data that are determined to be present in the encrypted data of the particular data storage area.

In some implementations, the predetermined data classifications represent different sources of data; determining the data classifications includes identifying, for a particular data storage area, one or more sources of the data in the particular data storage area; and storing the data indicating the determined data classifications includes storing, for the particular data storage area, metadata that indicates the identified one or more sources of the data in the particular data storage area.

In some implementations, the predetermined data classifications are a predetermined set of data quality classifications that represent different levels of quality of data; determining the data classifications includes determining, for a particular data storage area, a quality level classification for the data in the particular data storage area, the quality level classification being selected from among the predetermined set of data quality classifications; and storing the data indicating the determined data classifications includes storing, for the particular data storage area, metadata that indicates the data quality classification of the data in the particular data storage area.

In some implementations, the predetermined set of data quality classifications represent different levels of one or more of precision, accuracy, consistency, or completeness.

In some implementations, the method includes: storing, for a particular data storage area, a user-specified metadata access setting that governs access to metadata for the particular data storage area; receiving a request through the API for data indicating data classifications for data stored in a particular data storage area; determining that access to the data classifications for the particular data storage area is permitted based on the user-specified metadata access setting; and based on determining that access to the data classifications for the particular storage area is permitted, providing a response to the request that identifies one or more data classifications for contents of the particular data storage area.

In some implementations, the user-specified metadata access setting provides a limit to the types of metadata or level of precision of metadata that can be provided for the particular data storage area without a valid authorization token granting access to the particular data storage area; and the method includes generating the response based on the user-specified metadata access setting such that the response omits data classifications for one or more types of data in the particular data storage area or such that the response generalizes one or more data classifications based on the user-specified metadata access setting.

In some implementations, user-specified metadata access settings for a particular data storage area limit different applications to different levels of access to metadata for the particular data storage area; and in response to requests from different applications for metadata regarding the particular data storage area, providing different subsets of the metadata to the different applications based on the user-specified metadata access settings.

In some implementations, the method includes detecting, for a particular data storage area, a predetermined condition set as a trigger to refresh metadata for the particular data storage area; and in response to detecting the predetermined condition, updating a set of data classifications for contents of the particular data storage area.

In some implementations, the method includes: generating metadata for a particular data storage area by: decrypting contents of the particular data storage area; classifying the contents of the particular data storage area to select data classifications from the predetermined data classifications that are applicable for the contents of the particular data storage area; and storing metadata for the particular data storage area that indicates the selected data classifications.

In some implementations, the data stored for the individuals is health data that describes health conditions or health characteristics of the individuals; and at least some of the data storage areas are data storage areas storing health data generated for a health research study in which the individual is a participant. In some implementations, one or more data storage areas, for individuals or for a study as a whole, may be dedicated exclusively to storing data for a particular health research study.

In another general aspect, a method performed by one or more computers includes: providing, by the one or more computers, access to an application to a user through a device, wherein the application specifies a first set of types of data to collect from users of the application; receiving, by the one or more computers, an identifier for a secured data storage area of the user, the identifier being provided by the user to the application, wherein the data storage area is managed by a server system configured to (i) provide access to data in the data storage area in response to an access token for the data storage area and (ii) provide metadata indicating data classifications for data in the data storage area without requiring an access token for the data storage area; before receiving authorization to access the data in the data storage area, using, by the one or more computers, the identifier to obtain the metadata indicating data classifications for the data stored in the data storage area, the metadata being obtained from the server system over a communication network; generating, by the one or more computers, a second set of types of data to collect from the user of the application, the second set being customized for the user based on the data classifications indicated by the metadata for the data storage area indicated by the identifier provided by the user, wherein the second set of types of data includes a subset of the types of data in the first set and omits one or more types of data in the first set; and customizing, by the one or more computers, interaction of the application with the user based on the set of second set of types of data that is customized for the user based on the data classifications indicated by the metadata for the data storage area.

In some implementations, the method includes: determining multiple types of data that the application is configured to obtain from users of the application, wherein the determined types of data are the first set of types of data; and for each of the multiple types of data that the application is configured to obtain, determining whether the metadata indicates that data of that type of data is stored in the data storage area. Generating the second set of types of data includes: based on determining that the metadata indicates that data of a particular type is stored in the data storage area, generating the second set of types of data to omit the particular type of data; and wherein customizing interaction of the application with the user includes: based on the generated second set of data, customizing behavior of the application to (i) use one or more sensors or user interfaces to collect data from the user for each of the types of data in the second types of data, and (ii) obtain data for the particular type of data from the data storage area instead of collecting data for the particular type of data from the user.

In some implementations, the method includes: identifying, for the particular type of data, one or more criteria for data of the particular type of data to be used by the application, wherein the one or more criteria specify a time constraint or a constraint for a level of precision, a source of data, or amount of data needed; and determining, based on the metadata, that the one or more criteria is met for the data of the particular type in the data storage area. The particular type of data is omitted from the second set of types of data based on determining that the one or more criteria for the particular type of data is met.

In some implementations, the method includes: determining, based on the metadata for the data storage area, that the data storage area stores data of a particular type that is included in the first set of types of data; identifying a characteristic or condition that data of the particular type is required to meet to be used by the application; and determining, based on the metadata, that the data of the particular type in the data storage area does not have the characteristic or does not satisfy the condition. Generating the second set of types of data includes: based on determining that the data of the particular type in the data storage area does not have the characteristic or does not satisfy the condition, including the particular type of data in the second set of types of data such that the application initiates collection of data of the particular type for the user.

In some implementations, the method includes determining, based on the metadata for the data storage area, that the data storage area stores data of a particular type that is included in the first set of types of data. The metadata indicates data collection parameters used to generate the data of the particular type that is included in the first set of types of data. Generating the second set of types of data includes omitting the particular type of data from the second set of types of data based on determining that the data collection parameters used to generate the data of the particular type in the data storage area satisfy a set of predetermined criteria.

In some implementations, the application is configured to repeatedly obtain measurements for a particular type of data in the first set of types of data, wherein the particular type of data describes characteristics of the user or behavior of the user. The metadata for the data area indicates characteristics of a pattern of previous data collection actions performed to collect data of the particular type for the user that is stored in the data storage area. Generating the second set of types of data includes omitting the particular type of data from the second set of types of data based on determining that the pattern of previous data collection actions satisfies a set of predetermined criteria.

In some implementations, the application is configured to repeatedly obtain measurements for a particular type of data in the first set of types of data, wherein the particular type of data describes characteristics of the user or behavior of the user. The metadata for the data area indicates that the data storage area is designated to receive repeated future measurement results for the particular type. Generating the second set of types of data includes omitting the particular type of data from the second set of types of data based on determining that the metadata for the data area indicates that the data storage area is designated to receive repeated future measurement results for the particular type.

In some implementations, the application is an software application for a health research study, and wherein the first set of types of data are types of data that a study protocol for the health research study specifies to obtain from participants in the health research study as part of the health research study.

In some implementations, the first set of types of data and the second set of types of data each include multiple types of health data, including one or more types of physiological data for the user and one or more types of behavioral data for the user.

In some implementations, the application is configured to perform repeated interactions over time to monitor health of the user through (i) sensor measurements performed using sensors of one or more devices, and (ii) survey responses by the user to surveys presented by one or more devices.

In some implementations, customizing interaction of the application with the user based on the set of second set of types of data includes configuring the application to initiate collection of data for each of the types of data in the second set of data types.

In some implementations, customizing interaction of the application with the user based on the set of second set of types of data includes providing, for output on a user interface of the device of the user, a list indicating the types of data in the second set of types of data as items to be collected for the user.

In some implementations, the application is an application for a health research study, and the list is a list of types of health data to be collected in order for the user to enroll in the health research study or as part of the user participating in the health research study.

Various implementations allow infrastructure to provide access control and ensure privacy Infrastructure, with individuals having personal ownership over their data and the ability to set permissions for access to their data storage areas. In another general aspect, a method performed by one or more computers, includes: storing, by the one or more computers, health data for multiple individuals in one or more data storage devices, the health data for different individuals being stored in logical data storage areas, wherein the data storage areas are assigned unique identifiers and have contents encrypted; providing, by the one or more computers, an application programming interface (API) that enables multiple different applications to access the data storage areas over a communication network, wherein the one or more computers are configured to selectively provide access to the data storage areas based on authorization tokens that are each respectively configured to grant a specific application limited access to a specific data storage area; receiving, by the one or more computers, a request through the API for a particular application to access a particular data storage area, the request providing the identifier for the particular data storage area and an authorization token; determining, by the one or more computers, that the authorization token authorizes the particular application to access the particular data storage area; and in response to determining that the authorization token authorizes the particular application to access the particular data storage area, granting, by the one or more computers, access by the particular application to the particular data storage area, wherein the access by the particular application is limited according to one or more access limitations specified in the access token.

In some implementations, for at least a first individual of the multiple individuals, the health data for the first individual is divided among multiple separate logical data storage areas that have different unique identifiers and that respectively have their contents encrypted with different encryption keys.

In some implementations, the health data for the first individual comprises health data provided by different data sources; and the multiple separate logical data storage areas for the first individual include different data storage areas configured to respectively store health from the different data sources.

In some implementations, the data storage areas are data lakes configured to store structured and unstructured data.

In some implementations, the data storage areas are de-identified and are encrypted using different encryption keys.

In some implementations, the data storage areas are each implemented as append-only ledgers.

In some implementations, the request is a request to read data from the particular data storage area; and granting access comprises: identifying, by the one or more computers, a subset of the data in the particular data storage area that (i) is responsive to the request and (ii) the authorization token authorizes to be provided to the particular application; decrypting, by the one or more computers, the identified subset; and providing, by the one or more computers, the decrypted subset of the data in the particular data storage area to the particular application over the communication network.

In some implementations, the request is a request to write first data to the particular data storage area; and granting access comprises: receiving, by the one or more computers, the first data from the particular application over the communication network; encrypting, by the one or more computers, the first data using a key corresponding to the particular data area; and storing, by the one or more computers, the encrypted first data in the particular data area.

In another general aspect, a method performed by one or more computers includes: storing, by the one or more computers, health data for multiple individuals in one or more data storage devices, the health data for different individuals being stored in different de-identified logical data storage areas, wherein the data storage areas are assigned unique identifiers and have contents encrypted using different encryption keys, and wherein the data storage areas each have an encrypted portion storing health data in an encrypted form and metadata portion; generating, by the one or more computers, metadata for the data storage areas, wherein the metadata for each data storage area describes a type or source of health data stored in encrypted form in the data storage area without indicating values of the health data stored in the data storage area; and providing, by the one or more computers, an application programming interface (API) that enables multiple different applications to access the data storage areas over a communication network, wherein the API (i) provides access to the health data in the data storage areas with access control that conditions access on providing an authorization token corresponding to the data storage area; and (ii) provides access to at least portions of the metadata for the data storage areas that is not conditioned on providing an authorization token.

In another general aspect, a method of generating access tokens comprises: receiving, by one or more computers, a request to authorize an application to access a data storage area, the request comprising an application identifier for the application and a data storage area identifier for the data storage area; receiving, by the one or more computers, data indicating user approval to access the data storage area and an indication of authorized scope of access to the data storage area; based on the received data, determining, by the one or more computers, limitations on access to the data storage area; generating, by the one or more computers, a token that authorizes the application to access the data storage area, the token specifying limitations on access to the data storage area by the application and an expiration for the token; and providing, by the one or more computers, the token in response to the request.

In another general aspect, a method for creating or authorizing applications comprises: storing, by the one or more computers, a repository of components, including modules configured to use an API to access health data stored in different de-identified logical data storage areas, wherein the data storage areas are assigned unique identifiers and have contents encrypted using different encryption keys; assigning, by the one or more computers, a unique application identifier for a new decentralized application to access the health data through the de-identified logical data storage areas; providing, by the one or more computers, an interface to select functionality to include in a decentralized application; integrating, by the one or more computers, modules selected from the repository that correspond to the selected functionality with custom elements provided through the interface; verifying, by the one or more computers, that the new application satisfies one or more governance requirements; and registering, by the one or more computers, the new application to be accessed through a program gallery.

In some implementations, the system is configured to store data for participants in a health research studies in a separate data storage area for each participant. The system is configured to pool the contents of the separate data storage areas to provide researchers for the study a unified view and unified data set across all the participants (e.g., all the data storage areas). This is done while maintaining each individual participant's access to and control over his or her data collected in the study, subject to participant's already authorized use of that data in the study.

In another general aspect, a method of aggregating data for a health research study includes: identifying, by the one or more computers, a set of participants in a health research study; for each participant, obtaining (i) an identifier for a de-identified, secured data storage area for the participant for the health research study, and (ii) an authorization token indicating user authorization for the health research study to use the data storage area; collecting, by the one or more computers, health data from the respective participants during the health research study; storing, by the one or more computers, the health data collected for each participant in the data area corresponding to the participant using the authorization token and identifier obtained for the participant; and providing, by the one or more computers, a combined data set that aggregates the date from the respective secured data storage areas of the participants using the authorization tokens.

In some implementations, the system provides features that enable a research study to import existing health data from different participants or candidates for a research study. This can be done by receiving the data storage area identifiers and access tokens based on participant's agreements to share access to the data storage areas. The system then can pool the shared individual data storage areas for the study. This can be done by creating associations (e.g., links, references, access tokens) between a data area for the study and the various data storage areas shared by individuals. In this manner, the system can present a combined or aggregate data set for viewing and analysis, without having to copy or duplicate the data into the study's data storage area. The system can also provide interactive controls for operating on the data set as a whole (e.g., running statistical analysis, running search queries, applying filtering, running machine learning tasks (such as model training, generating predictions or inferences, and testing models).

In another general aspect, a method performed by one or more computers includes: identifying, by the one or more computers, a group of participants in a health research study; storing, by the one or more computers, data collected as part of the health research study in first data storage areas for the participants, each of the participants having a different first data storage area; receiving, by the one or more computers, data indicating second data storage areas for the participants that store health data collected separately from the health research study; linking, by the one or more computers, the first data storage areas and the second data storage areas to a research study data area; and providing, by the one or more computers, access to a combined data set by pooling of the first and second data storage areas for the participants.

Other embodiments of these aspects and others discussed below include corresponding systems, apparatus, and computer programs, configured to perform the actions of the methods, encoded on computer storage devices. A system of one or more computers can be so configured by virtue of software, firmware, hardware, or a combination of them installed on the system that in operation cause the system to perform the actions. One or more computer programs can be so configured by virtue having instructions that, when executed by data processing apparatus, cause the apparatus to perform the actions.

The details of one or more embodiments of the invention are set forth in the accompanying drawings and the description below. Other features and advantages of the invention will become apparent from the description, the drawings, and the claims.

BRIEF DESCRIPTION OF THE DRAWINGS

FIGS. 5-9 are figures showing additional aspects of the decentralized application ecosystem and data sharing platform.

Like reference numbers and designations in the various drawings indicate like elements.

DETAILED DESCRIPTION

Figure 1A:
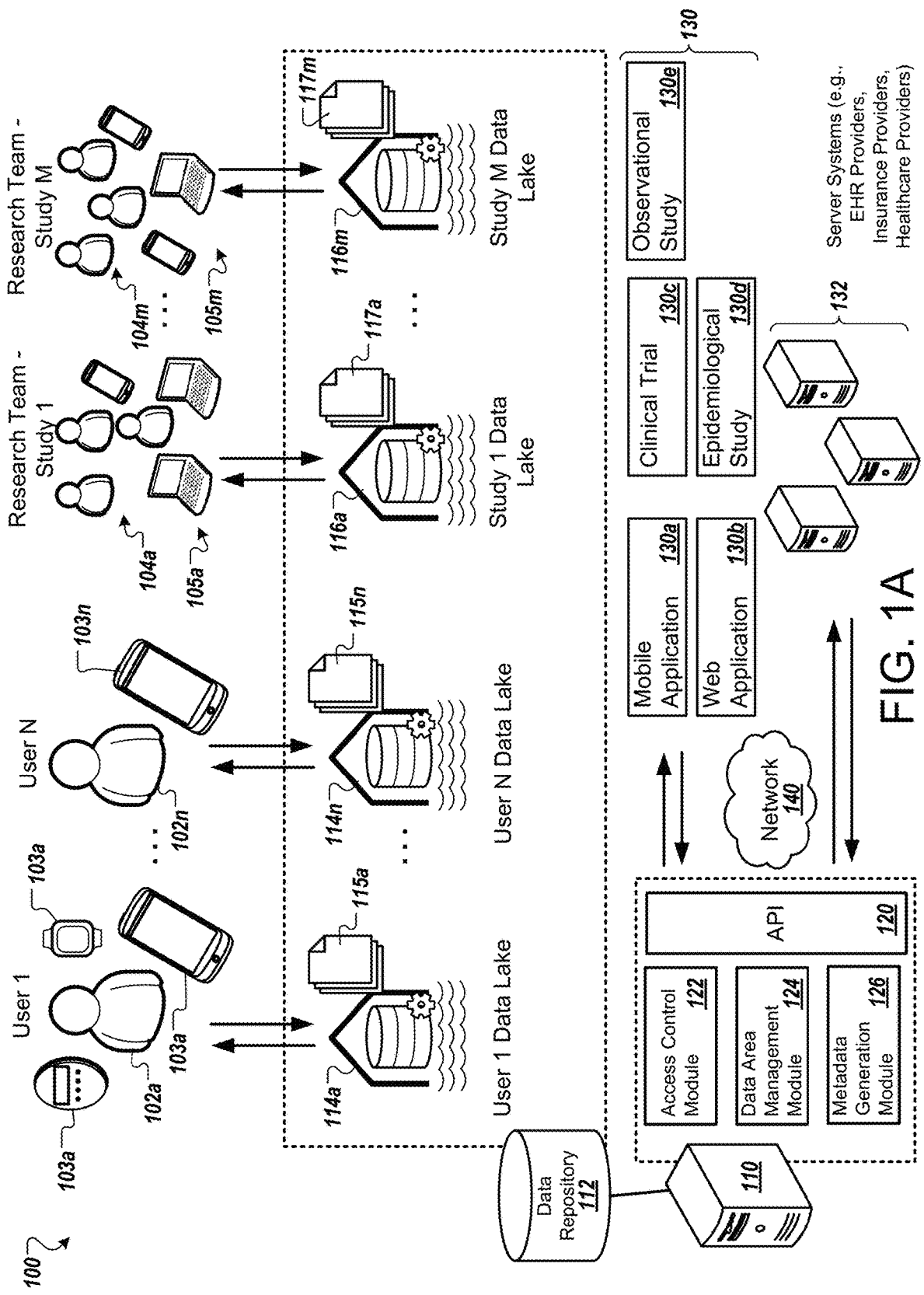
FIGS. 1A-1D illustrate a decentralized application ecosystem and data sharing platform.

The present document describes a computing platform that can facilitate secure sharing of health data and help users manage access to health data by a decentralized ecosystem of applications. The platform provides an application programming interface (API) that enables applications to request and receive access to health data. The platform manages the health data for an individual according to the authorization that the individual grants, allowing the individual to retain control over how his or her health data is accessed and used. For example, the platform enables a user to grant or deny authorization at different levels of granularity, e.g., by source of the data, by the type or category of data, by time range in which the data is collected, and more. Similarly, the platform enables users to control permissions, the duration of access, number of accesses, and other access parameters at the level of individual data sets or data collections. The system thus enables individuals to maintain ownership and control of their health data while still enabling the data to be easily accessed by a diverse set of applications when individuals authorize access.

For individuals, the platform provides enhanced security, privacy, and control of their health data. The health data for each individual can be stored in a logical data storage area. Individuals can have multiple different data storage areas for different purposes or to store data from different sources. For example, different data storage areas can be created and maintained by the system for different health research studies that the individual participates in. Each study stores data in its own separate storage area. The participant can access any or all of the areas, and may selectively grant studies access to data in the data areas for other studies. Similarly, different data storage areas can be used for data from different doctors or health providers, for data generated by different devices (e.g., an activity tracker, a weight scale, a mobile phone, etc.), and other sources. The individual whose health data is stored in the data storage area can have control to set permissions and grant and revoke access, with standardized or customized limitations on access, to different applications and organizations.

The techniques discussed herein can be used widely in digital health, digital therapeutics, precision medicine, personalized medicine, precision health. Precision medicine, also called personalized medicine, can involve determining the unique disease risks for an individual and the treatments that will be most effective for an individual. As discussed herein, the system can not only identify or predict the health risks an individual faces, but also characterize the likelihood or severity of those risks. For example, all people many have some non-zero risk of a heart attack, but some factors or combinations of factors can cause the level of risk to vary widely from one individual to the next. The system provides the ability to accurately quantify a risk level that is personalized for an individual, based on the person's unique genome and epigenetic data (e.g., the individual's behavior, environment, etc.), as well as other information such as the current context or situation of the user, the user's medical history, and so on.

Precision health includes precision medicine, and can include interactions that occur outside the setting of a doctor's office or hospital, such as disease prevention and health promotion activities. Precision health involves approaches that everyone can do on their own to protect their health as well as steps that public health systems can take.

The system is applicable to research efforts as a tool to assist researchers and facilitate scientific discovery. In this case, the system may be leveraged to benefit researchers in designing, monitoring, updating, and enhancing a health research study such as a clinical trial, a cohort study, or other research endeavor.

Health research studies can involve remote monitoring of various aspects of the health of individuals, including physiological measures, behaviors, activities, mood or mental state, and so on. The monitoring can be carried out using various digital technologies (e.g., using sensors, patient surveys, user devices, and other data collection techniques). In particular, the techniques herein are very effective in carrying out decentralized clinical trials. Decentralized clinical trials are often executed using telemedicine and mobile or local healthcare providers, using processes and technologies differing from the traditional clinical trial model. In many decentralized clinical trials, most or all of the monitoring and data collection occurs in the patient's normal daily environment rather than in a physician's office or other clinical setting. In many cases, participants in decentralized trials visit a dedicated trial site (e.g., hospital or medical office) rarely or not at all. A decentralized clinical trial can use software and digital devices, such as smartphones and wearable devices, to provide monitoring and other interactions while participants proceed through their normal activities at home, at work, at school, etc. These studies are also sometimes referred to as "virtual trials" or "digital trials."

Many types of health research studies, including decentralized clinical trials, are used to evaluate and test the efficacy of pharmaceuticals. For example, different types or phases of clinical trials can have different objectives, which can affect the types of data to be collected and conditions to be monitored. A phase 0 trial may be experimental, with the aim to determine how a drug is processed by the body. A phase I trial may be used to evaluate drug safety and dosage, for example, to find the best dose of a drug that has limited side effects, by gradually increasing dosage until side effects become too severe or positive effects are observed. A phase II trial can be used to assess safety as well as effectiveness or efficacy of a drug, potentially evaluating effects of a drug in combination with other drugs or other factors. A phase III trial may be used to further assess safety and effectiveness of a drug, for example, to compare effectiveness or efficacy of a drug with a reference, such as a current standard-of-care drug. The application ecosystem and the personal data storage areas discussed herein can facilitate it and increase the efficiency of any or all of these types of studies.

FIG. 1 is a block diagram that shows an example of a system 100 for managing and sharing health data among a distributed set of applications. The system 100 includes a computer system 110 that manages a data repository 112 of health data for different individuals and research studies. The computer system 110 makes the health data available through an application programming interface (API) 120, but access is limited to what users of the system (e.g., individuals, researchers) authorize. The access control features enable users to selectively share their health data with various different software or systems, referred to generally as "applications" or "apps." These include various applications that may be created, run, hosted, or otherwise provided by third-parties that are independent from the computer system 110. The computer system 110 enables users to specify and adjust how their own health data will be accessed, for example, specifying which applications can access health data, specifying the portions of health data that can be accessed, and specifying limitations or restrictions on access. The computer system 110 then enables applications to access the authorized data areas while enforcing the limitations that the respective users specified.

The computer system 110 can be a server system that includes one or more computers. The computer system 110 can include cloud computing systems and can be distributed across different geographic locations, e.g., clusters, data centers, or server farms. The data repository 112 can include various data storage devices, including local data storage, remote data storage, cloud computing data storage, network-attached data storage, and so on.

The computer system 110 manages the storage and retrieval of health data of various individuals 102a-102n. The computer system 110 stores the health data in the data repository 112, in which health data for different individuals 102a-102n is stored in separate data lakes 114a-114n for each individual 102a-102n. The data lakes 114a-114n represent logical divisions of data storage, and do not need to be separate physical storage drives or systems. The health data stored in the data lakes 114a-114n can be obtained from a variety of sources, including healthcare providers, researchers, medical devices, wearable devices, health records, applications, insurance providers, and more. For example, individuals 102a-102n may each have one or more corresponding devices 103a-103n that is used to generate and/or use health data about the individual 102a-102n. The health data in the data lakes 114a-114n can be in any of multiple different forms, such as structured data (e.g., data in tables, columns, rows, or otherwise corresponding to a data model or data schema), unstructured data, text, numerical values, images, documents, video data, sound recordings, raw sensor data, processed sensor data, etc. Various types of sensors can be used to collect health data that is stored in data lakes 114a-114n. Examples of sensors that can be used include accelerometers, light sensors, cameras, microphones, inertial measurement units (IMUs), GPS receivers, and compass sensors. Other devices can include other sensors, such as pulse or heart rate sensors, EKG sensors, photoplethysmography sensors, and so on.

As discussed further below, the health data for each individual 102a-102n can optionally be subdivided into multiple separate data lakes or data areas, either within a primary data lake 114a-114n for the individual 102a-102n or as multiple independent data lakes 114a-114n per individual 102a-102n. The multiple data lakes or data areas for an individual may be linked together or may be entirely separate depending on the configuration used and the authorization provided by the individual 102a-102n. Each data lake 114a-114n, as well as any other data lakes or data areas defined, can be secured separately, for example, encrypted separately and/or have separate access conditions and limitations set. For example, each different data lake or data area can have a corresponding encryption key or set of credentials needed to obtain access, and those keys or credentials can be different for each data lake or data area.

In some implementations, data from different data sources is stored in different data lakes or data areas that have separate access authorizations and settings applied. For example, for the individual 102a, there are three devices 103a that provide health data: a glucometer providing blood glucose measurements; a smartwatch or activity tracker that provides heart rate measurements and activity tracking (e.g., actigraphy data such as step count); and a smartphone that provides movement data, device usage data, images, and other sensor data. Any of the devices 103a may also provide user input data, such as the responses of the individual 102a to surveys, ecological momentary assessments (EMAs), or other prompts. The individual 102a may choose to store the health data from each of the devices 103a in a single data lake 114a. However, there are also advantages to storing the data from different devices 103a in different data lakes or data storage areas for which access is separately managed.

As an example, by storing the data from each device 103a in a separate data storage area, the individual 102a obtains more fine-grained control of the authorization for each data collection for the individual 102a. For example, the glucometer can be authorized to store data to a data area specifically for glucometer data. This limits the amount of data the glucometer can access or modify, providing extra security and isolation if the glucometer is compromised. Similarly, if the individual 102a uses an application for managing or tracking diabetes, the individual 102a can authorize the application to access only the data area with the glucometer data. The health data that is not needed by the application, such as data from the individual's other devices 103a, remains inaccessible to the application, securely partitioned in separate data areas that are not shared unless the user affirmatively authorizes it. In fact, even the existence of the other data areas can be hidden from the application. For example, each data area can be managed separately and independently, in some cases not even linked to the user identity of the individual 102a. The individual 102a may supply a user identity and link to other data areas only as the user chooses, and access to one data area does not identify or provide access to other data areas unless the individual 102a permits it. As a result, even if one application gains full access to the data area with glucometer data, the identity of the individual 102a and the existence of other data areas for the individual 102a (and the addresses or identifiers for the other data areas) cannot be determined.

The computer system 110 enables the individual 102a to authorize or deauthorize access to each of the individual's data areas individually for each application (more generally, for each system, service, software module, or entity). The computer system 110 also enables the individual 102a to set separate access limitations that customize an application's access differently for the different data areas. For example, even if an application is authorized to access two data areas for the individual 102a, the computer system 110 can apply different access restrictions for those two data areas (e.g., read and write access to a first data area, but read-only access to the second data area), according to the settings of the individual 102a. Similarly, the settings may further limit access by limiting a number of accesses allowed, limiting a range of time in which an application may obtain access, limiting the time range of data that can be accessed (e.g., allowing access only to records created within the last year), limiting media types that can be accessed (e.g., text and numerical data, but not image data), limiting the type or content of data that can be accessed (e.g., allowing access to heart rate measurements and weight measurements, but denying access to respiration rate measurements and blood test results), limiting data according to the source of the data (e.g., allowing access to data generated by a watch and a first application, but denying access to data generated by a glucometer or a second application), limiting the set of actions permitted (e.g., create, read, write, delete, update, etc.), limiting whether the application gaining access to a data area can access further data areas or third-party services linked to the data area, and more.

The computer system 110 can also provide and manage data lakes for entities other than individuals. In general, data lakes or data areas can be provided for researchers, healthcare providers, organizations, companies, departments, groups, projects, and so on. As an example, data lakes 116a-116m can be data lakes for different health research studies, each including health data collected for the corresponding research study. As an example, the data lakes 116a-116m can be allocated to securely store the data from the corresponding studies. The research studies can each have a corresponding set of users 104a-104m (e.g., researchers) who access their data lakes 116a-116m with respective sets of devices 105a-105m. The data lake 116a for a clinical trial, for example, can include data collected from participants in a cohort for the clinical trial, e.g., biospecimen analysis results, survey responses, sensor data collection, physiological and behavioral measurements, in-person or telemedicine visit notes, diagnoses, prognoses, projections, and so on.

During the period of participation in the study, participants' devices and applications may generate various types of data relevant to the study, such as physiological and behavioral information. The data can include user input (e.g., participant-reported symptoms or outcomes, survey responses, EMA responses, user interactions with an application, performance in video games or other activities) and sensor measurements (e.g., step count measured daily, heart rate measurements made hourly or triggered contextually, sleep data determined using mobile phones or wearable devices, mobile phone activity usage, location tracking data from global positioning system (GPS), etc.). When a participant enrolls in or otherwise begins participation in the study, the participant can be granted access to a software module for the study (e.g., a web page, a web application, a mobile device application, a module to extend or configure a mobile device application, etc.). Through enrollment or registration with the study, or as part of the downloaded software module, the participant's device can be provided (i) the address for a data lake in which the application is to store data, and (ii) authorization data (e.g., a token, key, or other credentials) to enable access to add data to that data lake.

Over the course of a research study, data generated for participants in the cohort (e.g., a selected set of individuals enrolled to participate in the study) can be transmitted to the computer system 110 and stored in the data lakes 114a-114n for the participants, the data lake(s) 116a of the research study itself, or both. As participants participate in a study, health data is generated and sent to computer system 110 by the devices and applications used by the respective participants. This can result in a stream of asynchronous data upload transactions as devices and applications of participants initiate storage requests through the API 120 to upload data items individually or in batches (e.g., sets of data items collected over time). The volume of transactions can be high, especially as the computer system 110 supports the data collection for many different research studies concurrently, each with different cohorts of participants that contribute data using different sets of devices.

Participants' devices and applications can be configured to automatically initiate user interactions and sensor measurements, consistent with the study protocol of the study, to carry out the monitoring and observations needed for the study. Data collection actions can be directed by a remote server system that assists management of the clinical trial, and the server system can be different from the computer system 110. Data collection actions for participants can also be initiated by applications or software modules on user's devices, for example, on a scheduled basis, in response to contextual triggers or detected conditions, manually initiated by participants, and so on. A device or application can configured for use in the study by the device receiving and applying a configuration profile or software module for the study. The received profile or module can include rules, code, links to Internet resources, content, and other elements to cause an application to carry out the monitoring and user interactions of the study. The process of configuring a device or application can also involve the user authorizing the computer system 110 to store the participant's data, such as by the participant authorizing use of (and potentially establishing limits on access to) an existing data lake 114a-114n, the participant authorizing a new data lake to be created for the participant's data generated in the study, or authorizing the participant's data to be stored in a data lake 116a for the study. The configuration process can set the addresses for the data lakes or data areas that will serve as the destination(s) for data generated, as well as to generate proof of authentication so that a device or application can access the data lakes or data areas that correspond to those addresses. Once configured, the device or application can automatically send newly collected data for the participant over the communication network 140, for example, as new data is collected, in response to a condition or trigger, or according to a schedule. The collected data is sent to the computer system 110 using the API 120, with data storage requests being addressed to the appropriate data storage areas, e.g., to the data lake 116a for the study that the individual 102a is participating in, the data lake 114a for the participant 102a, or both.

To enable data to be entered into the data lake 116a, devices and applications of study participants can store the address for the data lake 116a for the study and authorization data (e.g., an authorization token or other credentials). Each participant may also be authorized to obtain limited data from the data lake 116a for a research study, such as the portion of stored data collected by or about the participant (but not data for other participants) and general information about the study (e.g., study progress, findings or conclusions, plans and timelines, aggregated de-identified study results, etc.). In this manner, participants can gain personal benefit of the monitoring and testing that comes from participation in the study, with the computer system 110 enabling the participant-accessible data from the data lake 116a to be viewed, shared with applications of the participant (e.g., a personal health tracker), shared with the participant's personal physician, etc.

In some implementations, health data about participants in research studies may be stored using a different study-specific data lake each participant. In effect, each participant would have his or her own personal data lake 114a-114n specifically for data generated as part of the research study, where the participant can view it and control sharing for data about himself or herself. In allocating this type of data lake, the computer system 110 would grant the researchers or the organization running the study an authorization to access and use the data, according to what the participants agreed to when they enrolled in the study. The data lake 116a may then link to or be associated with all of the individual study-specific data lakes for the study. As discussed below, this linkage may be done transparently to show researchers an aggregate collection of the data from the component data lakes for individuals, without the overhead and duplication of actually copying data into the data lake 116a. Any other data lakes 114a-114n that participants decide to share with the research study (e.g., data lakes or data areas for personal health care, personal health tracking data, other current or prior research studies the participant was involved in, etc.) can also be linked to the data lake 116a. What the computer system 110 exposes to researchers 104a for the data lake 116a can be a combined collection of the study-specific data lakes for the study and any other shared data lakes that participants authorized to share.

The ability to selectively link data lakes or data areas increases the efficiency of storage by avoiding the duplication of data. The technique also greatly increases the efficiency of accessing combinations of data by applications and individuals. The computer system 110 can seamlessly combine data from separate data lakes to greatly reduce the complexity of access by applications. The work of aggregating the data can be done dynamically by the computer system 110, which applies the access control settings of each linked data lake in generating the aggregate data set presented to a researcher or application. When accessing a data lake with multiple linked data lakes, the computer system 110 can present the combined set of data from the multiple data lakes as a single data set, with the computer system 110 dynamically computing the characteristics of the combined data set and abstracting away the divisions and structure of linked data sets so that applications do not need to be aware of the details of the storage mechanism. Although each linked data lake may have its own separate authentication, encryption, and access settings, the computer system 110 can apply those settings respectively to each data lake when computing the combined data set, in a way that is transparent to the applications making use of the API 120. Thus, users or applications can access a first data lake and be provided a data set that is in effect, a dynamically-created aggregation of various linked data lakes that are referenced by the first data lake, where the aggregation includes all of the information from the linked data lakes that the first data lake is authorized to receive according to authentication tokens in the first data lake and the respective policies of the linked data lakes.

As an example, a data lake for an individual's participation in a clinical trial can simply be referenced or linked to the main data lake 116a for the clinical trial. The data for the individual 102a is stored in a single individual-specific data lake (such as data lake 114a) rather than be duplicated in both a personal data lake and a clinical trial data lake. As a result, storage requirements are minimized and uploads of newly collected data can be made to only a single data lake. The participant maintains personal control over her own data, with the ability to access to the raw data, access real-time status information about data collected, authorize or deauthorize sharing of that data (e.g., to private physicians, to other research studies, etc.), and set privacy settings and access limitations. Even so, the researchers can access the data collected for the research study, including that of the individual 102a, through a main data lake 116a that references the data lakes for each of the participants. The access of the study can be set and limited according to the terms of the participants' consent when enrolling in the study (e.g., limiting a range of records that can be accessed, limiting access to a term of 5 years, etc.).

As with individual data lakes 114a-114n, the data lakes 116a-116m may be further divided into smaller data lakes or data areas to provide greater control and more fine-grained sharing. For example, the data for a clinical trial may be stored in different data lakes, divided according to: collection methods or data sources (e.g., self-reported data, biospecimen analysis, user device measurements); data types or data categories (e.g., cardiovascular data in one data area, behavioral data in another data area, etc.); different geographic locations of participants (e.g., by country, state, county, city, etc.); participant categories (e.g., categories defined by medical conditions, demographic attributes, control vs placebo group assignment); treatment regimens or protocol versions; subgroups of a cohort (e.g., by sub-study or group within a cohort); ranges of time (e.g., with data for different months or years in separate groups); and so on.

The computer system 110 can store the data lakes 114a-114n, 116a-116m in a secure, access-controlled manner. This often includes storing the health data of different data lakes 114a-114n, 116a-116m with different encryption keys and/or requiring valid credentials or access token(s) for a data lake to be provided before accessing (e.g., reading or writing data to) a data lake. As a result, the health data in the data lake is inaccessible to applications and users that do not have the proper access authorization (e.g., those that do not provide a valid token, key, certificate, or other credential for the data lake).

The computer system 110 manages access to the data lakes 114a-114n, 116a-116m by receiving and acting on data access requests (e.g., requests to read or write data to a data lake) as well as management requests (e.g., to change settings, add or remove authorization, create new data lakes or data areas). These requests can be made through the API 120. Optionally, a combination of multiple APIs can be used for different types of data access, or separate APIs for data access and data lake management can be provided.

A variety of different applications 130 can request and receive access to the data lakes 114a-114n, 116a-116m to read and/or write data. Examples include a mobile device application 130a and a web-based application 130b. In addition, applications 130 can represent different health research studies, such as a clinical trial 130c, an epidemiological study 130d, an observational study 130e, and so on. Many different applications 130 of these types and others can be provided through many different channels, e.g., web sites, application stores, research study galleries, toolbars or extensions for web browsers and other applications, and so on.

Some types of applications 130, such as the mobile device application 130a, may be downloaded to and be installed on a device, so that the application 130a resides and executes primarily on a mobile device or other client device, potentially also exchanging data and receiving instructions from one or more servers. Other types of applications, such as the web application 130b, may be accessed through a web browser and run in primarily or in large part on a server, with user interface components and executable or interpretable code being downloaded to the client device dynamically (e.g., just-in-time, or for each session, as accessed by the client device). Additional combination and hybrid approaches can be used. Whichever implementation techniques are used for the applications 130, either a client-side or server-side component or both can initiate requests through the API 120 and receive and process the data that the computer system 110 provides in response.

Through the API 120, an application 120 can authenticate itself, identify a data lake 114a-114n, 116a-116m or data area, provide proof of authorization to access the identified data lake or data area, and specify the data to store or retrieve. For example, an application 130 can send an access request that identifies the application, e.g., an identifier of the application requesting access and access credentials to authenticate the application (e.g., proof that the request is from the application that purports to send the request, such as an account password, a certificate, information for an authenticated session, etc.). The request can also include the address of the data lake 114a-114n, 116a-116m or data area to be accessed, as well as proof of authorization to access that data lake or data area (e.g., an authentication token, key, or other data demonstrating authorization). The request can also indicate the type of action requested (e.g., create, read, update, delete, etc.) and can specify the data to retrieve (e.g., as a query, SQL statement, file name or file path, record identifier, etc.) or the data to add or edit (e.g., as a data payload to add, a reference to a file to upload, etc.).

The computer system 110, upon receiving an access request over the communication network 140, verifies the authentication of the sending application 130, e.g., by checking to see whether the credentials or session information match the known information for the application 130. The computer system 110 can store information about registered applications, current authenticated sessions, and other information to perform this verification. If the application 130 is authenticated, the computer system 110 verifies that the address in the request corresponds to a valid data lake or data area, and also verifies that the provided proof of authorization (e.g., authorization token) grants access to the data lake or data area. The computer system 110 also reads policy information and access settings in the data lake and/or the authorization token to determine the level of access that is granted and any limitations on access that should be applied. If the authorization token is valid for the data lake or data area, the computer system 110 then acts on the request to the extent the authorization and access limitations permit. The computer system 110 may decrypt health data from the data lake or data area and provide the decrypted to the application 130, potentially re-encrypting as appropriate for the communication protocol used for security in transmission. In some implementations, authorization tokens may include some or all of an encryption key used to access the encrypted data in a data lake 114a-114n, 116a-116m. In other implementations, the authorization token may not provide the appropriate key for decryption, but the computer system 110 may store the appropriate key in association with the data lake, so that when authorization is verified the computer system 110 can look up and use the appropriate key from storage that the computer system 110 maintains. The computer system 110 provides a response to the application 130 that made the request, e.g., providing data retrieved if the application 130 made a read request, providing a confirmation of successful write if the request was to write data, providing an notification if the transaction could not be carried out (e.g., indicating an error, a problem with the application authentication, a lack of valid data lake access authorization, a lack of permissions or access within the data lake, a failure to find data requested, etc.).

As an example, if an application 130 requests data from a data lake 114a-114n, the computer system 110 retrieves and provides the subset of data that both meets the specification in the request (e.g., in the set of files, records, or values requested) and satisfies the authorization and access limitations the individual 102a-102n placed for the application 130 (or generally for a category of applications or for all applications). This may result in providing less than the requested data set. For example, an application 130 may request all heart rate measurements, but the user may have authorized that only the previous month of data can be provided to the application 130, and so the response from the computer system 110 would include the heart rate measurements for only the previous month.

The same general process of requesting access to the data lakes 114a-114n, 116a-116m can be performed for performing access on behalf of different users (e.g., individuals, researchers, etc.), organizations, companies, and so on. As discussed further below, each data lake 114a-114n, 116a-116m can also have a corresponding set of metadata 115a-115n, 117a-117m, and requests can be made through the API 120 to obtain metadata for a data lake 114a-114n, 116a-116m in the same manner. In addition, the API 120 supports requests to manage the data lakes 114a-114n, 116a-116m also, including to create or delete data lakes or data areas, to grant or deny access or to change the access limitations, to change whether metadata is provided for a data lake or data area and what content of metadata is provided, and more.

The functionality and purposes of the different applications 130 can vary greatly. Some applications can be generated for a limited purpose or single purpose, such as uploading activity tracker data or reminding a user to take a blood sugar measurement. These applications may have very simple needs, allowing a user to grant limited access to a single specific data area and keep the applications isolated from other data areas. For example, an activity tracker data upload application may simply need write access (without read access) to a single data area for storing activity data. Similarly, the blood sugar reminder application may need only read-only access to a data area specifying a treatment plan or schedule for measurements. Other types of applications may be more complex, involving multiple data types, multiple data areas, read and write access, and so on. For example, some applications may be designed to provide digital therapeutics, precision medicine, personalized medicine. athletic performance training, mental health support, or other interactions.

Through the API 120, the computer system 110 enables a diverse set of applications to gain access to a wide set of health data from diverse sources. The applications 130 can be developed and provided in a decentralized manner, independently and separately from the computer system 110. As long as the applications 130 communicate according to the API 120, the applications 130 can access any of the health data that users choose to authorize through the computing system 110. Nevertheless, individuals still retain ownership and control of their data 114a-114n, and can set privacy as they desire, including keeping their individual data lakes or data areas anonymous (e.g., not linked to a user identity) and unconnected (e.g., so a data lake or data area does not identify other data lakes or data areas of the individual). Access by applications 130 remains customizable and limited by the owners of the respective data lakes 114a-114n, 116a-116m, with each individual 102a-102n or research team 104a-104m having the ability to customize and modify the access limitations for each authorization given, as well as customize and modify the type of access to metadata 115a-115n, 117a-117m that is allowed, if any, without specific authorization to the data lake.

The computer system 110 is configured to interface with various other systems 132, such as EHR providers, insurance providers, healthcare providers (e.g., individual hospitals, doctor's offices, and other facilities). The computer system 110 can store information about the communication protocols and APIs of these different server systems 132 to facilitate data transfer and data synchronization with these third-party systems. For example, the computer system 110 can provide interfaces for an individual 102a to (1) identify a doctor, hospital, or other healthcare provider that stores EHR data for the individual 102a (e.g., through a search interface, a lookup from a list, entering an electronic address, etc.) and (2) enter user credentials to access the third-party system 132. The computer system 110 can then log in to the server system 132 on the user's behalf and, using the communication protocols and API specifications stored, the computer system 110 can import, export, or synchronize data between one of the data lakes 114a-114n or data areas with the data for the individual at the server system 132. As a simple example, a user may have EHR data stored in an on-premises database or other data storage system. The computer system 110 provides an interface for an individual to identify this system and provide credentials, and then can automatically set up a new data area for the individual to correspond to that EHR data source. The computer system 110 can import the records into the data area managed by the computer system 110, and can also perform periodic checks to update the contents of the data area to include new information from the EHR data provider's collection as new information is added.

For each data lake 114a-114n, the computer system 110 can generate and store a corresponding set of metadata 115a-115n that is derived from the health data in the corresponding data lake 114a-114n. The metadata 115a-115n can facilitate data sharing and the effective matching of individuals to the most relevant research opportunities, benefiting both individuals 102a-102n and researchers 104a-104m. Although an individual 102a may desire to keep his health data private and his identity unknown, the person may still be willing to provide generalized, de-identified information describing the data area. This can include metadata indicating properties such as the types of health data available from a data area (e.g., blood pressure data, heart rate data, actigraphy data) and/or the sources of the health data in the data area (e.g., activity tracker, mobile phone, clinical trial). Thus the metadata 115a-115n can provide generalized, de-identified data about the nature of data currently stored in or being collected in an ongoing manner to data area, without revealing the values of the underlying data (e.g., indicating that blood pressure measurements are stored, without indicating the values of any of the measurements). Using the metadata 115a-115n, although an application or user may not yet have authorization to access the underlying health data of a data lake 114a, the computer system 110 can still provide (subject to the authorization and settings of the individual 102a) indicators of the types of data or classifications for the data lake 114a.

The computer system 110 allows users to set different levels of privacy to control the types and amounts of metadata that are provided. These levels can range from no metadata being provided, to only certain types of metadata being provided, to providing a full indication of types of data available (e.g., sources, types, and time ranges for data in the data area). In some cases, a user may choose to include in the metadata 115a-115n some health information, such as indicators of a person's current or past medical history (e.g., whether the person has a disease such as diabetes, cancer, etc.). Even when authorizing metadata 115a-115n to be provided, the computer system 110 gives the individual 102a-102n control over which applications receive the metadata 115a-115n. For example, the individual 102a-102n may restrict the content of the metadata 115a-115n. The individual 102a-102n may specify categories of metadata 115a-115n to include or exclude, and within each category the individual 102a-102n can specify specific items or types of items to include or omit. The metadata 115a-115n is determined for each data lake or data area individually. If an individual 102a-102n has multiple data lakes for different purposes or data sources (e.g., for personal health tracking, for different research studies the individual is participating in, for different devices or applications, etc.), the metadata 115a-115n indicates the contents of the specific data lake 114a-114n it corresponds to. In some implementations, an individual 102a-102n can enable the metadata 115a-115n to also describe contents of linked data lakes. For example, if authorized by an individual, the metadata for a first data lake that links to three other data lakes of the individual can include metadata describing the entire collection of data across the four data lakes.

The computing system 110 enables individuals 102a-102n to set and customize which types or sets of metadata 115a-115n are provided to different types of applications. For a given data lake 114a, some metadata items, such as the fact that the data area includes data from a mobile phone, may be made publicly available to any and all applications, users, or services, without the need for authorization or authentication. Other metadata items, such as classifications of the types of data or semantic interpretation of the data (e.g., that the data lake 114a stores blood pressure measurements, heart rate measurements, diet information, sleep tracking information, etc.), may also be provided without authorization to access the data lake 114a but only to qualified applications or certain types of applications, or in response to a user confirming or approving access by an application. The computer system 110 can store profiles for various applications 130 that register with the computer system 110 and can manage the provision of metadata according to the properties indicated by the application profiles.

For example, applications may be assigned different classes or categories by the computer system 110. Some applications may be more trusted or more thoroughly vetted by the computer system 110 (e.g., trust levels 1, 2, 3, etc.), and the individual 102a-102n may limit metadata access to certain levels (e.g., only available to applications with trust level 2 or higher). The applications may correspond to different entities and entity types (e.g., universities, non-profit organizations, government organizations, corporations, etc.), and individuals 102a-102n may limit metadata access to certain types of organizations or set different limitations for different organizations or types of organizations. The function and purpose of the applications can be categorized as well, specifying applications by function (e.g., monitoring, coaching, research, etc.), by topic or health area (e.g., cancer, diabetes, heart disease, athletic performance, etc.), and so on, and individuals 102a-102n can apply metadata access limits or authorizations by these factors as well. Thus, the computer system 110 can enforce individuals' authorizations and limitations on access to metadata 115a-115n, to provide different levels of access (e.g., access to different metadata content) for specific applications, groups of applications, and types or categories of applications. The computer system 110 can grant differing levels of access to the metadata 115a-115n to different applications or different categories of applications, just as the computer system 110 enforces individuals' authorizations and limitations for access to the underlying health data in the data lakes 114a-114n. The metadata access authorizations and limitations can be set and customized for each individual 102a-102n, and can be set and customized separately for each of the data lakes or data areas for any single individual 102a-102n.

The metadata 115a-115n can be used to provide personalized, value-added benefits to users and researchers without revealing a user's personal health data or identity. For example, an application can use the metadata 115a to give an individual a personalized preview or trial use of an application, personalized to the type of data and types of data sources available in a data lake or data area, without revealing the individual's private health data. For example, a user of a device can access a mobile device application or a web application and provide the address for a data lake or data area for the user. The application can then interact with the computer system 110 to request and receive the metadata 115a for the data area indicated by the address, subject to the constraints and limitations the user 102a has placed on access to metadata 115a for that data area. The application may have various different capabilities and functions, including different user interfaces, modules, interactive controls, and so on. Many of the different capabilities and functions may rely on having specific types of data. For example, one portion of the application may use diet information, another portion may use sleep tracking data, and another portion may use step count information. With the metadata 115a, the application can determine which types of data are available in the specified data area and the application can determine a subset of the features of the application that make use of the types of data available. This enables the application to provide a customized preview or explanation of the application, including with interactive interfaces, tailored for the subset of application capabilities that are relevant to the data in the anonymously-specified data area the user indicated.

As another example, researchers can use the metadata 115a-115n to identify and evaluate candidates for clinical trials. Many potential candidates to participate in a research study may have relevant health data already collected for prior research studies they have participated in, in personal health tracking data (e.g., exercise tracking, chronic disease coaching, sleep tracking, etc.), and in electronic health records (EHR) from healthcare providers. Traditionally, computer systems did not provide researchers the ability to determine whether a candidate had data available from these sources or what types of data was available, especially before a user gave consent to participate in the research study. Typical systems also did not allow researchers to access to health data generated for participants in studies by different sources or systems through a standardized or centralized API. The computer system 110 enables researchers to search for candidates using the metadata 115a-115n, identify which data lakes 114a-114n best fit with the needs of a research study (e.g., have the most complete or extensive sets of data collected or the most relevant ongoing data collection and data collection devices), and invite the individuals corresponding to the identified data lakes to participate in a research study.

The computer system 110 provides qualified parties, such as researchers registered with the computer system 110, the interfaces and functionality to search the metadata 115a-115n and find data lakes 114a-114n or data areas that meet certain characteristics. The computer system 110, provides individuals 102a-102n tools to control which metadata items about their data lakes 102a-102n can be shared with applications, researchers, and others, giving individuals 102a-102n the ability to control what information is available to be searched. Researchers that would like to understand a research candidate pool can run queries to determine statistics about the availability and usage of certain home health devices (e.g., glucometers, weight scales, activity trackers, etc.), as well as the rate that other types of health data are available (e.g., genomics data, EHR data, blood test results, etc.). Researchers can also search for specific data lakes that have specific features. The computer system 110 can provide interfaces for researchers to set criteria for data areas, e.g., data areas that: include data for researcher-specified types of data (e.g., blood pressure data, heart rate data, body weight, etc.); include data from researcher-specified sources (e.g., data generated by specific devices or categories of devices, data from physicians, data from insurance providers, etc.); have ongoing data collection active for researcher-specified types and sources of data; or have authorization to access researcher-specified additional resources (e.g., an EHR provider system, a cloud-computing data storage account, etc.).

The computer system 110 searches through the metadata 115a-115n to find data lakes 114a-114n or data areas that, according to the corresponding metadata 115a-115n, meet the researcher's criteria or which most closely meet the researcher's criteria. The computer system 110 can score and rank the identified data lakes 114a-114n or data areas for best fit to the data collection needs of a research study, to find the data lakes 114a-114n or data areas that may already provide much of the background data or even longitudinal monitoring data that is needed in the study. This can reduce the time and cost of performing research. One way is that the computer system 110 identifies candidate participants that already have needed data collected and available, thus reducing the amount of new data collection (e.g., reducing the types of data, amount of data, or duration of data collection) that would be needed for that participant in the study. As a simple example, a research study may require one month of data collection of data about sleep and exercise, as well as a blood test, prior to an intervention such as taking a medication. The computer system 110, by searching the metadata 115a-115n, can identify the data lakes 114a-114n of individuals 102a-102n that already have that data available (while keeping the actual measurements and values encrypted or otherwise secured). These data lakes 114a-114n represent candidates that are particularly valuable to the researchers, since the researchers can avoid the cost and logistics of the blood test and also skip the 1-month period for establishing the baseline data.

As another benefit, searching using the metadata 115a-115n identifies candidate participants that, through the metadata 115a-115n about data collected previously, have demonstrated historical patterns of data collection or device usage consistent with a study protocol. This is an indicator that the individual has a high likelihood of success in complying with the same or similar data collection in the future. In the example above, the presence of sleep and exercise tracking data generated prior to joining the study, as indicated by the metadata 115a, indicates that the corresponding individual 102a, though anonymous to the researcher, would likely be successful at sleep and exercise tracking during the study. Similarly, a research study may require participants to use an activity tracker to monitor exercise. Searching by the computer system 110 can determine that the metadata 115a indicates ongoing data collection with an activity tracker device in the corresponding data lake 114a. This provides a benefit to the researcher, because the corresponding individual (1) has shown familiarity with and ability to use an activity tracker, suggesting high likelihood of complying with activity tracker usage requirements, and (2) indicates that the individual has an activity tracker device and so the researcher would be able to avoid the cost and delay of having to supply one to the candidate. These features can also greatly benefit the candidates, allowing researchers to match individuals to research studies that provide the greatest benefit (e.g., in terms of health information gained or potential health improvement) with the lowest effort required on the part of the individual (e.g., leveraging existing stored information or ongoing data collection procedures to require the least burden and additional time and effort on the part of the individual).

In addition to identifying candidates that are a good fit for a research study, the computer system 110 also enables researchers to incentivize candidates to join a study according to the contents of the candidates' data lakes 102a-102n. For example, the researchers can offer individual candidates different amounts of money or other benefits, with greater incentives being given to candidates whose data lakes have more of the data items or data sources needed for the research study. Researchers can incentivize different individuals to join, in amounts proportional to the value that the individuals' data areas 114a-114n provide (as determined from the metadata 115a-115n), e.g., the extent that the historical data, current data, ongoing data collection, and linked data sources or other resources indicated by the metadata 115a-115n can supply information needed to meet the study protocol and/or selection criteria (e.g., factors for eligibility to participate in the study).

Figure 1B:
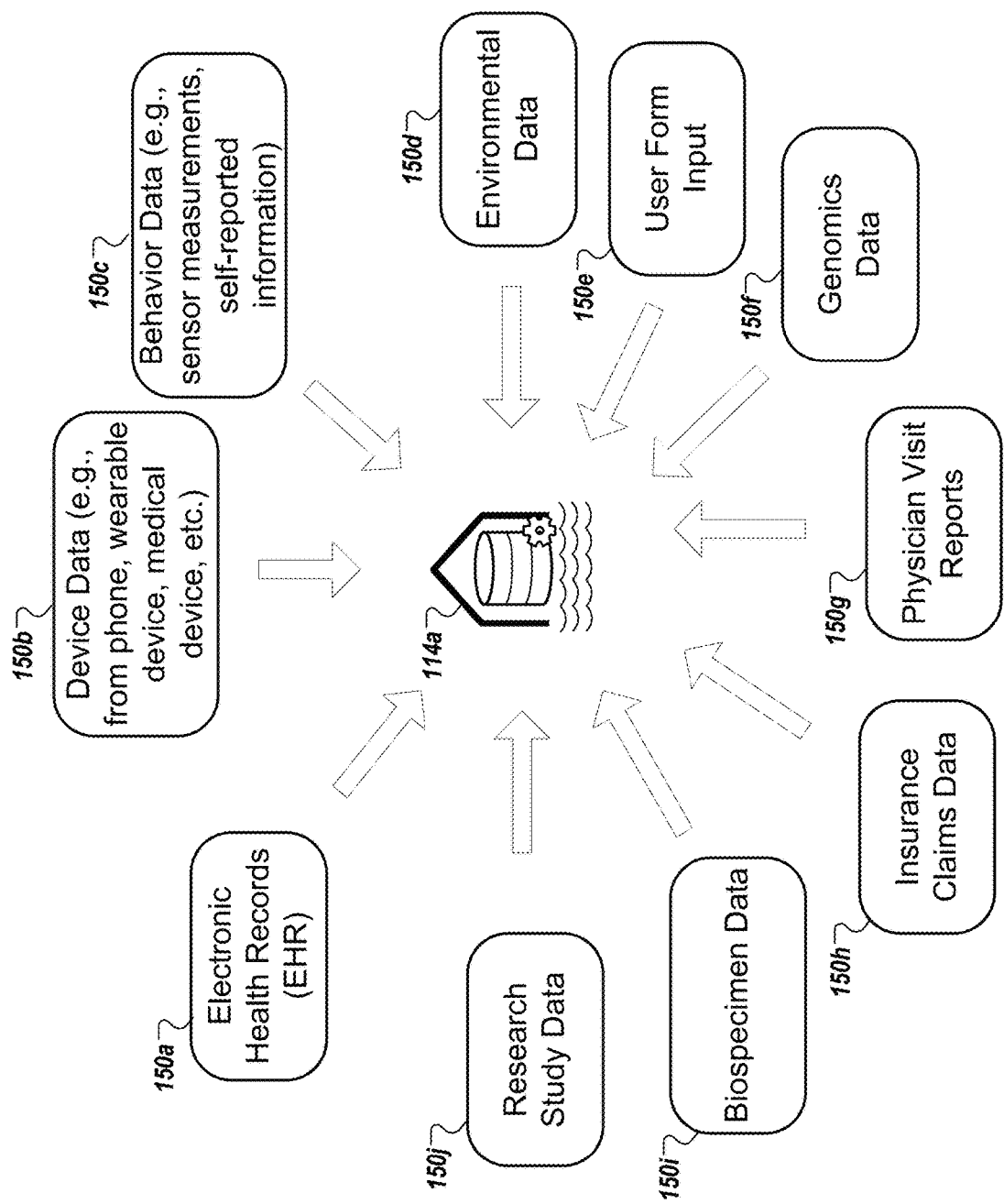

FIG. 1B is an example of many different types of data and sources of data that can be provided to a data Lake 114a-114n. The example shows single data lake 114a that receives many different types of data from different data sources. However, in other situations, individuals may choose to store different types of data or data from different sources in separate data lakes or data areas as will be discussed further below.

There are many types of data that can be captured and stored in health data lakes 114a-114n, 116a-116m. The data may reflect a wide variety of health conditions and behaviors, including those relating to biological, physical, mental, emotional, environmental, social, and other inputs. In some embodiments, data may be omics data (e.g., data relating to genomics, proteomics, pharmacogenomics, epigenomics), including cardiac-related data (e.g., data from ECG monitors, heart rate monitors, blood pressure monitors), respiratory-related data (e.g., data from spirometers, pulse oximeters), neurological-related data (e.g. data from EEG monitors), behavior data (e.g., data on movement patterns, gait, social avoidance), substance use data (e.g., data regarding use of alcohol, medication, recreational drug, tobacco), sleep data (e.g., data relating to motion, heart rate, body temperature, perspiration, breathing, ambient light, ambient sound, ambient temperature), exercise data (e.g., data related to performance, distance covered, activity, maximal oxygen consumption), physical activity data (e.g., data regarding step counts, heart rate, flights climbed, altitude, data from a fitness tracker), mood data (e.g., data relating to happiness, depression, brief mood introspection score), biologically sampled or derived data (e.g., data related to blood, urine, saliva, breath sample, skin scrape, hormone level, glucose level, a breathalyzer, DNA, perspiration), lab or diagnostic data (e.g., assay data, blood test results, tissue sample results, endocrine panel results), positioning or location data (e.g., GPS data, gyroscope data, altimeter data, accelerometer data, linear acceleration data, received signal strength indicator from an emitter such as a WIFI access point, data from a BLUETOOTH sensor or sensor network, data from a cellular tower), environmental data (e.g., air quality data, ozone data, weather data, water-quality data), vehicle data (e.g., speed, location, amount of time driving, mood while driving, environmental data in the car), drug data (e.g., prescription information, pharmacological data).

In the example, the data Lake 114a receives and stores electronic health records (EHR) 150a. These can include all kinds of data from health care providers, such as user data from forms the user filled out, medical history, allergies, vaccination history, current medications, historical medications, office visit reports, and more.

The data Lake 114a also receives and stores device data 150b, for example data generated by a phone, wearable device, medical device, and so on. this data may include information about physiological measurements and behavioral measurements, and May include self-reported data provided through a device as well as sensor data. In many cases, device usage information and device status information can be indicative of user health and activity. For example, location data from a GPS receiver and activity data from accelerometers or an inertial measurement unit can indicate the user's level of activity and exercise. Additionally, information about travel of the user and other behavioral factors including sleep can be very important to show the behavioral components of a user's health. As a result, the information about times and amounts that devices are used, the applications used and amounts of time used for each, and other device status information can be used to assess a user's health.

The data lake 114a can include behavioral data 150c, for example, sensor measurements or self-reported information. In addition, the data lake 114a can include environmental data 150d, such as information about air quality, temperature, weather, and so on. Additional types of data include user form input 150e, which may be provided through a device or represent records digitized from paper sources.

The data lake 114a can include genomics data 150f. Examples include whole-genome genotypes, whole-genome sequences, or whole-exome sequences. Other genomics data 150f may include results indicative of the presence or absence of specific genes or genetic markers, such as the presence of particular single-nucleotide polymorphisms (SNP). Beyond genomics data, other "omics" data can be obtained and stored, including proteomics data, pharmacogenomics data, and epigenomics data.

The data lake 114a can also receive and store data such as physician visit reports 150g, insurance claims data 150h, and biospecimen data 150i (results of blood tests, urine tests, etc.

The data lake 114a can also include research study data 150j. In many cases, the research study data 150j represents data collected as part of the participation of the individual 102a as a participant in a cohort of a research study. User-provided reports, medical test results, and at-home monitoring results generated as part of the study can all be included. In addition, analysis performed by the researchers, including conclusions, risk factors, projections, diagnosis, and other outputs of the research study for the user 102a or for the study as a whole can also be included.

Figure 1C:
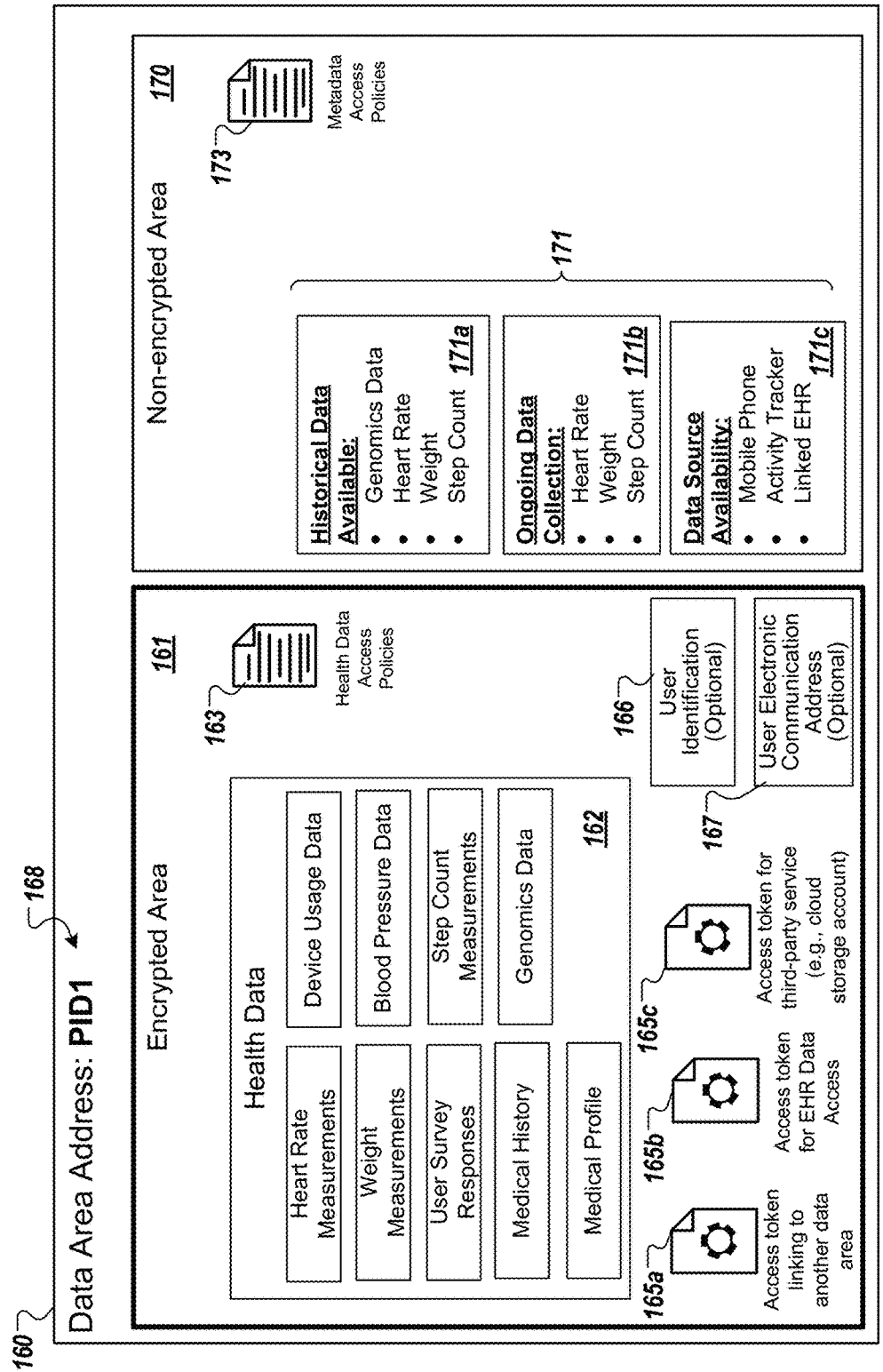

FIG. 1C Shows a more detailed example of a data area or data Lake for the individual 102a. The data area 160 can be one of many different data areas or data Lakes for the individual 102a.

The data area 160 is identified by a unique address 168, shown as "PID1" in the example. Data areas are identified by and are accessed using the assigned address. the addresses assigned by the computer system 110 can be globally unique or universally unique across the entire set of data areas managed by the computer system 110. As a result, the address 168 can include sufficient information to distinguish this particular data area 160 from all others. in some implementations, the address 168 can be an alphanumeric string that is automatically generated by the computer system 110 when the data area 160 is first created.

The data area 160 can have multiple areas within it, such as an encrypted area 161 and a non-encrypted area 170. The encrypted area 161 includes private data that is not accessible through the computer system 110 or the API 120 except with proof of authorization from the user 102a, such as in the form of an access token that grants a specific application 130 (or even a specific installed instance of the application 130) access to the specific data area 160. The non-encrypted area 170 includes metadata 171 about the data area 160, such as categories or classifications of data available in the data area 160 without providing the underlying measurements, records, values, of the Health Data 162.

The encrypted area 161 stores health data 162, health data access policies 163, and access tokens 165. The health data 162 can include structured data or unstructured data from any of various sources, such as those discussed with respect to FIG. 1B. Generally, applications are permitted to access only the Health Data 162 portion of the encrypted area 161. The other elements shown are used by the computer system in the management of dead areas and provision of customized Access Control. For example, the policies 163 and access tokens 165 are not accessible by any application through the API 120.

The health data access policies 163 can include user settings and current authorizations made by the individual 102a, including any customized limitations or restrictions on access for particular applications 130. In some implementations, the scope of access that any given authorization to an application 130 provides is securely encoded in the access token provided to the application 130 (e.g., signed, hashed, embedded, or otherwise stored in a tamper-evident manner). As a result, the limitations on access may be discernible from the access token that the application 130 provides when it initiates a transaction (e.g., read, write, etc) with the data area 160 through the API 120. Nevertheless, to simplify access tokens and/or To allow the computer system to better verify the authorized scope, the computer system on 10 can store a list of current authorizations, and potentially a list of modified or revoked authorizations, in secure storage, whether in the data area 160 or in a separate data structure. For example, the computer system can maintain, for each data area, a list of valid access tokens and application identifiers corresponding to them, along with data specifying the authorized data as well as any restrictions on access for that application or token. Maintaining a list or table of valid authorizations can be especially useful to support real time revocation of authorization and real-time modification of authorization by individuals. When a user revokes or modifies authorization, the computer system 110 can update the health data access policies 163 accordingly, for example to mark a token as invalid or mark an application 130 as no longer authorized. Then, if the application 130 presents its previously-valid token, the computer system 110 can determine using the policies 163 that, although the token is genuine, the authorization that it represents was revoked and so does not longer authorize access.

In general, each authorization to access any portion of the health data 162 has an accompanying expiration. In some cases, the authorization may last for a month or a year and then expire automatically based on the passage of time. Other authorizations may be set with automatic renewal conditions, such as an authorization for one month that is set to automatically renew in 1-month periods until the user 102a ends the renewal.

The tokens 165 represent authorization that links or grants access to other data areas or to other resources and services. Tokens 165 may extend the scope of the health data 162 by effectively incorporating the contents of other data areas. For example, the token 165a is an access token that links to another data area of the user 102a. This token 165a grants access so that any application 130 that has been granted sufficient access to the data area 160 also gains access to the health data in the data area corresponding to the token 165a. The computer system 110 can also store, in association with the token 165a, the address for the data area that the token 165a grants access to. As a result, the data area 160 can be used to represent a combination data set of two data areas without the need to copy data into the health data 162 and duplicate the records. Also, as data is added to the linked data area, those updates flow through to the combination represented by health data 162 and the linked health data, with no need for synchronization processing. Instead, the combined data set is determined at the time of each access to the data area 160, to dynamically represent the current contents of both data area 160 and the linked data area.

The token 165b is an access token that permits data access to an EHR system or platform, Such as data for a Physicians database, hospital records or other set of Records. The computer system 110 can use the token 165b to import information from the HR System, for example, automatically on a periodic basis or manually and responds to a request from a user.

The token 165c is an access token for a third-party service, such as a cloud computing data storage account. Some applications 1:30 may make use of third party services as sources or destinations of data. For example, an application 130 may process data in the health data 162 to generate a report about a user's health, and then store the report in a cloud computing account that the user specifies. if the user has provided access authorization to the application 130, The token 165c enables the application 130 to read data from or store data to the third party account. In some implementations, the computer system 110 handles access to third-party services to the API 120 so that the actual token 165c is not provided to or accessible to the application 130. For example, if the application 130 will store the document in a third-party account outside of the platform provided by the computer system 110, then the application 130 can request information about any linked accounts through the API 120 and also send requests through the API 120 for the computer system 110 to store the document in a linked account. As a result, the application 130 identifies the account that is the destination for the document and provides the document to the computer system 110, and the computer system 110 uses the token 165c to communicate with the third-party service and gain access to the third-party account.

In general, the data areas, such as the data area 160 can be arranged to be anonymous or de-identified, so that the data area 160 does not indicate the user identity of the user that owns the data area 160 or whose data is stored in the data area 160. In some implementations, the computer system 110 itself does not store or track the relationship between data areas and user identities. However, in some cases, it may be desirable for the computer system 110 to be able to contact the user or otherwise determine which user corresponds to a data area (e.g., to assist a user in recovering information about the user's data areas). As a result, when authorized by the user, the computer system 110 may optionally store user identification 166 and/or an electronic communication address 167 for the user (e.g., phone number, email address, etc.) in secure storage of the data area 160 or in another data structure managed by the computer system 110.

The non-encrypted area 170 includes various types of metadata 171 as well as metadata access policies 173 that specify which metadata should be generated and which applications 130 can receive the metadata 171. As examples of metadata 171, the computer system 110 can indicate historical data available 171a, which represents the categories or classifications of data that are stored in the health data 162. The metadata 171 can include indicators for the types of data subject to ongoing data collection 171b. The computer system 110 can use patterns of historical data entry to the data area 160 to determine whether certain types of data are being repeatedly or regularly collected. In addition, the computer system 110 can look at the dates and times of records added in the whole state of 162 to determine whether the data collection for different types of data meets a set of criteria to represent I'm going to get a collection. The metadata 171 can indicate the data sources that provided the health data 162 in metadata about data source availability 171c. For example, the computer system 110 can access the records in the health data 162 and extract information about the sources (e.g., applications, devices, etc.) that provided that data. The computer system 110 can also examine the health data access policies 163 and the tokens 165 to identify the sources of data that have authorization to provide data to the data area 160.

The computer system 110 allows users to specify which types of metadata are generated for their data areas, as well as set different levels of access to metadata for different types of applications 130. in some cases, the computer system 110 provides at least some standardized levels of privacy that a user can choose from. For example, a first level may provide no metadata 171 about a data area. A second level may provide limited metadata, such as only types of data sources 171c. A third level of metadata access may indicate data source availability 171c and types of already-collected data available 171a.

Figure 1D:
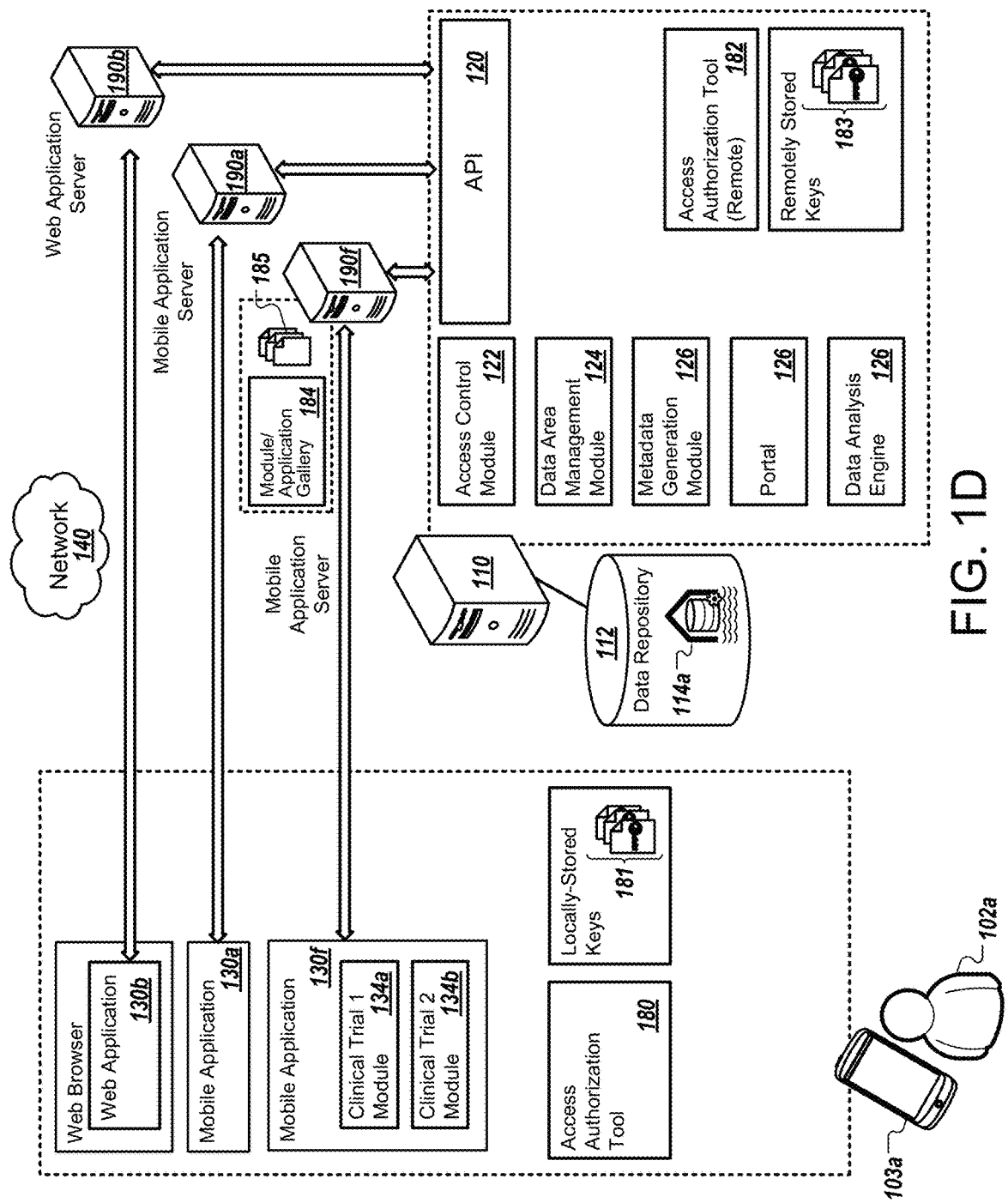

FIG. 1D shows additional information about interactions between devices in the system 100. In the example, the device 103A access has various different applications provided in different forms. These include a mobile application 130a that is installed on the device 103A. For example, the mobile application 130a may be downloaded from an application store and installed on the device 103a. Another application is a web application 130b that runs in a web browser on the device 103a.

In addition, a mobile application 130f is configured to download and use multiple different modules that each act as separate applications and can access data areas. For example, a single mobile application 130f may be customizable or extendable by downloading modules for different clinical trials. In this case, there is a module 134a for a first clinical trial as well as a module 134b for a second clinical trial. Each of these modules can include software, configuration data, user interface content, media items, and other content to cause the mobile application 130f to provide the interactions and data collection needed for the user 102a to participate in the corresponding research study. A server 190f can provide a gallery 184 of different modules (e.g., different research studies, programs, health applications, etc.) that can be downloaded. The server 190f may provide a web page or a list of modules 185 available, and then provide the modules 185 that the user selects.

For the applications 130 to access health data for the user 102a, the applications 130 need to be authorized to access specific data areas for the user 102a. To facilitate this, the mobile device 103a can store an access authorization tool 180 That interacts with the computer system 110 to grant authorization to specific applications 130 as requested by the user 102a. The user 102a can store keys 181 locally at the device 103A, where the keys 181 provide the proof of authorization of the user 102a to manage the respective data areas for the user 102a. The user 102a may alternatively store keys in another manner, including in cold storage (e.g., offline or in non-electronic storage), off the device 102a, in a separate security token device, or in another manner.

When an application 130 is being configured and first needs access to a data area, the application 130 can initiate a function call or procedure that involves the access authorization tool 180. For the web application 130b, this may involve redirecting the user from the browser to a user interface of the access authorization tool 180, where the user 102a can select from the data areas for which keys 181 are stored. From this interface, the user can authorize an application 130 to gain access to a specific data area or multiple data areas. The access authorization tool 180 interacts with the computer system 110 to generate or receive from the computer system 110 an access token specifically authorizing the web application 130b to access the specific data area(s) the user 102a specified. The access authorization tool 180 then provides the access token to the web application 130b, allowing the application 130b or an associated server 190b to gain access by providing the access token through the API 120, for as long as the access token remains valid (e.g., until it expires or is revoked). In a similar manner, a mobile device application 130a or modules of the mobile application 130f can invoke the access authorization tool 180, which can cause the mobile device to load the access authorization tool and switch focus in the user interface of the device 103a so the user 102a can specify the authorization needed and grant an appropriate access token.

The computer system 110 can also provide a remote access authorization tool 182 that is not an installed mobile device application. For example, the computer system 110 can provide the remote access authorization to a 182 as a web page, web application, or other Internet resource that can be invoked and used to create a new authorization for an application 182 even if a local access authorization tool 180 is not present. Rather than redirect a user to a local application, an application 130 can redirect to a web-based interface provided by the computer system 110. To facilitate this, a user 102a can authorize the computer system 110 to store keys 183 for the user's data areas, so the computer system 110 can generate access tokens for the user's data areas when authorized by the user 102a.

The computer system can include various other components. These include an access control module 122 that handles authentication, token issuance, verification of tokens, reading access policies, enforcing access policies, and so on. A data area management module 124 tracks the addresses that have been assigned and issues addresses for new data areas. The module 124 also handles creation of new modules and performs other management tasks. The metadata generation module 126 reads the metadata access policies of the data areas and generates metadata for them as authorized by the policies.

Figure 2A:
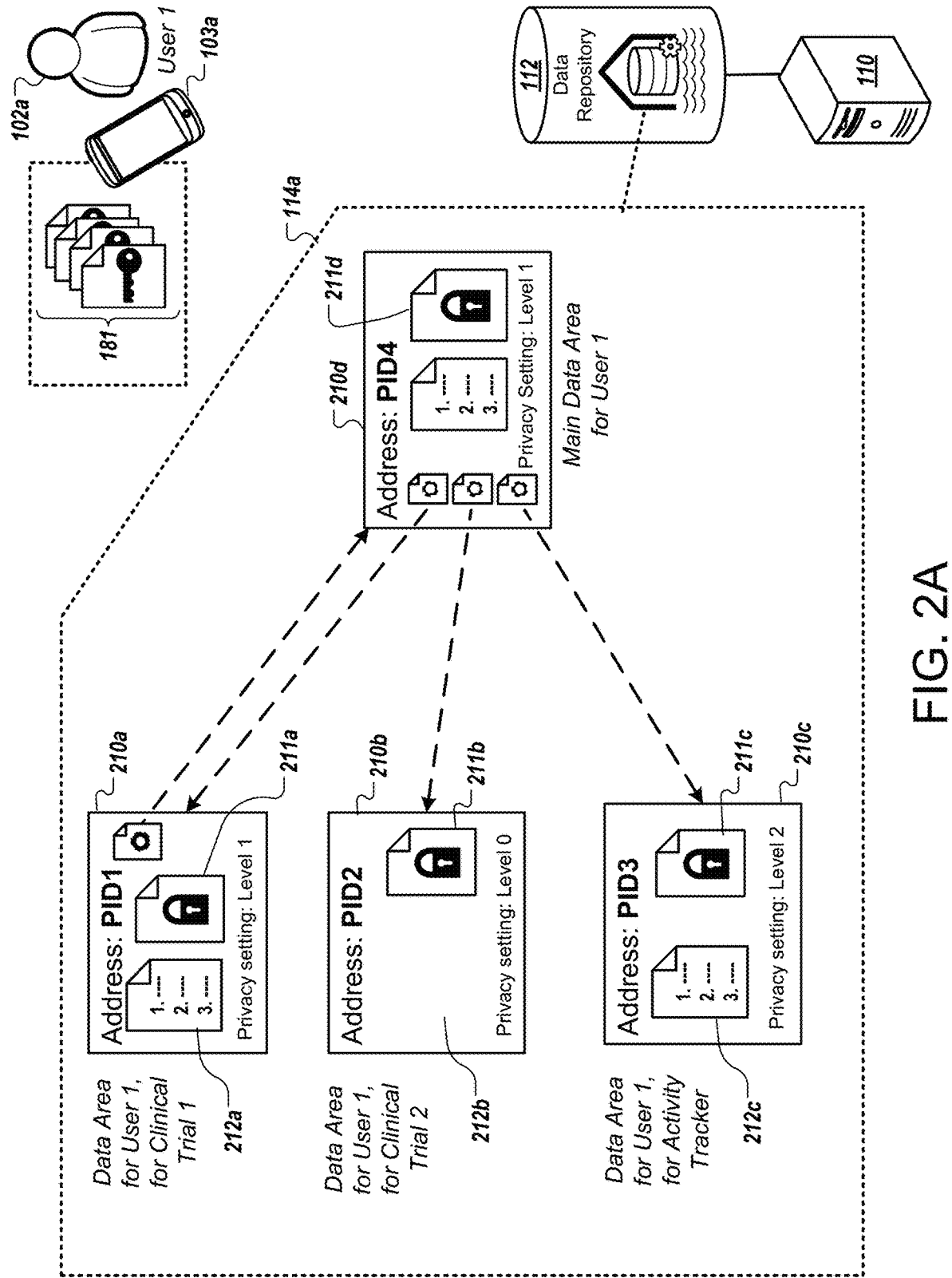
FIGS. 2A-2C illustrate additional aspects of the decentralized application ecosystem and data sharing platform.

FIG. 2A is an example showing multiple data areas for the user 102a. Each of the data areas 212a-212d includes a secure health data area 211a-211d and, if the user authorized it, metadata 212a-212d about the data area 212a-212d.

The data areas 212a-212d show an example how health data can be divided among separate areas. The data area 212a is a data area to store data generated for the user 102a for a first clinical trial. The data area 212b is a data area to store data generated for the user 102a for a second clinical trial. The data area 212c is a data area for the user 102a to store data generated by an activity tracker device. The data area 212d is a main data area for the user that includes general health data from various sources.

The data areas 212a-212d can include tokens that link data areas together or provide one data area access to the health data of another data area. For example, the main data area 210d includes three tokens that respectively enable access to the three other data areas 212a-212c. This allows the main data area 212d to be used as a collection of all of the data areas 212a-212d. For example, by granting an application 130 access to the data area 210d, the user 102a can effectively grant access to the combined set of data in health data areas 211a-211d, and the data can be presented to the application 130 as a single data set. When authorizing access to data area 210d, the user 102a may select whether or not to provide access to linked data areas 212a-212c.

Figure 2B:
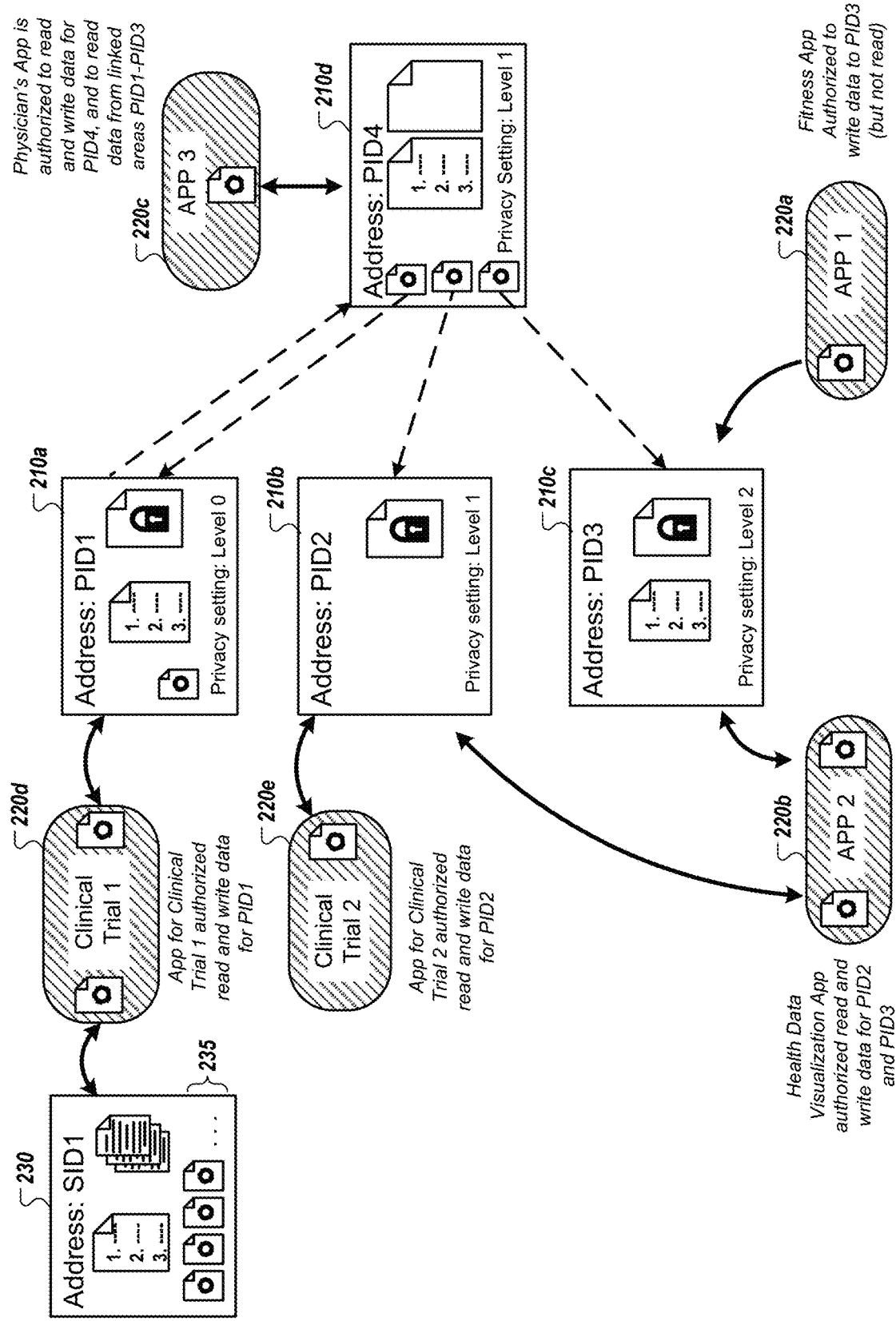

FIG. 2B shows examples of different authorizations that are provided to applications. The example shows applications to 220a-220e that each have different types of authorization. Each application 220a-220e is shown having an access token that the computer system 110 granted based on authorization of a user.

Application 1 220a is a fitness application authorized to write data to data area 210c but not to read data from the data area 210c. Application 2 220b is a health data visualization app that is authorized to read and write data to both of the data areas 210b and 210c. Application 3 220c is an application for a healthcare provider, which is authorized to read and write data to data area 210d. In addition, the authorization enables the application 220c to read data from (but not write data to) linked data areas 210a-210c.

Application 220d is an application for a first clinical trial that the user 102a has participated in or is currently participating in. The application 220d is authorized to read and write data for data area 210a, which is the data area designated to store data collected about the user 102a in the first clinical trial. Application 220e is an application for a second clinical trial that the user 102a has participated in or is currently participating in. The application 220e is authorized to read and write data for data area 210b, which is the data area designated to store data collected about the user 102a in the second clinical trial.

The example also shows a data area 230, which is a researcher's data area for the first clinical trial. This data area can include a variety of information that the researchers generate during the clinical trial. The data area 230 also includes a number of tokens 235 for data areas that the clinical trial has been authorized to access. These include tokens 235 for data areas created for or specific to the clinical trial, such as the data area 210a. Tokens 235 can also be included for other data areas that participants shared, such as data areas for other clinical trials, data areas for personal health monitoring, data areas for EHR or personal medical treatment, and so on.

Figure 2C:
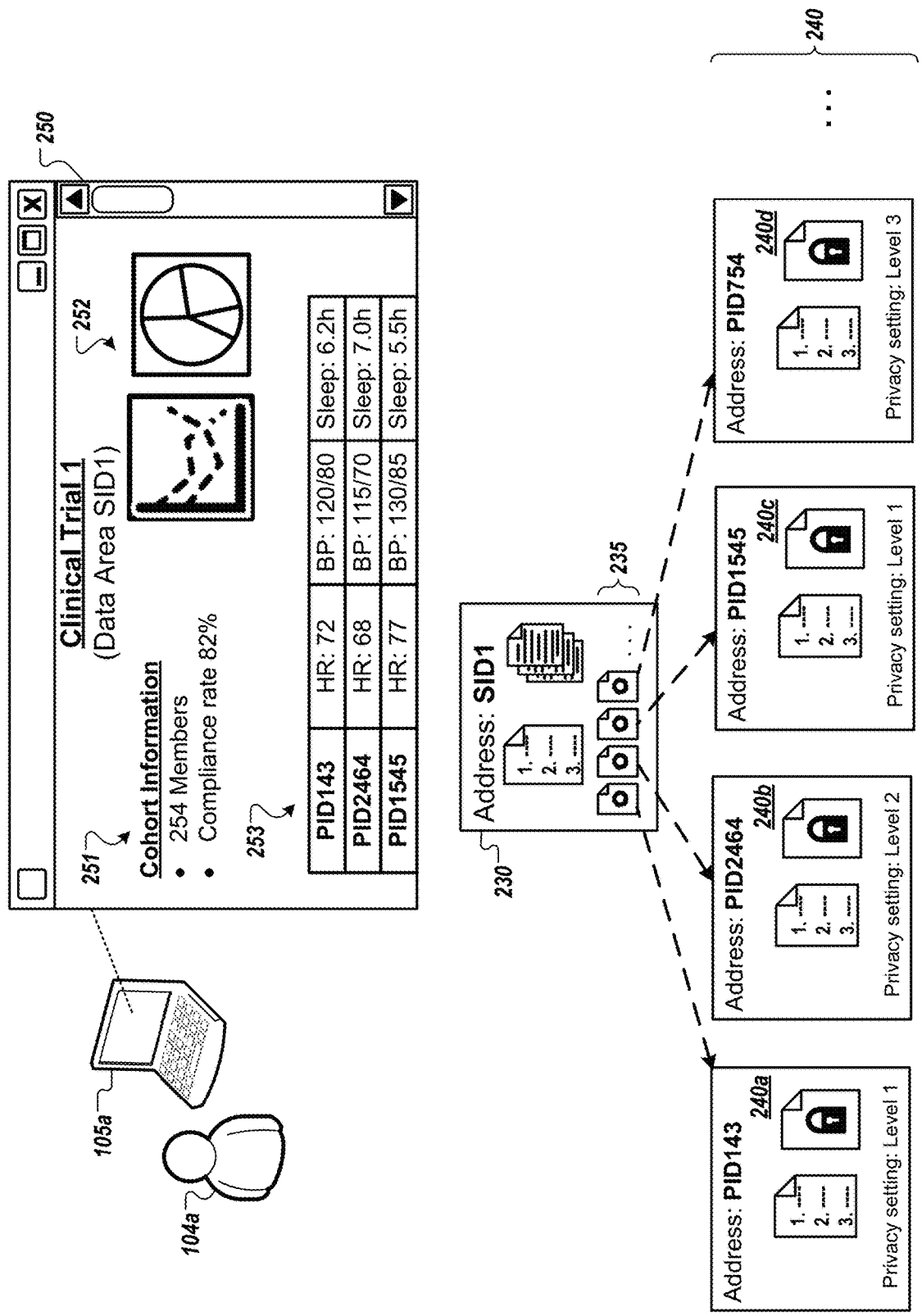

FIG. 2C shows an example of a researcher 104a accessing data for a research study. The researcher's device 105a shows a user interface 250 that shows the contents of data available through the data area 230 for Clinical Trial 1. The data area includes tokens 235 that link to or provide access to the data in each of various data areas 240a-240d. Each of the data areas 240a-240d represents the data area for Clinical Trial 1 for a different participant in the cohort for clinical trial 1. As discussed above, the participants can also share additional data areas that are not specifically for this clinical trial.

The user interface 250 shows various information derived from the data area 230 and linked data areas 240a-240d, including cohort information 251, data visualizations 252, and raw data 253. The computer system 110 uses the linking between the data areas 230, 240a-240d to provide a combined data set, by dynamically combining the health data from data areas 230, 240a-240d as if it were a single data set. When users grant access to their other data storage areas, e.g., for other clinical trials they have participate in, for personal health monitoring, EHR, insurance data, etc., this information can also be included and accessed through the main data area 230. This provides researchers the convenience of accessing all of the data for the clinical trial, including data that users may collect or bring from outside the clinical trial, but also gives each participant control of and access to his or her own health data. It also minimizes storage requirements by avoiding duplicate storage in a participant data area and a study data area, and avoids the overhead and bandwidth usage of repeatedly synchronizing the contents of individual data areas 240a-240d with redundant data in the study data area 230.

In the interface 250, the cohort information 251, data visualizations 252, and raw data 253 can represent data generated for the combined data set for the cohort, e.g., across all of the data areas 240a-240d. For example, the statistics and visualizations 252 can be compiled from the combined data set, and the raw data 253 can be a combination of measurements extracted from various data areas 240a-240d.

In some implementations, the computer system 110 enables users and applications to set rules and procedures that operate in an automated manner. For example, similar to smart contracts for blockchains, the computer system 110 can establish embedded logic that performs predetermined actions when certain conditions or triggers occur. This functionality can be provided using persistent scripts, stored procedures, database triggers or other techniques. The stored procedures can automate a workflow, triggering a series of actions when conditions are met. The data defining stored procedures can be stored with elements in different areas to allow for different types of invocation. For example, some may be stored in or associated with a data storage area, so the conditions are checked each time the data storage area is accessed. As another example, a stored procedure can be defined in or associated with an access token, so that the conditions are checked by the system each time the access token is used.

The stored procedures or persistent scripts can be used to inform users of accesses made to their data storage areas, for example, to alert the user when new access is attempted or when new data is added. The stored procedures or persistent scripts can be used in digital therapeutics, so that applications providing health monitoring and medical treatment can trigger new interventions and new data collection when predetermined conditions (e.g., health measures meeting thresholds) occur.

Similarly, the stored procedures or persistent scripts can be used to provide alerts to researchers about the compliance or health status of participants in cohorts for their research studies. For example, they can be set to inform researchers or to provide automated care when predetermined symptoms or side effects occur, or when compliance with a study requirement (e.g., for monitoring device usage, survey responses, taking mediation) drops below a threshold. Similarly, the conditions for a workflow can be set based on the condition of the cohort as a whole, such as when the overall compliance rate falls below a threshold, when compliance or enrollment in a particular subgroup meets a predetermined condition, when diversity measures for the cohort change or fall below a threshold, and so on. More generally, the aims of a study protocol often include acquiring certain information from participants in a certain amount of time (e.g., obtaining daily resting heart rate values). Procedures can be set to inform an application if that doesn't happen, so the application can adjust messaging and data collection techniques in response.

In some implementations, the stored procedures are used in logging by the system, for example, creating log data or notifying a user of when new data is stored, as well as indicating characteristics such as the type of data stored, amount of data stored, when the event occurred, the identity of the application or user that performed the access, and so on. Similar information can be generated for read access also. This information may also be used notify applications of access by a user or by other applications.

As an example, the system can use stored procedures or other logging to monitor access to data storage areas. This may reveal that research study 1 accessed a data set yesterday, but research study 2 accessed the data only once a year ago. The participant may decide to revoke access to research study 2 based on inactivity. As another example, reports are a form of data that can be shared with participants of research studies, and the system can notify participants when changes or updates to reports are available.

Automated procedures can also be used to detect and report harm to participants, as part of a study protocol. The protocol can indicate various risks, such as security risks or patient harm risk. The study protocol can indicate how to stop services, take patients off of treatment, inform follow ups from a health safety perspective, and the automated procedures can implement these changes or actions immediately when the triggering conditions are detected.

FIGS. 3A-3F show user interfaces showing an example process of a user obtaining access to an application. While the example shows an application for data visualization, the applications that are accessed and which can be customized can be for research studies, digital therapeutics delivery, health monitoring and other purposes, and these can all have experiences customized based on the metadata for a user's data storage area(s).

Figure 3A:
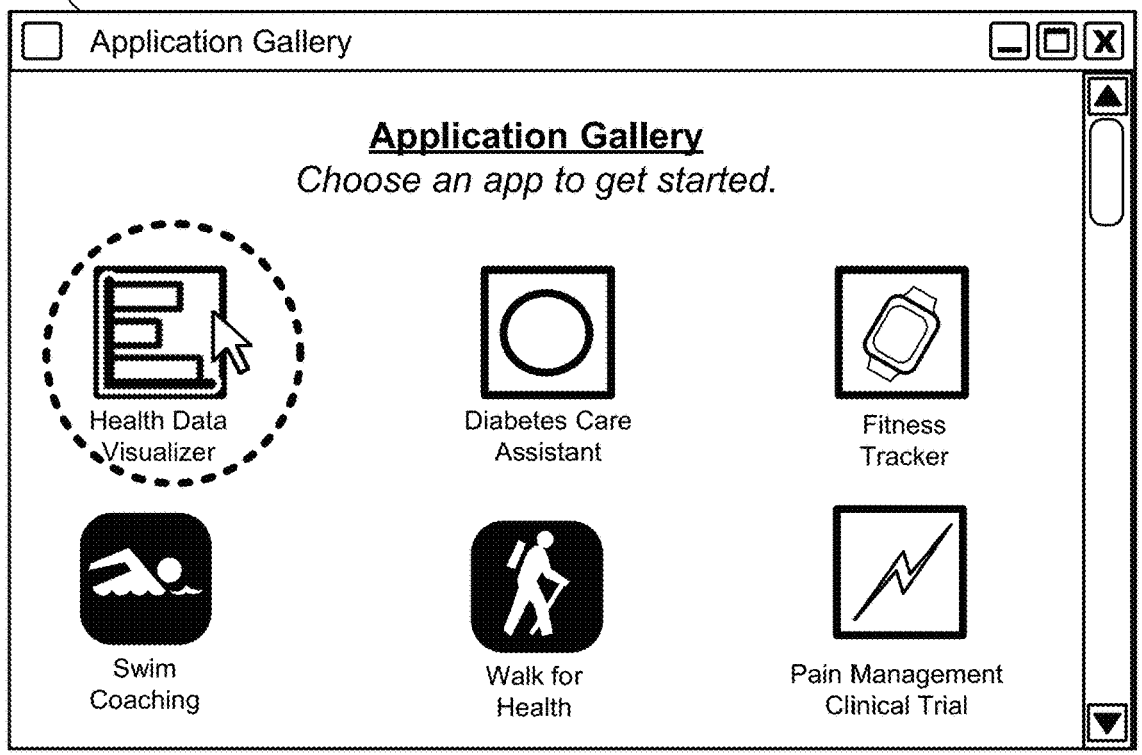
FIGS. 3A-3F are user interfaces showing a process of gaining access to an application.

FIG. 3A shows a user interface 300 showing a gallery of applications or application modules that are available. The gallery can be a web page, web application, a view of a native application, etc. The user selects the "Health Data Visualizer" application from the gallery. The applications can include applications for research studies, personal health tracking, coaching, and more. The applications can be categorized by health condition, purpose, provider, or other criteria. The listing can be personalized for the user, e.g., scored, ranked, or otherwise customized in presentation based on the user's interaction history, data area contents or metadata, health status or other factors. The gallery can also include search capabilities to enable a user to search for a desired application or type of application.

Figure 3B:
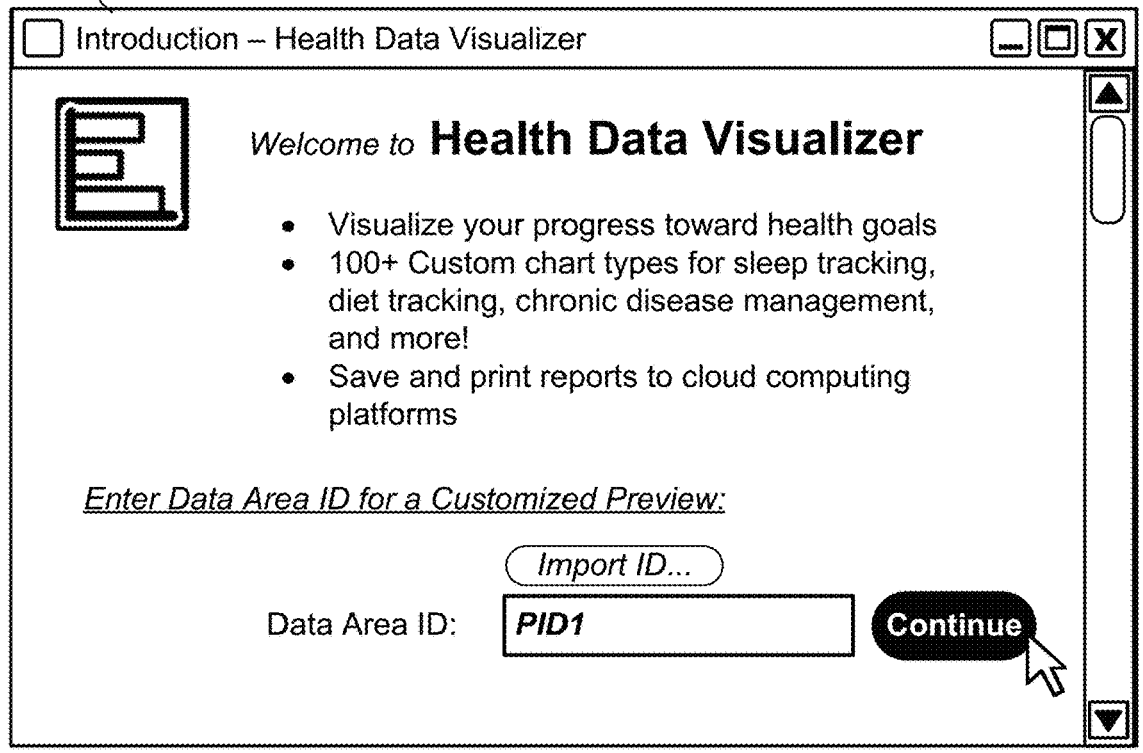

FIG. 3B shows a user interface 310 showing an introduction for the "Health Data Visualizer" application. The interface 310 includes a field for a user to specify a data area hosted by the computer system 110. For example, the interface 300 can have a control that enables a user to access the authorization tool 180 to see a list of the user's data areas that are managed by or registered with the tool 180 the user's device. The tool 180 can store and show user-generated nicknames or labels to make selection easier, and the tool 180 can enter the actual identifier for the selected label. In general, the system can hold identifiers, keys, and other data in a local, on-device digital wallet, or in a cloud-managed one. Actual identifiers or addresses can be 128 bit, 256 bit, or another appropriate length or complexity. As another example, the user can type, paste in, or otherwise enter an address (e.g., identifier) for a data area. Based on the provided address, the application interacts with the computer system 110 to retrieve the metadata that the user has authorized to be provided. Although the application does not have authorization to access the health data that is secured in the identified data area, the computer system 110 still provides metadata to the application, according to the user's settings for metadata for the data area.

Figure 3C:
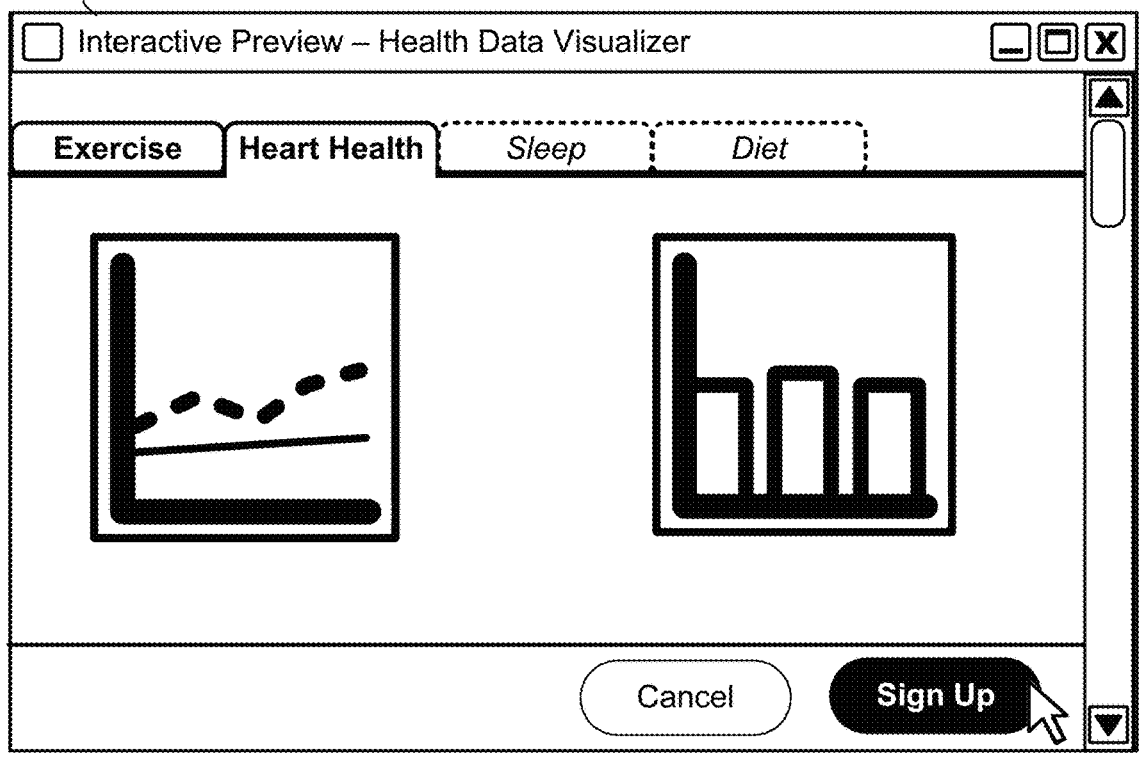

FIG. 3C shows a user interface 320 with a customized interactive preview or trial of the application. This preview includes a customized view that focuses or emphasizes the features of the application that can be used with the health data that the metadata for the specified data area indicates is present. The application obtained this metadata by sending a request for metadata that specified the user-provided address, to the computer system 110 through the API 120. These features are described further with respect to FIGS. 10 and 11. To this point, none of the user's health data or user identity has been shared with the application.

In the example, the application has features related to exercise, heart health, sleep and diet. The metadata for the indicated data area (PID1) indicates that the data area stores exercise data and heart health data, but does not store sleep and diet data. As a result, the application generates the user interface 320 to omit or adjust the section related to sleep and diet that are not relevant to the data area. After interacting with the application, the user selects to register with the application, to install the application, or otherwise gain access. As a result, the application issues a function call to invoke the authorization tool 180.

Figure 3D:
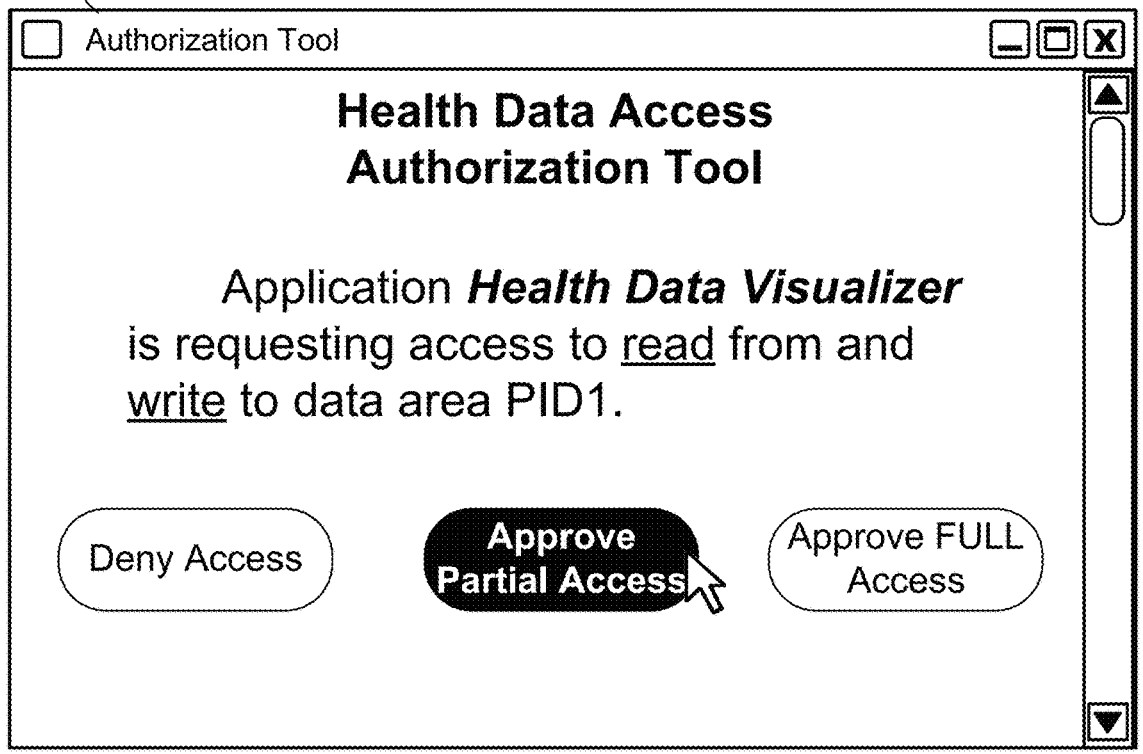

FIG. 3D shows a user interface 330 for the authorization tool 180, or alternatively the web-based authorization tool 183. The interface 330 gives the user options to approve or deny access, including to approve partial or limited access. In the example, the user selects to grant partial access, which leads to an interface for setting the level of access the user is willing to give to the application.

Figure 3E:
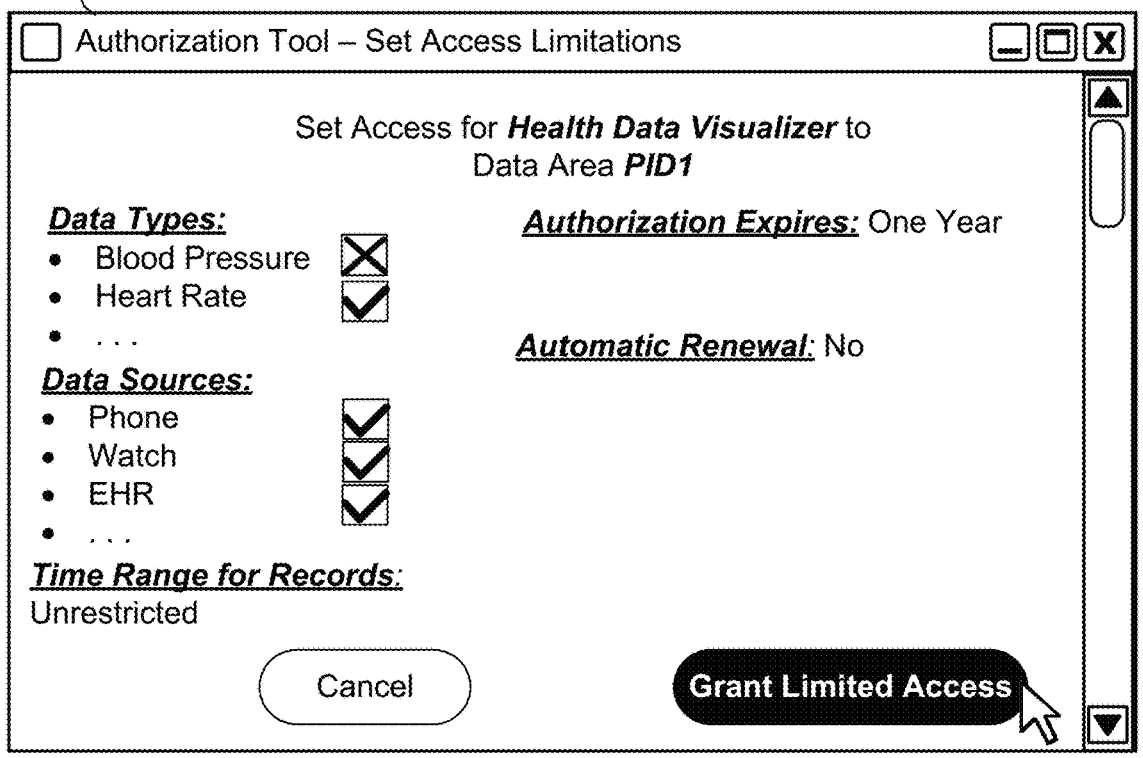

FIG. 3E shows a user interface 340 providing controls that enable the user to customize the authorization that the user grants to the application. In this case, the user can select from among the different data types and data sources represented in the health data of the user's data area. The user grants access to heart rate data but denies access to blood pressure data, and grants access to data from all data sources. The user sets an expiration for the authorization (e.g., in one year), and sets that the authorization does not automatically renew. The user has the option to limit the time range of records that are accessible, but the user declines to do so.

When the user is satisfied with the authorizations, the user selects to proceed and grant limited access to the "Health Data Visualizer" application. In response, the authorization tool 180 communicates with the computer system 110 to generate an access token for the application that will grant access to the data area PID1, subject to the limitations the user set. The authorization tool 180 or the computer system 110 provides the access token to the application, so the application can use the access token to access the user's health data.

Figure 3F:
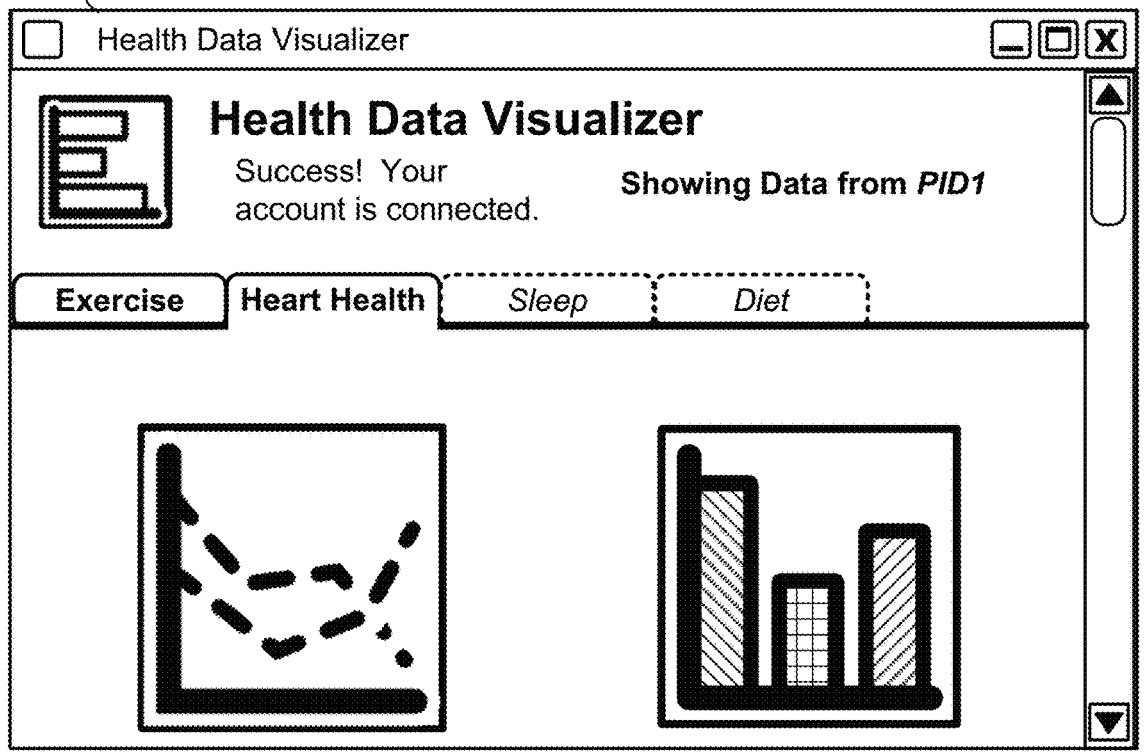

FIG. 3F shows a user interface 350 that shows the application after receiving the access token and populating information from the data area that the user authorized.

The process shown in FIGS. 3A-3F can be used to authorize any of various types of applications or even individuals to access data areas. For example, the same process can be used to enroll a user in a health research study, e.g., (1) receive one or more data areas that the user is willing to contribute, (2) show a customized indication of the value the study can provide to the user and a customized indication of what the user may be required to perform as part of the study, (3) set the appropriate authorization and limitations on access to data areas, (4) and provide the research study access to the user's data and provide the user access to the research study.

Figure 4:
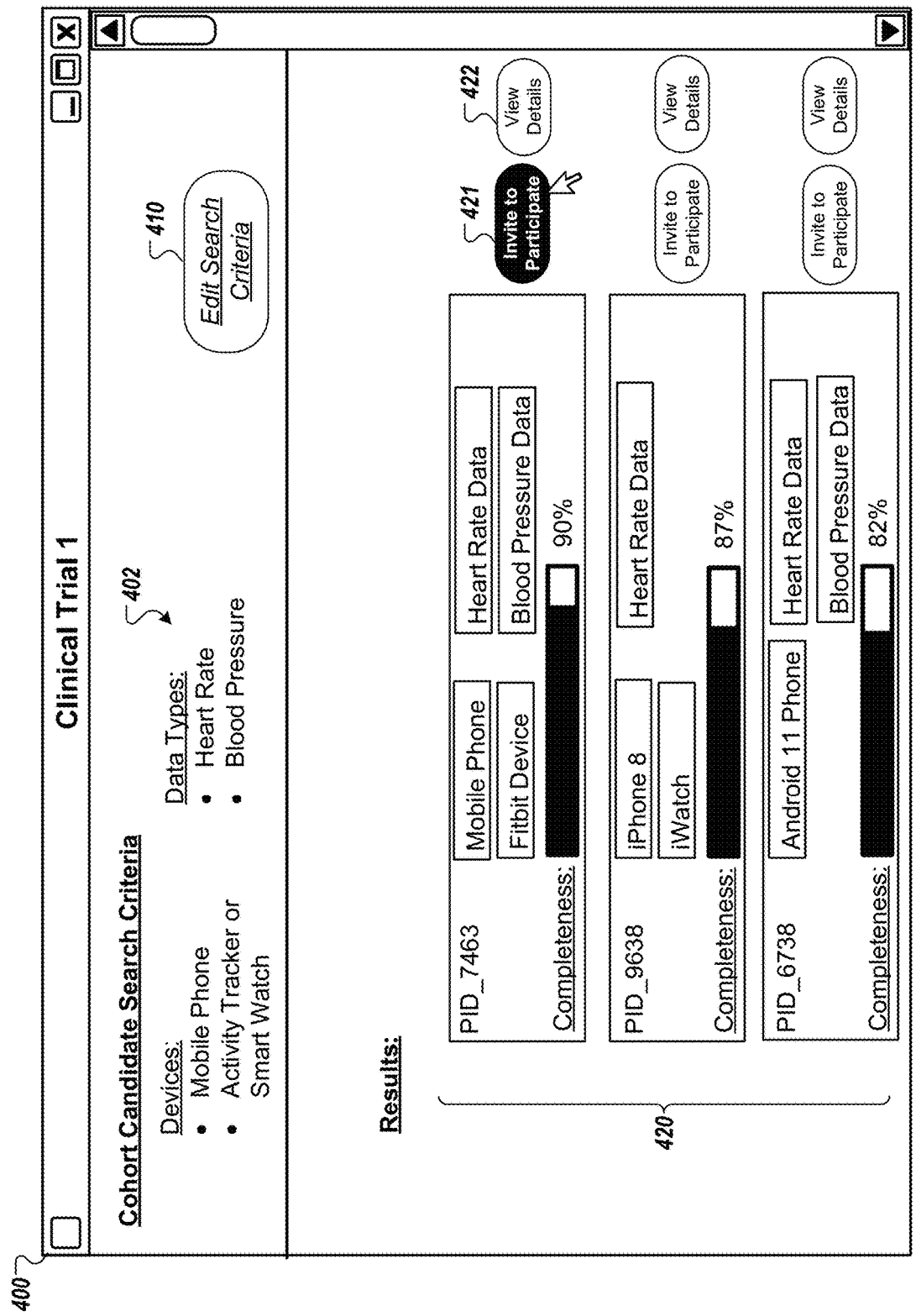
FIG. 4 is a diagram showing an example of a user interface for evaluating candidates for a clinical trial.

FIG. 4A shows an example of a user interface 400 for using metadata about data areas to search for cohort candidates. The user interface 400 shows search criteria 402 that a researcher set to indicate the types of participants or data areas the researcher would like to find. In this example, the researcher is interested in finding candidates that have a mobile phone and activity tracker or smart watch, and which have data collected for heart rate and blood pressure. The interface 400 includes a control 410 enabling the user to edit the search criteria 402.

Based on the search criteria 402, the computer system 110 has run a search across the set of data lakes 114a-114n or data areas in the system, using the metadata 115a-115n that each makes available. Individuals 102a-102n can keep their health data private while making some general information about the types and sources of data available, even while keeping the identities associated with the data areas hidden.

The interface 400 shows search results 420 showing the data areas that the computer system 110 determined, based on the contents of the respective metadata for the data areas, to best fit the search criteria 402. For each result, the computer system 110 indicates which requirements are present or which are absent (e.g., whether or not a given data area indicates the participant has a mobile phone). The computer system 110 also indicates a score, such as a level of completeness with respect to the search criteria 402.

Along with the results 420, the interface 400 provides controls for the researcher to act on the results 420. For example, the control 420 enables the researcher to invite the corresponding candidate (e.g., the one whose data is in data area PID_7463) to join the research study. The control 422 enables the researcher to view details about the data area, such as a more complete view of the metadata describing the data area. As a result, the researcher can easily identify data areas that provide the data types and data sources that are needed in the study, and invite them to participate.

Figure 5:
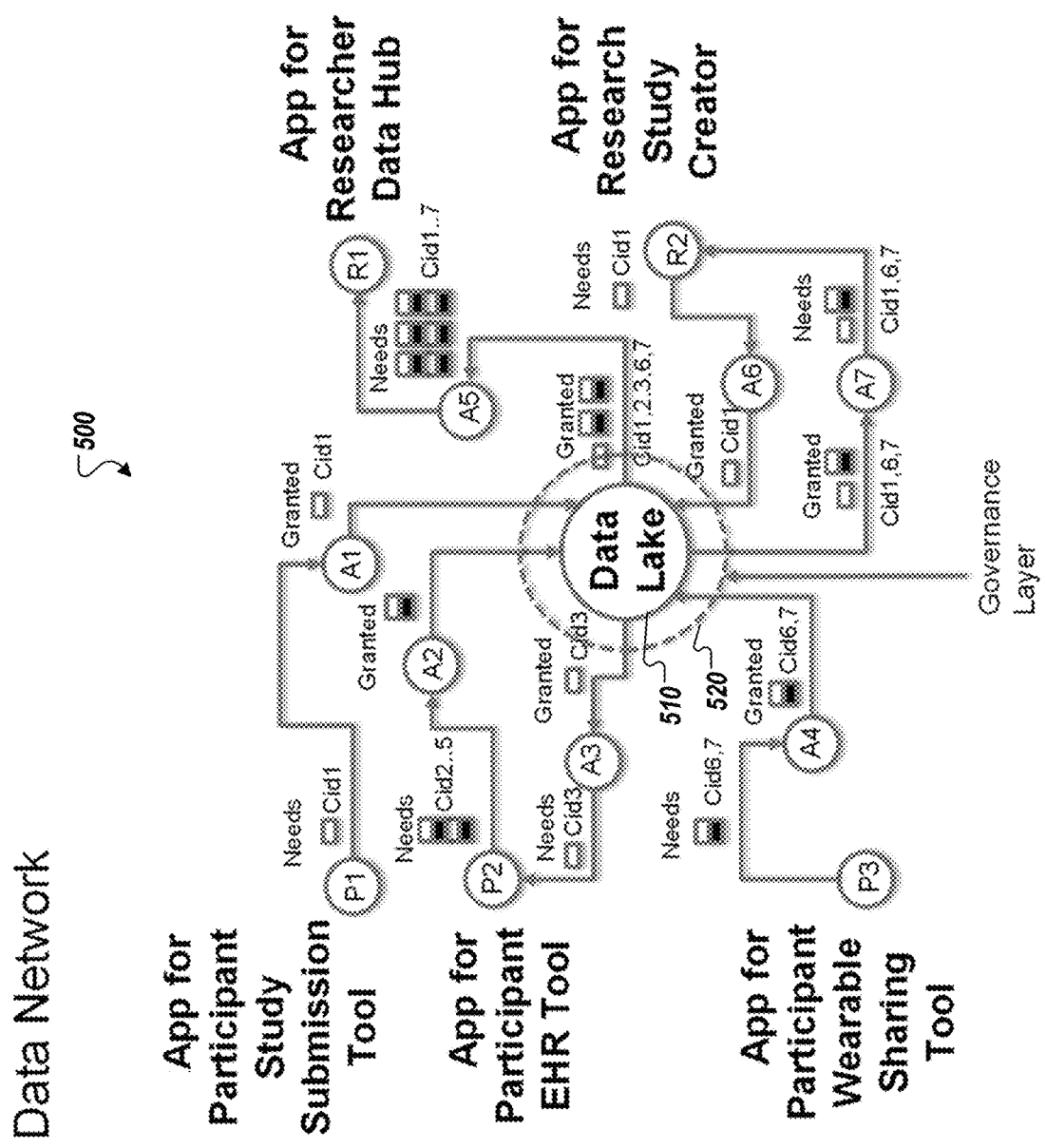

FIG. 5 shows an example of a data network 500 and interactions with a data lake or data area. In the network described there are applications that are participant-facing and applications that are researcher-facing. The applications connect at varying nodes the centralized network and data lake, with the computer system 110 providing central governance to approve authorization requests and data access needs for writing or reading records.

The data lake 510 represents a single data storage area for an individual. the governance layer 520 represents the functionality provided by the computer system 110 to enforce access control policies set by the user. This requires applications to demonstrate authorization for access using valid access tokens, and the governance layer 520 also limits the scope of access to the permissions and types of data the tokens permit.

There are three participant-facing applications, labeled P1, P2, and P3. P1 is an application for the user to participate in a research study and submit data (e.g., sensor data, survey responses, etc.). P2 is an application for the participant to access and view EHR data, for example through the user's own physician separate from the research study. P3 is an application for the participant to view and share There are also two researcher facing applications, labeled R1 and R2. R1 is an application for a researcher data hub, such as an application that the researcher uses to manage the research study, view the status of the research study, and access the collected data for the study. R2 is an application used by the researcher (or another researcher) to create a study and recruit participants.

The elements A1 through A7 shown different interactions of the applications P1-P3, R1-R2 with the data lake 510, as mediated by the governance layer 520. Each interaction can take place through an API call, using an identifier for the data lake 510 and an access token demonstrating authorization of the calling application to perform access. The arrows indicate whether data is read or written. For example, interactions A1, A2, A4, and A6 involve writing data to the data lake 510, while interactions A3, A5, and A7 involve reading data from the data lake 510.

The various interactions A1-A7 involve certain types of data, which indicated using a predetermine set of classifications, labeled CID1 through CID7. These labels represent identifiers for particular types of data, corresponding to a predetermined shared set of classifications, such as a taxonomy of data types as discussed further below. For example, CID may represent the classification of heart rate data, CID2 may represent the classification of exercise data, and so on. Through the governance layer 520, the computer system 110 can enforce the user's limits on data access. For example, although the application R1 requested access to data for classifications CID1-CID7, the governance layer only permitted the application R1 to receive data for CID1, CID2, CID3, CID6, and CID7. The governance layer 520 blocked access to data for CID4 and CID5 which the application's token did not authorize.

Access for writing or reading may not necessarily require full access to a data lake or data area, and some applications can operate with only partial or no access. Partial access may be given when a participant does not want to share all of the classifiers that represent the totality of the data that they can share, but rather they can withhold and provide some but not all to a given application whose function may be share with a downstream researcher. In addition, the notion of no access may be applicable when only public research information (e.g., non-encrypted, non-identifiable) is communicated. For instance, if the participant's data area address is known, then the database would have metadata available, e.g., information related to the data classifiers, that the participant can provide to researchers. This list of classifiers can be used by researchers to determine what data is already available to build a study. It can also be used by participants who want to know which studies are interested in their data. If some studies offer incentive models, then it can help the participant understand the amount of value that is placed on their data for participating in the study before they join, where value may be a result of a detailed insight, report, financial gain, or some other return of value (ROV) to the participant.

FIG. 6 is a table 600 that describes examples of data classifiers that can be provided as part of a standardized taxonomy of the various data categories. By defining data types and data categories and standardizing them, the system enhances interoperability among different applications and systems, which can then use the same, shared labels and identifiers to refer to the same types of data. Each category can be subdivided into sub-categories (not shown) to drill into more specific data types. These classifiers or classifications can publically reveal the nature of data on the centralized network, so that researchers can better help participants understand value of participation in a study and researchers understand the availability of potential study participants. This information can be leveraged in the provision and use of metadata for data storage areas, as discussed above and further below with respect to FIGS. 10 and 11.

The table 600 includes a "data" column 610 that indicates a description of the data type, a "data classifier" column 620 that provides a text indication of the data type, a "value type" column 630 that specifies the data format for the classifier, and a "coded value" column 640 that specifies the actual value that can be stored to indicated the data type. Each row indicates a different category or classification of data and the values (which can be in various forms as shown, a text data classifier label or a coded value) used as an identifier for that category or classification.

Figure 7:
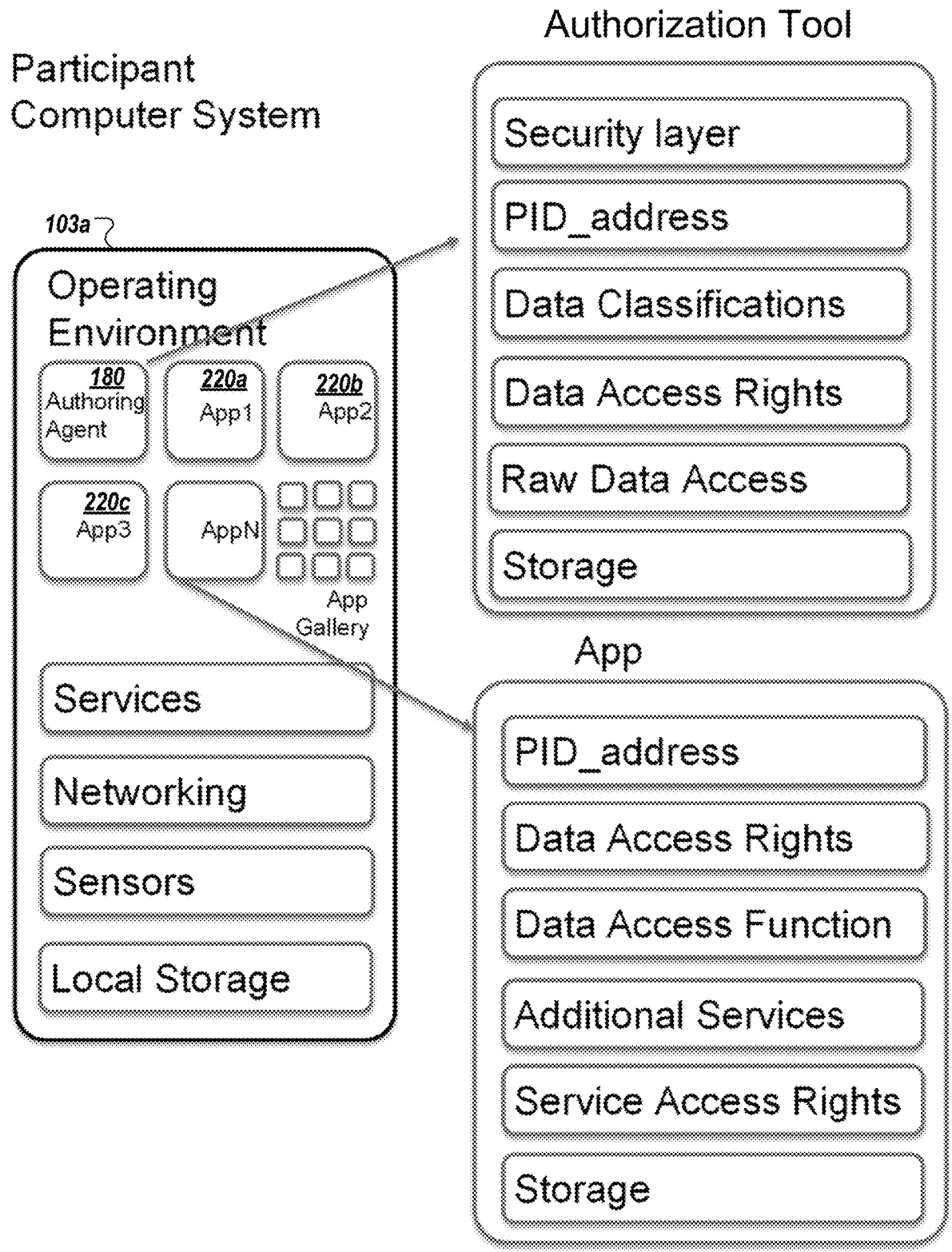

FIG. 7 shows an example of an operating environment for a participant computing system. As described above, there are multiple applications 130, and a gallery 184 of applications that can be accessed. An authorization tool 180, 183 or agent is also available. Only one of these may exist on a given environment and the participant may have several environments which constitute the multiple applications 130 shown at one time or over a period of time. Each operating environment would have a set of services and storage. However, not all would have the networking to an Internet and may only be accessed using USB, near-field communication, Bluetooth or some other non-Internet personal communication technology. Sensors are also optional components that may allow access to additional data for storage on the device that could potentially be shared through an application 130.

Figure 8:
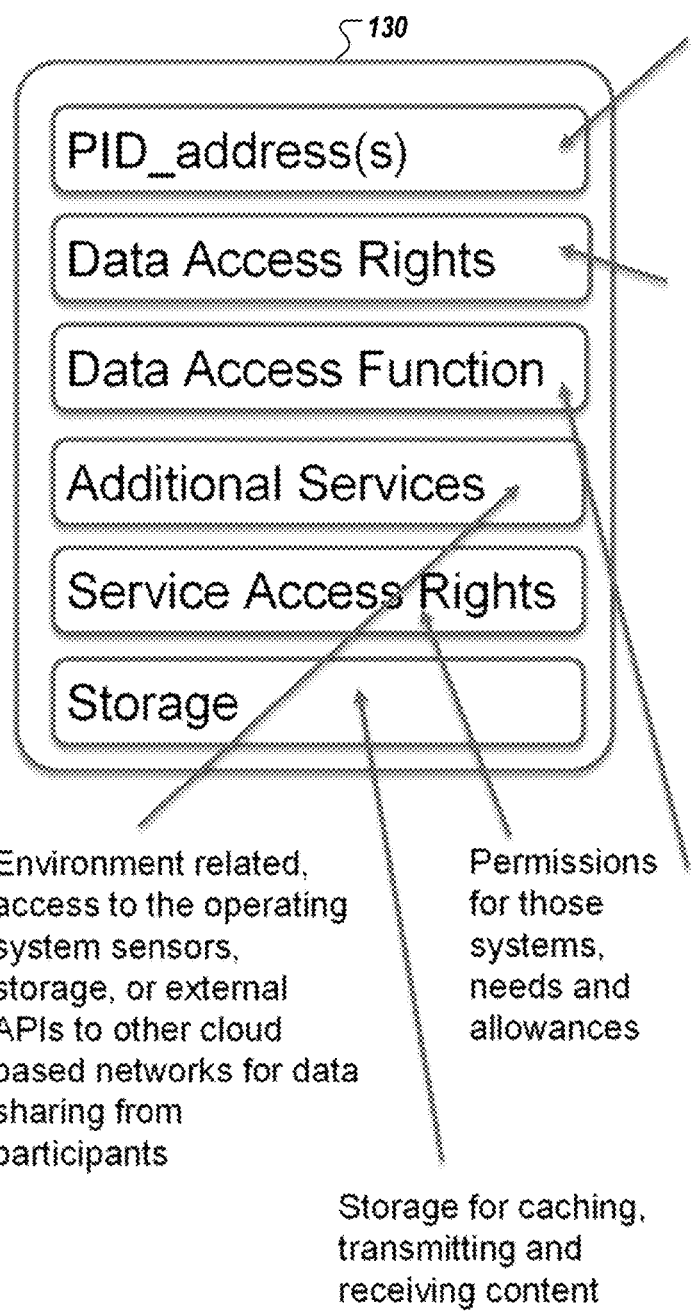

FIG. 8 shows an example of an application 130, such as any of applications 220a, 220b, 220c, 220d, discussed above. As described in the figure, there is the ability to use each application with minimal rights and access provided. As such, the PID_address (e.g., the unique identifier for a personal data storage area) is known by the participant and represents their account identification or address to their data on the centralized network and the resulting information in the data lake. The PID_address when provided to the application 130, allows a participant to understand the value of the application 130, what data access rights are required, what the function of the application is, and services/service access rights are needed including any device-based storage required to provide its overall function.

Applications 130 do not necessarily need a participant ID when considered for researchers, instead the ID functions as a practice or institution ID that associate study related protocols and data access needs from potential prospects. In addition, it allows the ability to a researcher to reverse lookup participants based on their classifiers which are de-identified to allow researchers to understand the potential data available, prior to deployment.

Figure 9:
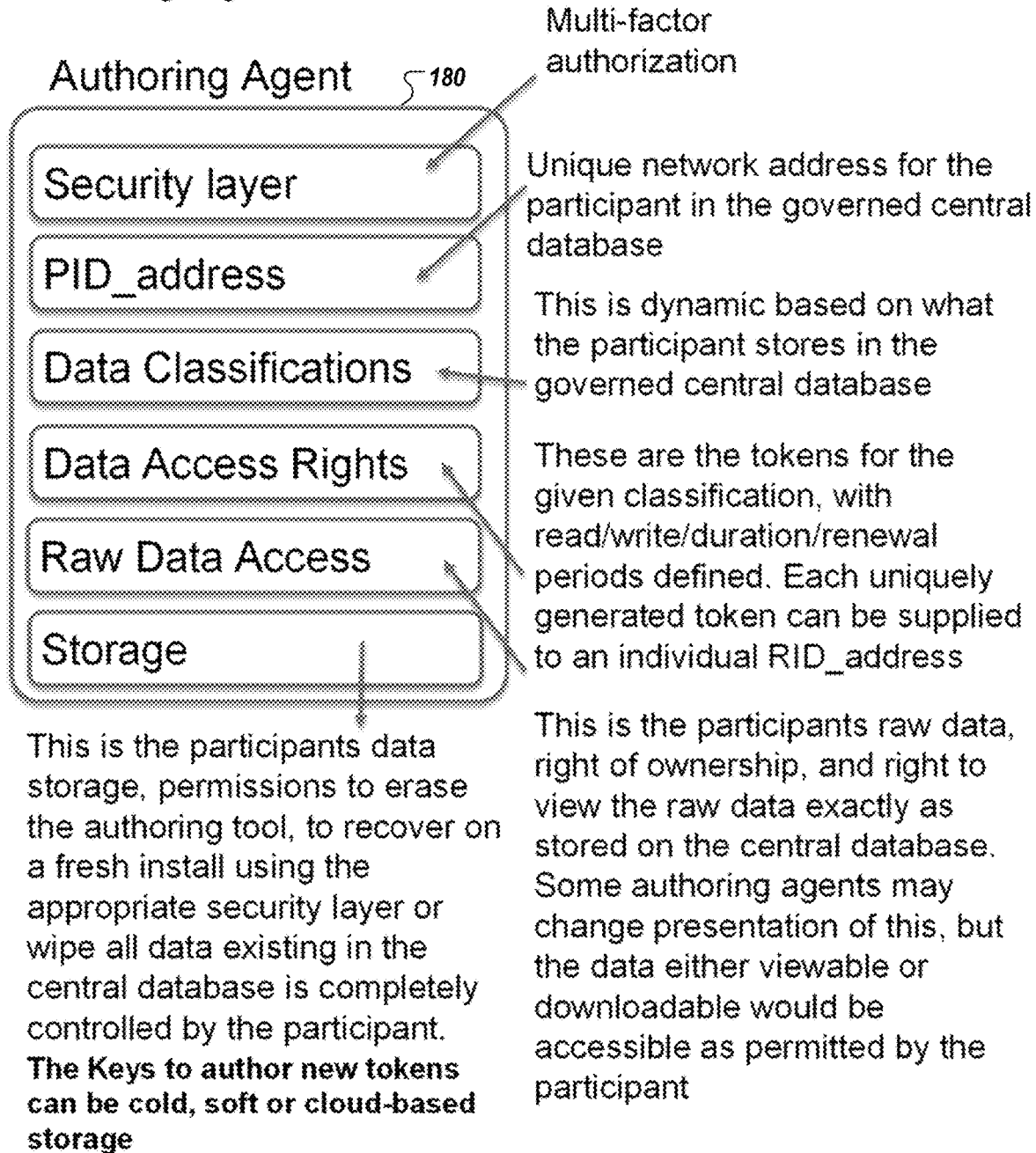

FIG. 9 describes an example of the authorization tool 180, 183. It can include a security layer, a participant identification address (PID_address), data classifications (similar to what is shown in Table 1), data access rights (these are licensing contracts that disclose tokens for use and continued use/access to data, along with renewal periods), raw data access (right to ownership for all data that is connected to the PID_address), and the storage of the data associated with the PID_address.

A type of authoring agent or authorization tool 180 is also provided to the research institutions when registering as a study on the centralized network. It allows the researcher to collaborate with other researchers, generate protocols and deploy studies to the centralized network for access by participants. As governing agent however, this is typically cloud-based (although it is not required), in order to provide a level of support to researchers when study access keys are lost, such that entire datasets are not left unattended or unmanaged in the centralized network and to participants that would upstream be expecting some value or response when researchers are locked out.

The computer system 110 can track the characteristics of the data stored in each data storage area. This can include tracking the types and amounts of data that are stored in the data storage area. As a result, the system can provide a user interface to the user that provides a summary or overview of what is stored in the data area. For example, the interface can provide a list of types of data present (e.g., heart rate measures and step count) and the amount of records (e.g., 312 measurements). The summary can also provide other information such as the span of time (e.g., measurements over 2 years for heart rate, and 1 year for step count), the source of the data (e.g., a fitness tracker device, or an application on a phone), information about the content or values of the data (e.g., resting heart rate averaged 68 beats per minute over the last week, and ranged from 62 to 81 beats per minute over that period), and so on. The information can be provided for the data area as a whole, for individual types of data or individual data sources, or for other subsets or aggregations of the data within the data area (e.g., by day, month, and/or year; by location of the user when the data was collected; by application type or category; etc.). The interface can be interactive so that a user that interacts with a data element or statistic displayed is shown an expanded view with the underlying data. For example, a user interacting with an indication that 312 heart rate measurements are stored can be shown a list of those measurements, in a table showing dates, time of data, measurement values recorded, device or application that provided the measurement, and so on.

The system can log events for each data storage area, including data read, data written, data modified, accesses and attempted accesses to the data storage area, and so on. With each event, the system can store an indication of the application, device, user, or other requester that is involved. For example, the different events and level of usage can be linked to different authorizations that the user has granted. The system can use this information to provide an interface that explains how the data storage area has been used. This can give a user information to better determine whether to continue or end access by different applications. For example, the interface can show that an application for a fitness tracker application has been providing daily step count records into the data storage area, demonstrating to the user that the application is operating properly. The interface may also show that another application has not accessed the data storage area for more than a year, and the system can present a control enabling the user to rescind access authorization for the application that is not using the access. The system can also use the tracking data to detect when a new application attempts to access the data storage area, or when the access pattern of an application changes. For example, for security, if the fitness tracker application changes its pattern of adding daily records and instead begins attempting to read new types of data that it did not contribute, the system may block the access, notify the user, and ask the user whether this new type of activity should be permitted.

The system 110 can track and use other types of information about the data storage areas. For example, for each of the data storage areas, the system 110 can track which authorizations have been granted, including which are currently active, and which have expired or have been revoked. This information can be provided to a user in a management interface so the user can see at any time which applications or parties have access to data in the data storage area. The interface can indicate the various parameters for each authorization, e.g., the types of access allowed (e.g., read, write, modify, and other permissions), the types of data allowed to be accessed (e.g., heart rate data, step count data, sleep data, etc.), amount of accesses or frequency of access permitted, and so on. Along with the information about current and former authorizations, the system can provide interactive user interface controls (e.g., buttons, checkboxes, etc.) that enable the user to alter the authorizations for access to the data area, such as to extend an authorization for a longer time, to cancel or rescind a currently-active authorization, to renew or continue a former authorization, to change an expiration date of an authorization, to change access type permissions or change the types of data that can be accessed, and so on. The system can track and show in the interface requests for authorization to access the data area, such as pending requests from applications that have not been granted or requests that have been denied, with controls for the user to act on those requests by granting or denying access and setting a desired level or type of access permitted.

The computer system 110 can also track and display to a user information about the metadata for a data storage area of the user. In the same manner that the computer system 110 tracks and shows the user information about data present in the data storage area, the authorizations for the data storage area, and the access history for the data storage area, the computer system 110 can do the same for the metadata for the data storage area. For example, various user interfaces can provide overview and detailed information about which types of metadata the user has authorized applications to access, what the current values of those metadata items are, and how applications have actually accessed or requested metadata for the data storage area. Along with this historical and status information about metadata for the data storage area, the system can provide interactive controls that enable a user to select to change what metadata is provided (e.g., select types of metadata to include or exclude), change the level of detail or precision of the metadata that is provided, change the set or types of applications that are authorized to obtain metadata, and otherwise manage the metadata that can be obtained through the API.

Figure 10:
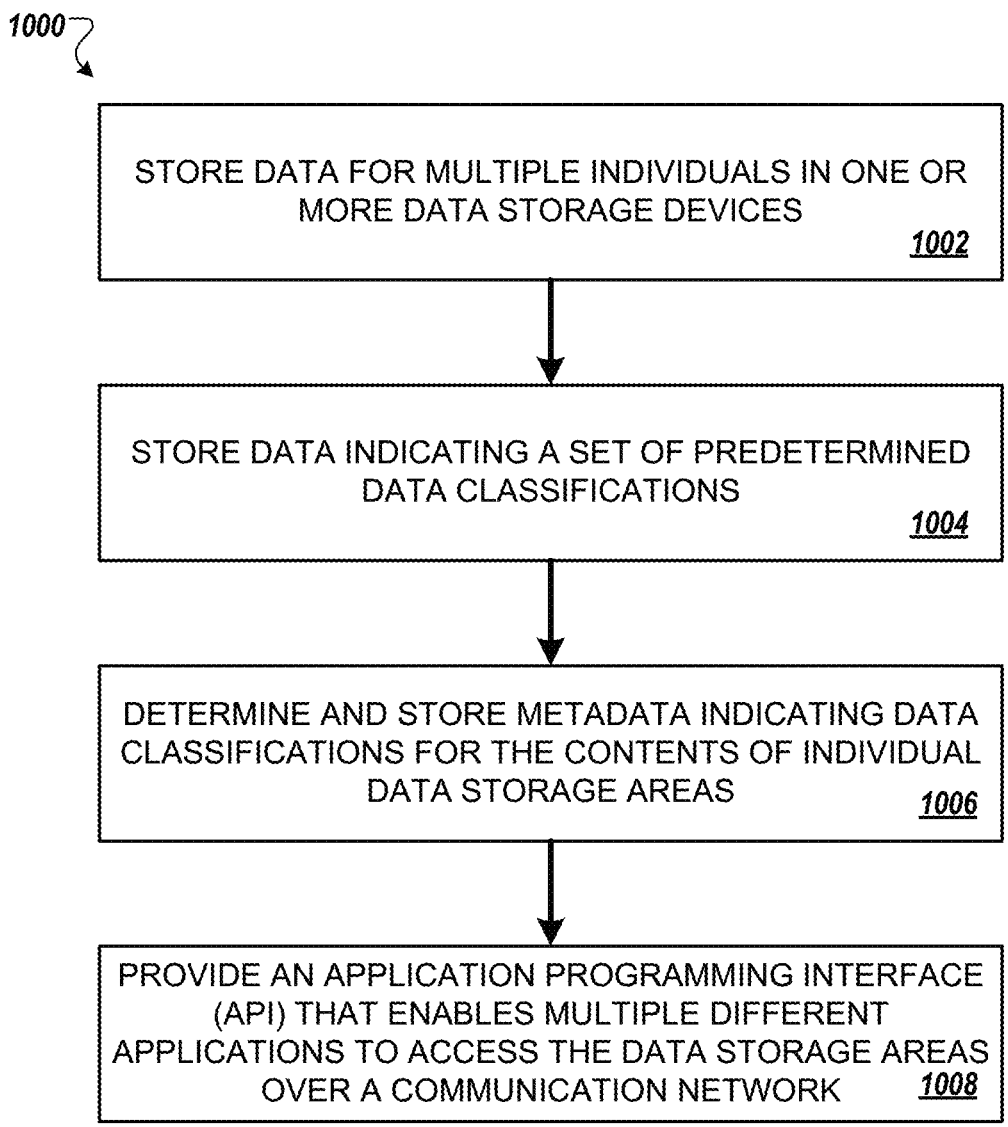
FIGS. 10-11 are flow diagrams that illustrate examples of processes to facilitate data access in a decentralized application ecosystem.

FIG. 10 is a flow diagram that describes a process 1000 for storing and providing data with access control to applications in a decentralized application ecosystem. As discussed above, a centralized server system manages many different data areas for different individuals, and selectively provides access to the data areas to various applications which can be developed and provided by many different third parties. The process 1000 can be performed by one or more computers, such as the computer system 110.

The process 1000 emphasizes how the computer system 110 can generate and provide different types of access to information from the data storage areas. For example, as authorized by user privacy settings, the computer system 110 can store and provide metadata indicating data types or classifications of the data available in private, encrypted data areas.

Actual access to the data areas, e.g., to read or write data, can be restricted using user-defined permissions and authorizations. The authorization that enables an application to access a data storage area can be represented by an access token that proves that an application has authority to access a particular data storage area.

In addition, the computer system 110 enables applications to access metadata about the contents of data storage areas without requiring an access token to be provided. While blocking access to the underlying content of a data storage area, the computer system 110 can still provide information about the categories or types of data that are present in a data storage area. For example, a user may have a health data storage area that includes Fitbit step counts and heart rate measurements. Access to the values of the step count measurements and heart rate measurements are restricted to be accessible only to applications providing a valid access token for the data storage area. However, metadata about the data storage area can be accessible without an access token, potentially to all applications or to a more limited subset of applications according to the user's settings. The metadata can indicate various characteristics of the information stored in the data storage area, such as that step count data is included, that heart rate measurements are included, and that the source of the data is a wearable fitness tracker device. If the user settings permit, other metadata can be provided, such as an amount of data provided (e.g., more than 100 daily step count measurements), a recency of the data (e.g., most recent value measured within a week), whether the data storage area is configured to receive repeated, ongoing data for certain types of data, and so on.

The metadata enables the computer system 110 to benefit users and application providers. In the context of health research, the metadata can indicate types of health data that a user has already collected, which can be used to determine if the user is a good candidate to participate in a research study. For example, the metadata can indicate types of data that were previously collected for the user, which the research study may be able to use and avoid duplicative collection of the same information. Even if the study will involve new or ongoing data of the same type of data, the presence of data of the type a study needs or collection with techniques used in the study indicates that the user has familiarity with or past success in collecting those types of data. The computer system 110 can use this as an indicator of high likelihood of success of that user will comply with the requirements of the health research study to collect that type of data. In addition, the metadata can indicate data sources that the user has available (e.g., a mobile phone, a particular model of fitness tracker device, EHR, etc.), and the ability to obtain data from those sources (e.g., a user having a phone and a fitness tracker device) may be a requirement for eligibility to participate in the study. As a result, the computer system 110 can use the metadata to determine whether a user meets eligibility requirements, as well as to rank, prioritize, and select the participants for a health research study.

As discussed further below, when a user enrolls in a study or participates in a study, the data collection actions of software for the health research study can be customized based on the data storage area to rely on the data storage area for previously collected data as well as future data to be collected in the data storage area. This often reduces the amount of new data collection that needs to be initiated, customizing the data collection performed for the user to avoid duplicative collection of data. This significantly improves efficiency by reducing power consumption, network bandwidth consumption, and computing overhead, which can be particularly important when performing long-term, on-going monitoring using battery-powered mobile devices and wearable devices.

The process 1000 includes storing, by the one or more computers, data for multiple individuals in one or more data storage devices (1002). The data for each individual can be stored in a different logical data storage area. The data storage areas are respectively assigned unique identifiers, and different data storage areas have contents encrypted using different encryption keys (e.g., each data storage area may be encrypted with its own encryption key, which is different from the encryption keys of most or all of the other data storage areas). As discussed above, the data storage areas can be de-identified, and can have customized access settings set by each user. The data storage areas can be owned and controlled by the individual users, and the data storage areas can store various types of data, including health data that describes physiology, behavior, mental health, and other information about a user's health conditions or state of health.

In some implementations, the data stored for the individuals in data storage areas is health data that describes health conditions or health characteristics of the individuals. At least some of the data storage areas can be data storage areas storing health data generated for (e.g., during and as part of) a health research study in which the individual is a participant.

In some implementations, the data storage areas can each be implemented using an append-only ledger. This can preserve the underlying data for security purposes as well as to facilitate capturing the ongoing, longitudinal health data that is generated over time, whether in daily life or as part of a health research study. If errors need to be corrected, new records can be added with an instruction to be used in place of the previous record, but the series of transactions is preserved and the earlier values can still be examined.

The different data storage areas can be de-identified. In some implementations, public information does not link a data storage area to any user identity, so that without a key or access token for the data storage area an identity of the user whose health data is stored cannot be determined. This can include not even linking the data storage area to any user identity or user identifier, even an identifier for which the user's name or personal information is obscured. In some cases, the computer system 110 does not even track or maintain a record of which data storage areas correspond to the same user.

The process 1000 includes storing, by the one or more computers, data indicating a set of predetermined data classifications (1004). The set of data classifications can be a set that is the source from which metadata values are selected. In other words, the system can enumerate and store data indicating the group of possible classification values to be used in metadata. Then, when generating metadata, the system can select from the set to assign the data classifications that are appropriate.

The data classifications are configured to be used to provide and assess metadata, and so in some implementations they omit information about the underlying health data characteristics of the individual. For example, a data storage area being assigned a particular data classification may signify that body weight data for user is present in the data storage area, but the classification would not indicate a weight value for the user. Typically, the data classifications do not provide any indication about the underlying data, not even a low-precision indication of measurement values or other content. In other words, the data classification(s) for body weight would not indicate that the weight is in one of various ranges, would not indicate whether the weight is healthy or not, and would not indicate whether the weight satisfies a threshold. Instead, the data classifications would simply indicate that data about body weight exists in the data storage area. Some other types of data classifications may indicate information about the stored records or the data collection process (e.g., how recently the weight data was generated, how many measurements are stored, etc.), but would also generally omit any indication of the measurement results or underlying values for the data.

As an example, data classifications can be defined for the various types or categories of health data that are recognized in the system. As a result, data classifications can be defined to represent "sleep data," "diet data," "body weight data," "genomics data," "physical activity data," and other types of health data. These data classifications can each represent a different type of property, attribute, or characteristic measured. For each of the categories of health data, a unique identifier can be specified as a data classification signifying that this type of data is present. The example of FIG. 6 shows a table of different types of health data and corresponding data classifications expressed as identifiers or classifier values. When generating metadata for a data storage area, the system can identify the types of data present in the data storage area, use the stored table or reference data to select the data classifications (e.g., the data classification identifiers) for the types of data determined to be in the data storage area, and generate the metadata to indicate the data classifications (e.g., by including the selected data classification identifiers).

The data classifications can indicate any of different aspects or dimensions of the data in the data storage area. For example, data classifications can indicate (1) different types of health data present (e.g., resting heart rate measurements, respiration rate measurements, sleep tracking data, height, weight, diet information, etc.), such as indicating the semantic meaning of the data, (2) different sources of health data (e.g., survey data, EHR, a category or type of device or sensor, an ecological momentary assessment (EMA), etc.), (3) a level of quality of health data (e.g., a level of precision, accuracy, consistency, or completeness; whether the data meets one or more validation rules; etc.), (4) timing information (e.g., a time or range of time in which a measurement or input was provided; how recently the data was updated or added to; a duration of time or span over which records are present; etc.), (5) data collection parameters or processes used to generate the data, (6) characteristics of the data collection pattern, including a status whether data collection is ongoing (e.g., continuing), and more.

The system may define and store a set of data classifications for each of the different aspects that can be expressed in metadata. For example, for metadata indicating type of data, data classifications can be defined for the different categories of health data. For metadata to indicate data source, the data classifications can respectively indicate different sources (e.g., EHR, user input, device sensor, etc.) and/or different types of devices (e.g., phones, activity trackers, glucometer, etc.). For level of quality, the data classifications can indicate high quality, medium quality, and low quality, or may have other scores or labels. For timing information, the data classifications can indicate any of various different characteristics using status with respect to different predetermined ranges or time periods, e.g., updated in the last day, updated in the last week, updated in the last month, updated more than one year ago, includes data spanning more than a week (or month, or year, etc.), includes data spanning less than a week, and so on.

Each data classification can be assigned a code or identifier that is used consistently in the system across applications and data areas to refer to that data classification. The system can include the code or identifier for a data classification in a set of metadata for a data area to indicate that the data classification applies to the contents of the data area. In some cases, multiple groups of data classification identifiers are provided. For example, different codes can be provided to signal different types of health data stored, and those codes can each be grouped with other data classification codes for other properties (e.g., timing, data quality level, source, etc.). For example, a set of metadata may include a first data classification label to indicate that heart rate data is included, and additional associated data classification labels may indicate that the data was updated in the last week and the source of the data was a fitness tracker device. Similar groupings of data classification codes can be provided for each of different types of data identified in the data area.

The system can store rules or criteria for each data classification, enabling the system to judge whether a record meets the requirements for that data classification to be applicable. For example, for a "body temperature data" data classification, the system can store criteria to identify results generated by thermometers, values in a certain range (e.g., 95° F. to 110° F.), values of ° C. or ° F., keywords or labels indicating body temperature, and so on. With these references, the system can assess the data present in a storage area to determine whether the data has sufficient markers or indicators to show that body temperature data is present. In a similar manner, the system can store criteria to determine whether each of the other predetermined classifications are present. For structured data sets, the system may use the table and column structure of a data set or other labels present to determine whether a data classification is applicable. For example, the presence of measurement values in a column labeled "temperature data" sourced from EHR can be used to determine that temperature data is present. To facilitate this analysis, the system can store lookup tables and translation tables to map different codes or labels used in EHR systems, insurance billing, hospitals and medical offices, and so on to the different data classifications.

The data indicating the set of predetermined data classifications can be expressed in a table, list, or other data structure that provides a taxonomy, e.g., a system of classifying the types of data, or for classifying according to other metadata characteristics. The classifications can be set up in a hierarchy that indicates relationships among the data classifications and different levels of detail for different data types. For example, a high-level set of classifications can be set, such as "behavior data," "physiological data," "mental health data," and so on. For each of these top-level categories, one or more levels of sub-categories can be defined. For example, within the classification of "behavior data," there may be a next tier of sub-categories such as "sleep data," "physical activity data," "diet and nutrition data," and so on. Within these sub-categories there can be classifications representing additional levels of detail, such as sleep data having further sub-classifications for "sleep duration data," "sleep quality data," etc.; with physical activity data having sub-classifications for "step count data," "exercise duration data," etc.; and so on. As another example, within the broad classification of "physiological data," a first level of sub-classifications may include items such as "body weight data," "body temperature data," "heart data," "respiratory data," and so on. Further sub-classifications can be provided. There may be any appropriate number of levels of data classifications (which can refer to top-level classifications and sub-classifications).

In some implementations, some data classifications can be defined in the hierarchy for specific types of measurements, such as "daily step count," "average daily resting heart rate," "daily peak heart rate," "systolic blood pressure," and so on. Structured in this manner, the presence of one specific type of measurement can indicate that each of the more general classifications are appropriate. For example, a resting heart rate measurement can be used to indicate that "heart rate data" is present, as well as the broader classifications for "heart data" and "physiological data." As another example, tables or mapping data can associate different measurement types with different data classifications.

Defining a standardized set of data classifications in this way (whether for the type of data or other metadata characteristics) can facilitate the interoperability of many different third-party applications, as well as the use of data from many third-party data sources that may natively use different data formats and conventions.

The standardized data classifications also facilitate greater user control over which types of data and metadata are provided. For example, when a user sets the authorization of which data an application can access, the user can be shown a visual representation of the hierarchy (e.g., as a tree structure) with controls to set permissions (e.g., grant access, deny access, or grant limited or conditional access) for individual elements or branches within the hierarchy. Also, the user can adjust metadata properties. The system can again provide a user an interface to select that different items or branches of the hierarchy, and to specify for the selected items whether metadata (provided generally or for specific groups or types of applications) can or cannot be indicate whether those items or characteristics are present. As an example, a user may enter settings to allow metadata to include data classifications for physiological data and its sub-categories. The user may enter settings that block other branches of the hierarchy from being described in metadata, e.g., blocking metadata from including data classifications that would indicate the presence of behavior data or mental health data. Similarly, the user may set the metadata to allow or block metadata from providing different levels of detail about the contents of a data area. For example, the user may enter settings that allow the top-level classifications and first sub-classifications to be indicated in metadata, but lower-level classifications are not allowed to be shown. The computer system 110 stores these user-specified settings and generates and provides metadata accordingly, to provide only the metadata classifications that the user has authorized.

The process 1000 includes determining and storing metadata indicating data classifications for the contents of individual data storage areas (1006). The computer system 110 can maintain a set of stored metadata for each data storage area. The system can update this set periodically or in response to changes in the contents of the data storage area, such as the addition of a new record by an application. This ensures that accurate metadata is present when requested, and enables the system to handle a high volume of requests for metadata with low latency and low computation complexity (e.g., a simple look-up of the stored values). It has the benefit of minimizing the number of times that data in the data storage needs to be decrypted and analyzed, since incremental updates can be made to the metadata based on the plain-text information added to a data storage area. In other implementations, the computer system 110 generates metadata dynamically in response to requests for metadata. This reduces the ongoing computational load to maintain and store metadata for large numbers of data storage areas, but may result in higher latency in responding to requests for metadata.

When generating metadata for a data storage area, the computer system 110 may include metadata for linked data storage areas. For example, if a first data storage area includes the access token to provide access to a second data storage area and third data storage area, the metadata for the first data storage area can include combined data classifications for the first, second, and third data storage area. This reflects that obtaining access to the first data storage area permits additional access to the other data storage areas. To respond to a request for metadata for the first data storage area, the computer system 110 can retrieve the respective metadata describing the separate contents of the first, second, and third data storage areas, combine the three sets of metadata, and provide the combined set of metadata in response to the request.

As an example, for each data storage area of at least some of the data storage areas, the computer system 110 can determine data classifications for data stored in an encrypted form in the data storage area. The data classifications can be selected from among the set of predetermined data classifications based on analysis of the contents of the data storage area. The computer system 110 can then store data indicating the determined data classifications for the data storage area in metadata associated with the data storage area (e.g., metadata 171 as discussed for FIG. 1C).

In some implementations, the system can detect, for a particular data storage area, a predetermined condition set as a trigger to refresh metadata for the particular data storage area. In response to detecting the predetermined condition, the system can update a set of data classifications for contents of the particular data storage area. The condition can be, for example, access to a data storage area, a request for metadata for the data storage area, data being written to the data storage area, the occurrence of a predetermined time or end of a time period, etc.

In some implementations, the system may generate metadata for a particular data storage area by: decrypting contents of the particular data storage area; classifying the contents of the particular data storage area to select data classifications from the predetermined data classifications that are applicable for the contents of the particular data storage area; and storing metadata for the particular data storage area that indicates the selected data classifications. Other types of data classifications can be determined by, for example, identifying the sources of data stored in the data storage area and identifying the data classification(s) representing those sources, determining a range of time spanned by records in the data storage area and identifying the data classification(s) that apply to the determined range of time, and so on.

As discussed above, the data classifications can be assigned to indicate various different properties of the data in a data storage area. The data classifications can indicate, for example, the types of data present, the sources of data present, timing of when the data was added or the times that the data represents, properties of data collection parameters or processes used, the pattern or rate that data has been added, levels of quality of the data, and more. The types of metadata determined can be limited or conditioned on user-specified settings that may allow or disallow different types of data to be indicated as present, or may allow or disallow certain other characteristics from being indicated in the metadata. Authorization may be granted or denied by the user for different levels of detail or for different portions of a hierarchy of data classifications.

As an example, the system can determine, for a particular data storage area, types of data present in the particular data storage area, and the system can store, for the particular data storage area, metadata that indicates the types of data determined to be present in the particular data storage area. These types of data can be at various levels of detail or for various dimensions (e.g., sensor data vs. survey response data; physiological data vs. behavior data; heart rate measurements, blood pressure measurements, step count measurements, etc.; data about exercise, sleep, diet, etc.; data about heart, lungs, kidneys, or other organ or body system). The data classifications can represent predetermined aspects of health (e.g., physiology, behavior, mental health, disease diagnosis, treatment, etc.) that the system determined to be described by the data stored in encrypted form in the particular data storage area. At least some of the data classifications determined to be applicable for the data storage area can represent predetermined types of measurements of physiology, behavior, or mental health. In some cases, the data classifications can indicate the presence of context data (e.g., geographical location, activity or task being performed, etc.) or environmental data (e.g., air quality, chemical exposure, air temperature, etc.).

The system can use any of various techniques to determine which data classifications are applicable to a data storage area. For example, the system can find existing metadata in the contents of the data storage area itself (e.g., a column header, keyword, label, etc.) and map that metadata to the corresponding data classifications. As another example, the system can examine data contents (e.g., record types and values in records), as well as the source of the records, and use the stored rules and data classification criteria to determine which data classifications apply. For structured data, records or items in the records may already be classified, although potentially with a different classification system. Once the system determines the types of data present in the data storage area, the system looks up the correct data classification codes or identifiers from the stored data, e.g., a table, list, taxonomy, hierarchy tree, etc. that specifies the codes and mappings of those codes to different data classifications. The metadata can indicate that a data classification is applicable through a list of data classification codes for the data classifications that are applicable. These codes can be grouped together in multiple different groups to represent properties of multiple different types of data (e.g., one group of codes for heart rate data and its source and timing, another group of codes for respiration data and its source and timing). The selected data classifications can be encoded in other ways. For example, the system can generate a one-hot vector that has a value for each of the potential classifications, with a "1" if the classification applies and a "0" if not.

In some implementations, at least some of the predetermined data classifications represent different sources of data. For a particular data storage area, the system can identify one or more sources of the data in the particular data storage area, and metadata that indicates the identified one or more sources.

In some implementations, at least some of the predetermined data classifications are data quality classifications that represent different levels of quality of data. For a particular data storage area, the system can determine a quality level classification for the data in the particular data storage area, the quality level classification being selected from among the predetermined set of data quality classifications. The system can metadata that indicates the data quality classification of the data in the particular data storage area. For example, for each data type or measurement, a set of thresholds or criteria can be set and stored by the system to determine the boundaries of different levels of quality, e.g., whether a minimum amount of records is needed to reach a "high" quality rating, a level of precision or number of significant digits needed for different quality levels, or whether the data from different consumer models of sensors or devices respectively provide high, medium, or low reliability outputs. As another example, self-reported data may be rated as lower quality than measurements recorded through automated sensors of devices. The data quality classifications can represent overall quality across multiple characteristics, or may represent different levels of specific characteristics such as precision, accuracy, consistency, or completeness.

The process 1000 includes providing, by the one or more computers, an application programming interface (API) that enables multiple different applications to access the data storage areas over a communication network (1008). The system is configured to provide access through the API to the data stored in an encrypted form in the data storage areas. In other words, the system can decrypt the values and provide them in a format so that an application can read and understand the uncrypted or plain text values stored in the encrypted area. The data can still be communicated in an encrypted or secured form (e.g., using secure socket layer (SSL) communication, etc.), but using a different encryption that the application has the key to decrypt. For example, the system enables applications to read or write health data in data storage areas through API calls when the applications demonstrate proper authorization. Access to the data is conditioned on applications providing authorization tokens corresponding to the data storage areas accessed for which the data is accessed. If an application attempts to read or write a sensor measurement result to a particular data storage area, for example, the system can verify that the API call is associated with an access token (e.g., a token provided with the API call, or a token used to start a current session of interactions, etc.) that is valid and demonstrates appropriate authorization for the requested type of access to the data storage area before the system performs the action requested. If the access token is valid and demonstrates authorization, the system carries out the requested operation; if not, the system does not carry out the requested operation and informs the requesting application that its authorization is insufficient.

In addition to the access-token-based access to the contents of the data storage area, the system is configured to provide access to certain types of metadata without requiring an access token. For example, the system is configured to provide access through the API to the data classifications in the metadata corresponding to the respective data storage areas. Access to the data classifications is not conditioned on applications providing authorization tokens corresponding to the data storage areas for which the data classifiers are accessed. In other words, if a user's metadata access settings permit it, an application can request and receive metadata for a data storage area without any access token required. The types allowed to be accessed may vary from one data storage area to another.

The technique of providing limited metadata without requiring prior authorization enables applications to determine whether a data storage area is relevant for the application (e.g., providing at least a type of data the application needs or can operate on), before receiving any explicit authorization. At the same time, the contents of the data— the values of measurements, diagnoses, treatment plans, and other health data—are not provided or indicated. The metadata can describe only that certain types of measurements are present, or that data from EHR or other sources is present, without revealing the actual details of the data. This metadata can enable applications to enhance and personalize the user experience for the user, before even obtaining access authorization for the user's data area.

In addition, the metadata enables researchers, or the computer system 110 acting on behalf of researchers, to better evaluate candidates for health research studies. For example, the computer system 110 can identify data storage areas that have a combination of data needed by a study (e.g., genomics data and exercise data for the last 5 years). The system can propose these data storage areas as potential candidates for a health research study, since the corresponding individuals have already collected significant types of data needed in the study. With this data already present, the research study can operate much more efficiently, without incurring the costs and delays that would be needed to re-gather that same data. In some cases, such as where significant amounts of prior medical history or behavior history is needed in a study, there may be not effective substitute for having the historical or baseline data when a person joins the study. For example, if a study intends to rely on the previous year of exercise data as a baseline, it is not feasible to monitor candidates for a year to generate the initial data needed to be eligible for the study, and doing so would delay participation in the study by a year. When metadata indicates that the correct types of data is present (and potentially other needed characteristics of the stored data are present, individuals can be enrolled or onboarded (e.g., brought into full participation, monitoring initiated, etc.) with minimal additional data collection needed, by relying on the data in the data storage area (and potentially other data storage areas of the user) to avoid redundant data collection operations.

The metadata also provides an indicator of the individual's likely level of compliance with the requirements (e.g., study protocol) of a research study. If the metadata indicates that the data storage area has collected certain types of data needed in the study, with a frequency or rate that is similar to that of the study, then it is likely that the user will be able to successfully continue those data collection actions as a participant in the study. Similarly, the metadata indicating sources of data or types of data can indicate that a user already has a device of a particular type (e.g., phone, activity tracker, glucometer, weight scale, etc.), which can indicate that the study would not need to provide devices of that type to the user. For studies with large numbers of participants, where devices cannot feasibly be provided to all participants, this metadata can enable the system to identify a candidate pool (e.g., set of data storage areas) that has the device(s) needed.

While authorization for individual data storage areas may not be needed to access metadata, applications may still need to demonstrate certain credentials to be able to access metadata. For example, the system may require applications to be registered with the system, be authenticated in the system when making requests, and may be required to hold at least a minimum level of trust or certification in the platform before the system will carry out requests to access metadata without an access token. These requirements can provide additional security and privacy in the system, to limit metadata access to legitimate entities that have demonstrated that they operate within the terms and conditions required to obtain this data.

The system can adjust or limit the metadata provided based on user-specified settings. Consistent with the goal of giving individuals control of how their data is accessed and used, the system can provide interfaces for users to specify which metadata can be provided and the circumstances or conditions in which it can be provided. In some implementations, the system stores, for a particular data storage area, a user-specified metadata access setting that governs access to metadata for the particular data storage area. The system receives a request through the API for data indicating data classifications for data stored in a particular data storage area. The system determines that access to the data classifications for the particular data storage area is permitted based on the user-specified metadata access setting. Based on determining that access to the data classifications for the particular storage area is permitted, the system provides a response to the request that identifies one or more data classifications for contents of the particular data storage area.

The metadata access settings can control any of various aspects of metadata generation and delivery. For example, settings can enable or disable sharing of metadata, for the data storage area as a whole or for specific data sets, types of data, sources of data, or other subsets of data. The settings can limit or set boundaries on which metadata can be indicated, and to which applications. For example, the settings can limit which sources of data, time ranges, types of data, data sets, etc. can have metadata provided. As an example, a user may select to allow metadata indicating that the presence of Fitbit exercise tracking data can be indicated in metadata, but the presence of data from a neurologist's office cannot. Beyond simply which metadata can be accessed and by which parties, the settings can specify which metadata is even generated and/or stored for that data storage area.

In some implementations, a user-specified metadata access setting provides a limit to the types of metadata or level of precision of metadata that can be provided for the particular data storage area without a valid authorization token granting access to the particular data storage area. In responding to a request for metadata access, the system can use the specified metadata access setting to generate a response to the request, so that the response omits data classifications for one or more types of data in the particular data storage area (e.g., which the settings did not authorize to be provided). As another example, the response can be generated to generalize one or more data classifications based on the user-specified metadata access setting (e.g., to indicate "exercise data" rather than "daily step count measurements," or to indicate that data was added "within the last month" rather than "data added today"). This can be done by moving up in the levels of the data classification hierarchy to a level that is permitted by the metadata access settings for the data storage area.

In some cases, user-specified metadata access settings for a particular data storage area limit different applications to different levels of access to metadata for the particular data storage area. In response to requests from different applications for metadata regarding the particular data storage area, the system provides different subsets of the metadata to the different applications based on the user-specified metadata access settings.

Figure 11:
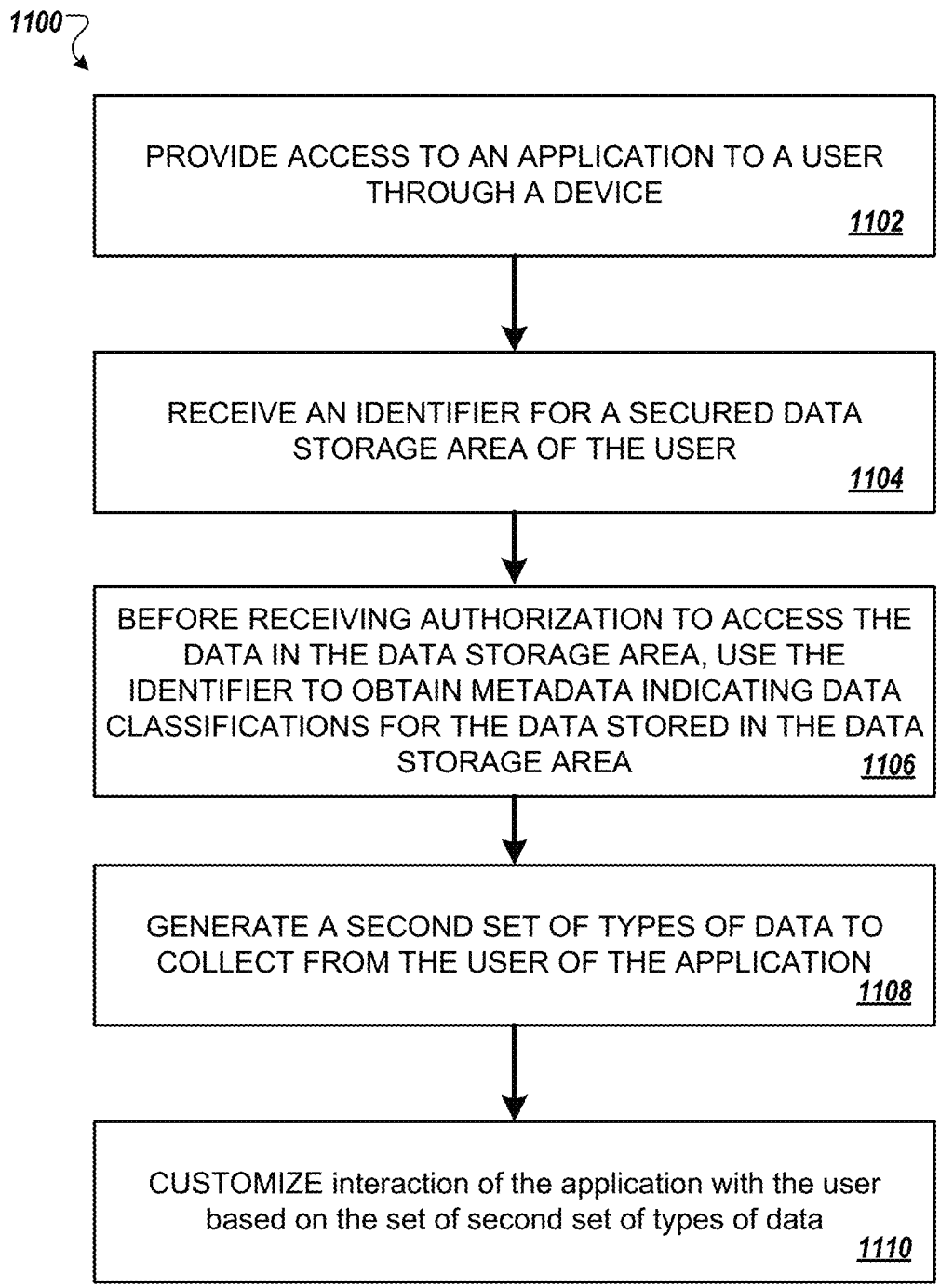

FIG. 11 is a flow diagram that illustrates a process 1100 of using metadata for a data storage area. The process 1100 can be performed by one or more computers, such as by a client device, a server system, a client device and server system operating together, and so on. The process 1100 provides an example where an application, whether operating at a client, at a server, or a combination of both, can use metadata for a data storage area to customize its functionality for the user. The metadata, and the techniques to provide it and access it through an API, can be as discussed above.

As an example use, the process 1100 can be used in a manner where a candidate or participant for a research study provides a data storage area identifier, and a customized, reduced amount of data collection is determined for that individual, based on metadata about the data storage area for the user. The application can customize the operations of the application and the user's device to adjust data collection activities for the individual, given what was previously collected or is being collected in an ongoing manner. In this manner, the data being collected through the user's personal health tracking, private medical treatment, or monitoring performed for other research studies can be considered and used rather than initiating redundant data collection.

For example, a user can receive access to a research study application. The access can be initial access through a program gallery showing different applications for health and wellness, for different research studies, and so on. As another example, the access can be provided as a user downloads or installs an application or module that supplements an existing application, or through a purely web-based interface, such as a web page or web application. The application can request, and the user provides, an identifier for a data storage area to the research study application. The research study app uses the identifier, and the API provided by the computer system 110, to access metadata (e.g., data classifications) describing the health data of the user that is stored in encrypted form in the data storage area corresponding to the identifier. As discussed above, the API can provide the metadata without revealing the values of the health data in the encrypted area, the identity of the user, or the existence or identity of other data storage areas of the user. With the metadata, the research study application provides a personalized indication of the eligibility status of the user (e.g., whether the user is eligible or not, and what additional information would be needed to determine eligibility), value of the research study to the user (e.g., benefits of the research study that are applicable to the user), and features of the research study applicable to the user based on the metadata. The customized information can answer the question why the user should provide his or her data to the application. For example, the system may indicate that the user is a good fit for the research study, and that the study is looking people that have certain types of data that the user's data storage area provides. When creating research studies, researchers often try to increase the applicability of the study to the participants, e.g., a high match between participants and study content, to increase recruitment, compliance with study procedures, and retention to the end of the study. These personalized indications from the initial enrollment and throughout the study can increase the effectiveness of all of these processes.

Some applications may provide monitoring programs, such as to monitor health of an individual through one or more devices (e.g., phone, smart watch, activity tracker, etc.). For example, some applications may be configured to monitor health for delivering medical treatment, providing digital therapeutics, improving physical fitness or athletic performance, encouraging behavior change (e.g., smoking cessation, addiction recovery, weight reduction, medication adherence, etc.), and providing precision medicine and personalized medicine. In addition, applications in the decentralized framework can be used for health research, e.g., clinical trials, observational studies, longitudinal studies, and so on.

In many cases, monitoring programs may have significant minimum data collection requirements that need to be met. For example, for a fitness program to have maximum effect, the application may need information about a user's diet, sleep, heart rate, and other physiological and/or behavioral attributes collected on a regular basis, e.g., through sensors of mobile and wearable devices as well as regular survey responses. Similarly, the application for a health research study may similarly require a minimum set of data collection, e.g., a blood test once a month, daily heart rate measures, daily survey responses about diet, daily exercise data (e.g., step counts), and so on, as specified in a study protocol for the health research study. Research studies often also need significant amounts of data from other sources, such as medical history, family history, genomics data, treatment history for medical conditions of chronic diseases, and so on. Having these types of data available is often a requirement for eligibility of an individual to participate in a research study or may be a requirement to continue participating.

In the case of health research studies, compliance with the data collection requirements is particularly important. Participants that do not provide the minimum set of collected data with appropriate consistency (e.g., those that miss too many days of data collection) must often be removed from the study cohort for being non-compliant and their data may not be able to be used. This is a setback for the researchers and the study, since the cohort may be at risk of having too few remaining participants or may lack the desired level of diversity among participants that was desired and expected. Similarly, the effort that the participant expended in providing partial but insufficient compliance is wasted, and the participant fails to receive the information and treatment benefits the study can provide. In addition, the computing resources of both the server and the participant's devices in collecting data over is wasted. As a result, it is desirable for the efficiency and effectiveness of research studies to enroll participants who are capable of and likely to provide the needed types of data, and so comply with the study's requirements over the entire duration (e.g., a predetermined monitoring period, typically weeks, months, or years) of the research study.

In many cases, the data that a research study or application needs may be already present in data storage areas of individuals. For example, much of the data needed to determine eligibility of an individual for a research study, e.g., a recent blood test, medical history data, and so on, may already be present in EHR in one or more data areas owned and controlled by the individual. Similarly, data that the research study needs to be collect from an individual on an ongoing basis as part of the research study may be already performed as part of ongoing data collection (e.g., through periodic, regular, or scheduled collection events) performed for the user (e.g., by other applications, by other research studies, by the user's wearable devices, and so on). Applications for research studies and other purposes can make use of the existing data sets and ongoing data collection schemes for a user to reduce the additional burden the application applies on users. To the extent that data collection needs of an application overlap with the data that is currently in, or is periodically added to, the relevant data can be used by the application rather than adding new data collection actions. This is a significant benefit to users, who can leverage existing data sets and currently-active data collection schemes to gain significant benefits from joining a research study (e.g., additional health information, treatments, etc.) while minimizing the additional commitment of time and device resources needed (e.g., adding only an incremental amount of additional data collection for items outside the set of data collection already being done).

Traditionally, a research study would not be able to easily learn of the existence of these sources of data about a candidate or participant, much less gain access to the data. As a result, research studies often require data collection that is duplicative or redundant given monitoring previously performed or already ongoing (e.g., requiring a blood test when the individual obtained one from his private doctor; requesting new exercising monitoring when the user already has exercise monitoring through a phone or wearable device; requiring completion of surveys that the user is already filling out for another doctor; requiring manual entry of medical history data that the individual; etc.). In particular, if an individual is part of multiple research studies (consecutively or concurrently), there is often overlap in the types of data collected for the various studies, yet each study often will collect the same data independently. The issue of unnecessary duplicative monitoring results in significant inefficiency, including unnecessary drain on battery life and processing power of the user's devices, as well as unnecessary drain on the user's time and effort, making it more likely that the participant will fail to complete research studies. Requiring unnecessary data collection also inflates the apparent burden (e.g., amount of time, resources, interactions, and overall inconvenience required for a user to participate), which discourages individuals from participating.

Using the data storage areas and metadata discussed herein, the computer system 110 can enable applications from many different providers to customize the experiences and requirements provided to users. When a user is considering an application, the set of data collection requirements can be adjusted based on types of data and data collection that the metadata indicate. For example, an application for a clinical trial may normally require 6 items of information to be entered, and 5 other items to be monitored on a regular basis. Once a candidate for the clinical trial provides an identifier for the candidate's data area(s), the application can retrieve the metadata for the data area(s) without having been issued any authorization to the underlying data. The application may determine, based on the metadata, that 3 of the 6 needed one-time items are already in the data area(s), and 2 of the 5 items for regular monitoring are already being added on a regular basis (e.g., based on the metadata a data collection pattern, recency of measurements, indication of ongoing measurements, etc.). As a result, rather than identify a total of 11 items needed to participate, the application can customize the indication of needed items to show only 6 items needed beyond access to the data in the user's data storage areas. This can show the user the true additional commitments that would come with enrollment in the study, rather than an inflated set that may show an improperly high burden that may discourage participation.

The system can use the same techniques in customizing the actual behavior of the application. For example, an application may be configured to initiate monitoring of 5 types of data daily for most users. Based on the metadata for user's data area(s) showing that two of the 5 types are already being collected (e.g., by a fitness tracker and application saving the data regularly into a particular data storage area), the application can customize the actual data collection performed to omit the two types of data already being collected. In lieu of initiating duplicative data collection, the application can be configured to request and obtain access authorization for the particular data storage area(s) where needed data is stored. In some implementations, the application can wait to obtain access authorization for those data area(s), and can verify that the needed data of the appropriate type, quantity, and quality is present, before altering the data collection parameters for the user.

As another example, using the metadata about a user's private data storage area(s), a computer system can identify data storage areas (and thus the corresponding users) that store types of data that indicate eligibility, or at least that the metadata indicates that the encrypted, private data includes information for the system to determine eligibility. The system can then invite those participants to be considered for enrollment, by authorizing access to their data storage areas for full eligibility consideration. The information provided by the data storage areas also enables the computer system 110 and/or other systems to better evaluate factors such as (i) eligibility of different individuals (e.g., to join a particular research study as a participant, to use a particular application, etc.), (ii) the likelihood of compliance with monitoring or data collection needed, and (iii) level of value that the application can provide to the individual.

The process 1100 includes providing, by the one or more computers, access to an application to a user through a device (1102). The application can accessed in any appropriate form, such as in a web application, installable stand-alone native application (e.g., a mobile application from an application store), or a downloadable module that supplements or customizes another application. The application specifies a first set of types of data to collect from users of the application. As discussed above, the data to collect can be health data to be collected once (e.g., an initial blood test) or multiple times (e.g., daily heart rate measurements and survey responses). For example, for a research study, the application can be configured to collect physiological and behavior data, using sensors, surveys presented to the user, or other techniques. The data collection can be context-driven, e.g., initiated automatically in response to the detection of a predetermined trigger or condition.

The application can be configured to support a research study in various ways. In addition to monitor physiology and behavior of a user, the application can be configured to provide the data to a data storage area for the application, in association with a user identifier for the user. The application can provide features that enable communication to or from the researchers or doctors associated with the study. The application can also provide instructions to the user and health interventions related to the subject of the study. For example, the application may be configured to monitor for drug effects (e.g., positive desired effects or undesired side effects), risks, changes in measures of physiological properties or behavior relative to reference levels or ranges or to baseline measures for the user.

The process 1100 includes receiving, by the one or more computers, an identifier for a secured data storage area of the user (1104). The identifier can be provided by the user to the application. For example, when the user accesses the application, a graphical user interface can be provided, which has an input field or other control for entering the identifier of one or more data storage areas. In some implementations, the application or the user can invoke an authorization tool, which can reside on the user's local client device. The authorization tool can store a set of identifiers for the data storage areas that the user is managing using his or her device. The authorization tool can enable the user to select from among the various data storage areas of the user. For example, the user can have previously assigned nicknames or customized labels for the different areas (e.g., "Study 1," or "Fitbit data"), to enable the user to easily identify and select the desired areas. The authentication tool can populate a text field or other control of the application with the actual identifier for the application (e.g., a number or alphanumeric string that uniquely identifies the data area).

The data storage area can be one that is managed by a server system configured to (i) provide access to data in the data storage area in response to an access token for the data storage area and (ii) provide metadata indicating data classifications for data in the data storage area without requiring an access token for the data storage area. In providing this functionality, the server system restricts access to the underlying data in the data storage area, e.g., so that values of the health measures in the data storage area cannot be obtained without a valid access token that permits access to that data storage area.

As with other processes and systems described herein, the ecosystem of applications is decentralized, enabling may different third-parties to create and deploy applications that may access and rely on the data storage areas through the provided APIs. The data storage areas themselves may be managed by a central authority, or collection of authorities.

The process 1100 includes, before receiving authorization to access the data in the data storage area, using, by the one or more computers, the identifier to obtain the metadata indicating data classifications for the data stored in the data storage area (1106). For example, the application uses the identifier in making one or more API calls to a server system that request metadata for the data storage area. In response, the server system can provide the requested metadata from the server system over a communication network. The type, amount, and level of detail in the metadata may be limited by user-specified metadata access settings.

The process 1100 includes generating, by the one or more computers, a second set of types of data to collect from the user of the application (1108). The second set can be customized for the user based on the data classifications indicated by the metadata for the data storage area indicated by the identifier provided by the user. For example, the second set of types of data includes a subset of the types of data in the first set and omits one or more types of data in the first set.

As an example, the application may be for a clinical trial that is configured to obtain daily heart rate measures, daily step count measures, and daily sleep duration measures from the user. Other requirements may include a one-time blood test and family medical history data. The user provided an identifier for a particular data storage area, and the application used the API of the server system to request and obtain the metadata indicating the types of data present in the particular data storage area. The application does not have access to the underlying data of the particular data storage area, because the application does not yet have any user authorization or access token to enable that access. Nevertheless, the application compares the types of data that the metadata indicates to be available from the data storage area with those needed by the application. For example, the application can identify items that overlap between the metadata-indicated data classifications and data classifications for types of data needed by the application. To facilitate this comparison, the application can use a predetermined set of data classifications or a taxonomy of types of data as discussed above. The application may determine, from the metadata, that the particular data storage area includes results of a blood test taken within the last month, and that heart rate and daily step count are also added in a regular daily pattern. From this, the application determines that the overlapping types of data do not need additional data collection initiated, and that instead the second set of types of data that need to be collected are family medical history data and daily sleep duration measures, which is a proper subset (e.g., fewer than all) of the first set of types of data.

The system can use the metadata to determine whether a data storage area has data of the appropriate type or classification needed for the monitoring program. In addition, the system can also use the metadata to determine whether other characteristics of that stored data allow it to be used to reduce or eliminate data collection for that type of data by the monitoring program. For example, the system can determine whether the stored data for a particular type of measurement meets a corresponding set of predetermined criteria. The predetermined criteria may set constraints or conditions that need to be met for the monitoring program to use the data, and these criteria may be set by or may be derived from a research study protocol that defines the needed data collection for participants in the research study. The criteria can be different for different types of data needed. For example, the minimum criteria for acceptable resting heart rate measurements (e.g., from a sensor of a wearable device, measured twice a day) can be different from the minimum criteria for acceptable exercise data (e.g., daily value, from a phone or wearable device). The criteria can set thresholds or requirements for (1) timing (e.g., rate or frequency of data capture, how recently the most recent data was captured, the span of time or duration over which), (2) data collection parameters, (3) data source (e.g., user input, EHR, device sensor data, etc.), (4) data quality (e.g., accuracy, precision, consistency, reliability, etc.), (5) pattern of data collection, and so on. The system can consider any or all of these factors, for each type of relevant data that the metadata indicates to be present. Depending on the user's metadata access settings, not all of these types of metadata may be available for every individual.

The process 1100 includes customizing, by the one or more computers, interaction of the application with the user based on the set of second set of types of data (1110). The customization can occur at any of various different stages, including before a user enrolls or signs in to the application, such as when the application is providing an overview or preview of the capabilities of the application. As another example, for a research study, the customization can be performed prior to enrollment, during enrollment, or after enrollment. The customization can tailor the set of additional user actions needed and user data collection needed for participation in the study. For example, once the application has determined that the data sources, patterns, and ongoing data collection fulfills one or more requirements of the research study, the application can use the second set of types of data to show the remaining items that still will need to be collected or activities that will still need to be performed for participation in the research study.

The customization can also involve altering various interactions with the user. For example, the system can alter surveys and other form to omit items already indicated to be present in the data storage area for the user.

The application can also determine whether to request authorization to access to the data area based on the metadata. For example, based on the metadata, the application can determine whether the types of data, and/or amounts of data and span of time covered, make it worth it for the application to obtain and use the underlying data for the data storage area.

The customization can include configuring the application to change how it interacts with the user's device (e.g., in activating and deactivating sensors), and to instead rely on retrieving or accessing data for certain data types from in the data storage areas of the user instead of causing new data collection. For example, based on the generated second set of data, the system can customize behavior of the application to (i) use one or more sensors or user interfaces to collect data from the user for each of the types of data in the second types of data, and (ii) obtain data for the particular type of data from the data storage area instead of collecting data for the particular type of data from the user. This can provide a number of advantages, including saves power of client device, reducing the number of network interactions required, limiting the storage space needed for measurements (e.g., by re-using data already stored), etc.

In general, an application can identify data classifications for what should be collected, receive data classifications in the metadata, and compare the two to determine if there is a match. If there is a match, this can indicate that data of a type that the application uses or needs is present in the data storage area. The application may use the data type taxonomy or hierarchy to resolve differences in classifications needed and those indicated in the metadata. For example, if the application needs exercise data, and the area has actigraphy data (which the hierarchy indicates to be in the same category but is more specific type within the category), the application can determine that the data meets the need of the application.

The customization can cause one or more devices alter their operation to carry out monitoring that differs from the default or typical monitoring that the application instructs. The monitoring can be configured to adjust operation of the device to set or change sensor parameters used by the device to perform sensor measurements using one or more sensors, including changing at least one of a set of sensors used, a type of property or characteristic measured, a timing or schedule at which sensor measurements occur, a frequency of the sensor measurements, durations that the sensors are powered on and active, a level of accuracy or precision for the sensor measurements, rules for evaluating validity or quality of the sensor measurements, sets of events or conditions that trigger initiation of the sensor measurements, software settings for an application or operating system in order to enable the sensor measurements, or a set of post-measurement processing steps to perform for data collected by the sensor measurements.

The monitoring can be customized to adjust operation of the device to set or change data storage parameters used by the device, such as: a format for a message, data stream, or data package to provide the data from the sensor measurements; an aggregation operation for aggregating measurements of the sensor data; a filtering operation for filtering or smoothing results of the sensor measurements; or an accuracy or precision setting for storing results of the sensor measurements.

The monitoring can be customized to adjust operation of the device to set or change network communication parameters used by the device to report acquired data to a server system over a computer network, the network communication parameters comprising at least one of a server or network address to which acquired data is transmitted, a network protocol or encryption scheme to use in transmitting acquired data, one or more events or conditions that trigger transmission of acquired data, or one or more ranges or thresholds that trigger transmission of acquired data.

The monitoring can be customized to cause devices to perform various changes or configuration actions, often without requiring user action. The actions can include: enabling or disabling a sensor of the device or a device communicatively coupled to the device; setting or changing sensor parameters used by the device to conduct sensor measurements using one or more sensors, including changing at least one of a set of sensors used, a type of property measured, a timing of the sensor measurements, a frequency of the sensor measurements, a level of accuracy or precision for the sensor measurements, rules for evaluating validity or quality of the sensor measurements, sets of events or conditions that trigger initiation of the sensor measurements, software settings for an application or operating system in order to enable the sensor measurements, or a set of post-measurement processing steps to perform for data collected by the sensor measurements; setting or changing data storage parameters used by the device to format or store acquired data to a server system over a computer network, the data storage parameters specifying at least one of: a format for a message, data stream, or data package to provide the data from the sensor measurements; an aggregation operation for aggregating measurements of the sensor data; a filtering operation for filtering or smoothing results of the sensor measurements; or an accuracy or precision setting for storing results of the sensor measurements; setting or changing network communication parameters used by the device to report acquired data to a server system over a computer network, the network communication parameters comprising at least one of a server or network address to which acquired data is transmitted, a network protocol or encryption scheme to use in transmitting acquired data, one or more events or conditions that trigger transmission of acquired data, or one or more ranges or thresholds that trigger transmission of acquired data; setting or changing power usage parameters of the device, including changing a device power state or sleep setting of the device; altering a user interface of an application installed at the device, including changing a set of interactive user input controls presented in the user interface; setting or changing interactive content to be presented by the device, the interactive content including at least one survey, prompt, or electronic form; or setting or changing parameters for presenting the interactive content that includes at least one of timing, frequency, format, triggers, or contexts for providing the interactive content.

As noted above, the application may selectively omit data collection based on determining whether certain conditions or constraints are met. For example, the application can identify, for a particular type of data needed by the application, one or more criteria for data of the particular type of data to be used by the application, wherein the one or more criteria specify a time constraint or a constraint for a level of precision, a source of data, or amount of data needed. The application can also determine, based on the metadata, that the one or more criteria is met for the data of the particular type in the data storage area. The particular type of data is then omitted from the second set of types of data based on determining that the one or more criteria for the particular type of data is met. The criteria may specify a characteristic, condition, threshold, quality standard or other objective reference that can be checked.

On the other hand, if the one or more criteria is not met (e.g., the metadata indicates that a needed characteristic of the health data is not present or the health data does not satisfy a condition), then data collection of that type of data by the application is not omitted. For example, there may be minimum levels of accuracy, precision, amount of data, source of data, consistency of data acquisition, and so on that represent required aspects of data quality needed in order for the data to be used by the application (e.g., to be accepted by, relied on, used as substitute for new measurements). The application can verify whether these levels are met in determining whether to initiate its own data collection or rely on data provided through a data storage area. If the criteria is not met for a type of data that the metadata indicates is present in the data storage area (e.g., data is of the right type but is too old, too infrequently collected, collection is too irregularly timed, or the data source is not approved or does not provide sufficient precision), then the application will still collect its own data for that data type, even though some data of the same type is in the data storage area.

In some implementations, the metadata indicates data collection parameters used to generate the data of a particular type that is both needed by the application and included in the first set of types of data. The second set of types of data can be generated to omit the particular type of data from the second set of types of data based on determining that the data collection parameters used to generate the data of the particular type in the data storage area satisfy a set of predetermined criteria. Examples of data collection parameters include device type or model of device used, sensor or sensor type used, level of precision captured, duration of measurement, and the context in which the measurement was captured (e.g., location, time, date, etc.).

In some implementations, the metadata for the data area indicates that the data storage area is designated to receive repeated future measurement results for a particular type. The second set of types of data can be generated to omit the particular type of data from the second set of types of data based on determining that the metadata for the data area indicates that the data storage area is designated to receive repeated future measurement results for the particular type.

In some implementations, the application is configured to repeatedly obtain measurements for a particular type of data in the first set of types of data. The particular type of data can be one that describes characteristics of the user (e.g., physical characteristics, mental health characteristics, etc.) or behavior of the user. The metadata for the data area indicates characteristics of a pattern of previous data collection actions performed to collect data of the particular type for the user that is stored in the data storage area. The second set of types of data can be generated to omit the particular type of data from the second set of types of data based on determining that the pattern of previous data collection actions satisfies a set of predetermined criteria.

Some implementations of metadata may indicate directly whether future data collection is enabled or scheduled. For example, some metadata values may indicate whether an item is collected periodically or regularly, on a schedule, or with at least a minimum level of consistency. However, in other cases, the metadata may only provide information about past data collection. In these cases, decisions can be based on indications of the pattern with which data was collected, such as frequency (e.g., daily, weekly, monthly), duration of time (e.g., over a week, a month, a year), recency (e.g., most recently measurement is today, yesterday, last week, last month), and consistency or variability. From these aspects, the system can infer whether the user is currently in a pattern of collecting different types of data with sufficient frequency, regularity, etc. to meet the needs of the application.

The system can use the pattern of past data collection for other purposes, such as to identify candidates for a cohort, to predict likelihood of compliance with study requirements, to prioritize or rank candidates, or to assess eligibility of a candidate. For example, if a study involves participants answering a daily survey or performing daily sensor data capture, users whose data areas demonstrate that they have done, or are currently doing, the needed type of data collection are much more likely to be able to meet the requirements of the study if enrolled. In a similar manner, the types of data and tools used can also be strong indicators. If a user has activity tracker results in their data area, it is likely that the user has an activity tracker, which may be a requirement for eligibility or may be a boost to the suitability of the individual for a particular study.

Various applications (whether for research studies, health care delivery, or other purposes) can be used to provide digital therapeutics to users based on the data in a user's data storage area(s). Digital therapeutics can deliver medical interventions directly to patients using evidence-based software to treat, manage, and prevent a broad spectrum of diseases and disorders. These techniques can deliver therapies using smartphones, tablets, wearable devices, and other devices, which increases patient access to clinically safe and effective therapies. Digital therapeutics have been shown to be effective in treating a variety of medical conditions, such as anxiety, depression, ADHD, insomnia, substance abuse, obesity, hypertension, and more. Similarly, digital therapeutics can assist user in managing diseases such as diabetes, cancer, heart disease, chronic obstructive pulmonary disease (COPD), and so on. Digital therapeutics are also provided as a preventive measure for patients who are at risk of developing more serious conditions. For example, a patient with prediabetes may be prescribed digital therapeutics as a method to change their diet and behavior that could otherwise lead to a diabetes diagnosis.

Digital therapeutics interventions can include various interactions, including those made remotely through a smartphone or other user device. In many cases, the interactions can be initiated automatically by software on a user device or by a server system sending instructions to cause the user device to provide the interactions. As a result, digital therapeutics can be provided automatically, without a user having to manually open an application and seek out interaction. In many instances, digital therapeutics and other health care programs can operate in an "always on" manner, initiating interactions automatically based on a schedule, based on the context of a user device, or based on detected conditions or triggers (e.g., sensor measures or user inputs that indicate predetermined indicators or markers for certain behaviors, situations, physiological characteristics, and so on).

As a few examples of interactions made through digital therapeutics, an application can inform a user of a health risk, provide media, generate an interactive form such as a survey, provide a test or assessment, send a notification message, provide recommendations, provide content from a social media platform, provide instructional activities or games, and so on. In some cases, the system can prompt a user to set, adjust, or view a goal, or challenge, remind, or inform the user about a goal. Similarly, the system may prompt a user to take an action, record a measurement from a device, provide content for a user to read or view, initiate a challenge for a user to change behavior (or to perform a specific action or task). The system may communicate with family of a user, friends of a user, or others regarding a user's goals or status, including with health service providers. In general, interactions may involve visual output, audio output, haptic output, typed or touchscreen input, voice input, gesture input, and other input/output modalities. The media provided as part of the interactions can include content such as text, videos, audio segments, images, interactive instructional materials, messages (e.g., indicating encouragement, reminders, etc.), games, and other content.

To make better predictions and provide more accurate diagnostic and treatment recommendations, an application can provide interventions that prompt users to complete an assessment at specific times during the day or in response to specific situations or contexts. Examples include ecological momentary assessments (EMA). Applications can also support passive ascertainment of changes in clinical status, in behavior, or in other aspects. Applications can be configured to provide behavioral support, such as self-management strategies, immediately following assessments or detection of triggering conditions. The approaches to data collection and treatment can be highly personalized. The system can tailor or personalize digital health interventions based on each individual's characteristics (e.g., race, gender, socio-economic status, etc.) for disease prevention, presentation, management, and outcomes and that ultimately contribute to a more individualized approach to health care.

Applications can be used to monitor the effectiveness of treatment of the user and adjust treatment accordingly. For example, if provided digital therapeutics do not result in the expected or desired improvements in physiological attributes or user behaviors, the computer system 110 can select and provide different digital therapeutics interventions. As another example, if medications provided do not yield the desired effects, or if the collected data indicates that there are problematic side effects, an application can recommend changes to the medication regimen, such as changing the dose, type of medication, frequency or timing of administration, and so on. In making treatment decisions and recommendations, the application can use data indicating medical research results and best practices, for example, to provide actions based on clinically validated and evidence-based treatment steps that can be captured in rules, look-up tables, databases, or other data structures.

The data collected by applications and the computer system 110 and used in any of the examples and implementations discussed above can include a variety of information from a variety of sources. Data can be collected for categories representing a variety of individual, community, or public health conditions and behaviors. This data can include attributes that are biological, physical or physiological, mental, emotional, environmental, or social. The collected data can include biological attributes, such as genetic makeup, genomics, family history, sensory abilities (e.g., ability to see, perception of light and dark, perception of color, extent of ability to smell, ability to touch and sensitivity, ability to hear and sensitivity, etc.). These may reflect biological factors that a person cannot control. The collected data can include physical or physiological attributes, e.g., weight, muscle mass, heart rate, sleep, nutrition, exercise, lung capacity, brain activity, etc. Some physical attributes may result from the impact of lifestyle choices or things that a person can control. The collected data can include mental attributes, such as interpretation of brain related signals, indications of chemical imbalances, education levels, results of mental tests, etc. The collected data can include emotional attributes, such as interpretation of self-reported data, or classified audio or video related data that suggests individual responses to stimuli. The collected data can include environmental data, such as location data, air quality, audible noise, visual noise, temperature, humidity, movement (and potentially effects of movement such as motion sickness, etc. The collected data can include social attributes, such as whether a subject is socially engaged, exhibits social avoidance, experiences the impact of acceptance or responsiveness emotionally, and so on.

The data collected, stored, and used in the systems and methods herein (e.g., including data collected or used by any of various applications and stored in data storage area) can include various other types of data including:

Lab and diagnostic data (e.g., assay data, blood test results, tissue sample results, endocrine panel results);

Omics data (e.g., data relating to genomics, proteomics, pharmacogenomics, epigenomics, metabolomics, biointeractomics, interactomics, lifeomics, calciomics, chemogenomics, foodomics, lipidomics, metabolomics, bionomics, econogenomics, connectomics, culturomics, cytogenomics, fermentanomics, fluxomics, metagenomics, metabonomics, metallomics, O-glcNAcomics, glycomics, glycoproteomics, glycosaminoglycanomics, immunoproteomics, ionomics, materiomics, metalloproteomics, metaproteogenomics, metaproteomics, metatranscriptomics, metronomics, microbiomics, microeconomics, microgenomics, microproteomics, miRomics, mitogenomics, mitoproteomics, mobilomics, morphomics, nanoproteomics, neuroeconomics, neurogenomics, neuromics, neuropeptidomics, neuroproteomics, nitroproteomics, nutrigenomics, nutrimetabonomics, oncogenomics, orthoproteomics, pangenomics, peptidomics, pharmacoeconomics, pharmacometabolomics, pharmacoproteomics, pharmaeconomics, phenomics, phospholipidomics, phosphoproteomics, phylogenomics, phylotranscriptomics, phytomics, postgenomics, proteogenomics, proteomics, radiogenomics, rehabilomics, retrophylogenomics, secretomics, surfaceomics, surfomics, toxicogenomics, toxicometabolomics, toxicoproteomics, transcriptomics, vaccinomics, variomics, venomics, antivenomics, agrigenomics, aquaphotomics);

Biologically sampled data (e.g., data describing blood, urine, saliva, breath sample, skin scrape, hormone levels, ketones, glucose levels, breathalyzer, DNA, perspiration, and other biological samples and derived data);

Cardiac-related biodata (e.g., data from ECG/EKG monitors, heart rate monitors, blood pressure monitors);

Respiratory-related biodata (e.g. data from spirometers, pulse oximeters);

Neurological-related biodata (e.g. data from EEG monitors);

Behavior data (e.g. movement patterns, gait, social avoidance);

Drug data (e.g., prescription information, pharmacological data);

Substance use data (e.g., alcohol, medication, insulin, recreational drugs, tobacco);

Sleep data (e.g., motion data, heart rate data, body temperature, perspiration, breathing data, ambient light, ambient sound, ambient temperature);

Exercise data (e.g. performance data, distance covered, activity, VO2 Max),

Physical activity data (e.g., step counts, heart rate, flights climbed, altitude, other data from fitness trackers);

Mood data (e.g., happiness, depression, PHQ9, BMIS data and other scales/reporting mechanism);

Positioning and location data (e.g., GPS data, gyroscope, altimeter, accelerometer, linear acceleration, received signal strength indicator from nearby emitters such as WiFi access points, Bluetooth sensors and sensor networks and Cellular towers);

Environmental data (e.g., air quality data, ozone data, weather data, water-quality data, audible decibel levels, interpreting measured audio data, measuring luminance lux, interpreting measured light wavelengths, measuring temperature and gases or particles—such as formaldehyde (Molecular Formula: $H_2CO$ or $CH_2O$); alcohol vapor (Molecular Formula: hydroxyl group-OH, e.g., Isopropyl$C_3H_8O$ or $C_3H_7OH$, as well as Ethanol: $C_2H_6O$ or $C_2H_5OH$); benzene ($C_6H_6$); Hexane ($C_6H_{14}$); Liquefied Petroleum Gas (LPG) which could include a mixture of butane (Molecular Formula: $CH_3CH_2CH_2CH_3$ or $C_4H_{10}$) and isobutene (Molecular Formula: $(CH_3)_2CHCH_3$ or $C_4H_{10}$ or $(CHC_4H_{10})_2 CHCH_3$); propane (Molecular Formula: $CH_3CH_2CH_3$ or $C_3H_8$); natural coal or town gas which could include of methane or natural gas (Molecular Formula: $CH_4$); carbon dioxide (Molecular Formula: $CO_2$); hydrogen (Molecular Formula: $H_2$); carbon monoxide or possibly smoke (Molecular Formula: CO); and oxygen (Molecular Formula: $O_2$) in the environment surrounding an individual inside and outside the contextual location of the potential subjects such as home, office, and including vehicle data—such as speed, location, amount of time driving, mood while driving, environmental data in the car).

A number of implementations have been described. Nevertheless, it will be understood that various modifications may be made without departing from the spirit and scope of the disclosure. For example, various forms of the flows shown above may be used, with steps re-ordered, added, or removed.

Embodiments of the invention and all of the functional operations described in this specification can be implemented in digital electronic circuitry, or in computer software, firmware, or hardware, including the structures disclosed in this specification and their structural equivalents, or in combinations of one or more of them. Embodiments of the invention can be implemented as one or more computer program products, e.g., one or more modules of computer program instructions encoded on a computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) can be written in any form of programming language, including compiled or interpreted languages, and it can be deployed in any form, including as a stand alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a tablet computer, a mobile telephone, a personal digital assistant (PDA), a mobile audio player, a Global Positioning System (GPS) receiver, to name just a few. Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the invention can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Embodiments of the invention can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the invention, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

In each instance where an HTML file is mentioned, other file types or formats may be substituted. For instance, an HTML file may be replaced by an XML, JSON, plain text, or other types of files. Moreover, where a table or hash table is mentioned, other data structures (such as spreadsheets, relational databases, or structured files) may be used.

Particular embodiments of the invention have been described. Other embodiments are within the scope of the following claims. For example, the steps recited in the claims can be performed in a different order and still achieve desirable results.

The invention claimed is:

1. A computer-implemented method performed by one or more computing devices that are configured to connect to a communication network, the method comprising:

providing, by the one or more computing devices, access to a health application to a user through a computing device, wherein the health application specifies a first set of types of health data to collect from users of the health application;

receiving, by the one or more computing devices, an identifier for a secured data storage area for the user, the identifier being provided by the user to the health application, wherein the data storage area is managed by a server system configured to (i) provide access to health data in the data storage area in response to an access token for the data storage area, (ii) disallow access to the health data in the data storage area when an access token for the data storage area is not provided, and (iii) provide metadata indicating data classifications for the health data in the data storage area without requiring an access token for the data storage area;

before receiving authorization to access the health data in the data storage area, using, by the one or more computing devices, the identifier to obtain the metadata indicating data classifications for the health data stored in the data storage area, the metadata being obtained from the server system over the communication network;

determining, by the one or more computing devices, a second set of types of health data to collect from the user of the health application, the second set being customized for the user based on the data classifications indicated by the metadata for the data storage area indicated by the identifier provided by the user, wherein the second set of types of health data includes a subset of the types of health data in the first set and omits one or more types of health data in the first set; and customizing, by the one or more computing devices, interaction of the health application with the user, including generating user interface data used to automatically provide a customized user interface that is customized for the user, wherein the customized user interface is customized to present a subset of content of the health application, wherein the subset of content is selected based on the second set of types of health data determined based on the data classifications indicated by the metadata for the data storage area.

2. The computer-implemented method of claim 1, further comprising:

determining multiple types of health data that the health application is configured to obtain from users of the health application, wherein the determined types of health data are the first set of types of health data; and for each of the multiple types of health data that the health application is configured to obtain, determining whether the metadata indicates that data of that type of health data is stored in the data storage area;

wherein determining the second set of types of health data comprises:

based on determining that the metadata indicates that data of a particular type of health data is stored in the data storage area, determining the second set of types of health data to omit the particular type of health data; and wherein customizing interaction of the health application with the user comprises:

based on the determined second set of types of health data, customizing behavior of the health application to (i) use one or more sensors or user interfaces to collect data from the user for each of the types of health data in the second set of types of health data, and (ii) obtain data for the particular type of health data from the data storage area instead of collecting data for the particular type of health data from the user.

3. The computer-implemented method of claim 2, further comprising:

identifying, for the particular type of health data, one or more criteria for data of the particular type of health data to be used by the health application, wherein the one or more criteria specify a time constraint or a constraint for a level of precision, a source of data, or amount of data needed; and determining, based on the metadata, that the one or more criteria is met for the data of the particular type in the data storage area;

wherein the particular type of health data is omitted from the second set of types of health data based on determining that the one or more criteria for the particular type of health data is met.

4. The computer-implemented method of claim 1, further comprising:

determining, based on the metadata for the data storage area, that the data storage area stores data of a particular type of health data that is included in the first set of types of health data;

identifying a characteristic or condition that data of the particular type is required to meet to be used by the health application; and determining, based on the metadata, that the data of the particular type in the data storage area does not have the characteristic or does not satisfy the condition;

wherein determining the second set of types of health data comprises:

based on determining that the data of the particular type in the data storage area does not have the characteristic or does not satisfy the condition, including the particular type of health data in the second set of types of health data such that the health application initiates collection of data of the particular type for the user.

5. The computer-implemented method of claim 1, further comprising determining, based on the metadata for the data storage area, that the data storage area stores data of a particular type of health data that is included in the first set of types of health data;

wherein the metadata indicates data collection parameters used to generate the data of the particular type that is included in the first set of types of health data; and wherein determining the second set of types of health data comprises omitting the particular type of health data from the second set of types of health data based on determining that the data collection parameters used to generate the data of the particular type in the data storage area satisfy a set of predetermined criteria.

6. The computer-implemented method of claim 1, wherein the health application is configured to repeatedly obtain measurements for a particular type of health data in the first set of types of health data, wherein the particular type of health data describes characteristics of the user or behavior of the user;

wherein the metadata for the data storage area indicates characteristics of a pattern of previous data collection actions performed to collect data of the particular type for the user that is stored in the data storage area; and wherein determining the second set of types of health data comprises omitting the particular type of health data from the second set of types of health data based on determining that the pattern of previous data collection actions satisfies a set of predetermined criteria.

7. The computer-implemented method of claim 1, wherein the health application is configured to repeatedly obtain measurements for a particular type of health data in the first set of types of health data, wherein the particular type of health data describes characteristics of the user or behavior of the user;

wherein the metadata for the data storage area indicates that the data storage area is designated to receive repeated future measurement results for the particular type; and wherein determining the second set of types of health data comprises omitting the particular type of health data from the second set of types of health data based on determining that the metadata for the data storage area indicates that the data storage area is designated to receive repeated future measurement results for the particular type.

8. The computer-implemented method of claim 1, wherein the health application is a software application for a health research study, and wherein the first set of types of health data are types of health data that a study protocol for the health research study specifies to obtain from participants in the health research study as part of the health research study.

9. The computer-implemented method of claim 1, wherein the first set of types of health data and the second set of types of health data each include multiple types of health data, including one or more types of physiological data for the user and one or more types of behavioral data for the user.

10. The computer-implemented method of claim 1, wherein the health application is configured to perform repeated interactions over time to monitor health of the user through (i) sensor measurements performed using sensors of one or more devices, and (ii) survey responses by the user to surveys presented by one or more devices.

11. The computer-implemented method of claim 1, wherein customizing interaction of the health application with the user based on the second set of types of health data comprises:

configuring the health application to initiate collection of data for each of the types of health data in the second set of types of health data.

12. The computer-implemented method of claim 1, wherein customizing interaction of the health application with the user based on the second set of types of health data comprises:

providing, for presentation by the computing device of the user, a list indicating the types of health data in the second set of types of health data as items to be collected for the user.

13. The computer-implemented method of claim 12, wherein the health application is an application for a health research study, and the list is a list of types of health data to be collected in order for the user to enroll in the health research study or as part of the user participating in the health research study.

14. A system comprising:
one or more computing devices that are configured to connect to a communication network; and
one or more computer-readable media storing instructions that are operable, when executed by the one or more computing devices, to cause the one or more computing devices to perform operations comprising:
providing, by the one or more computing devices, access to a health application to a user through a computing device, wherein the health application specifies a first set of types of health data to collect from users of the health application;
receiving, by the one or more computing devices, an identifier for a secured data storage area for the user, the identifier being provided by the user to the health application, wherein the data storage area is managed by a server system configured to (i) provide access to health data in the data storage area in response to an access token for the data storage area, (ii) disallow access to the health data in the data storage area when an access token for the data storage area is not provided, and (iii) provide metadata indicating data classifications for the health data in the data storage area without requiring an access token for the data storage area;
before receiving authorization to access the health data in the data storage area, using, by the one or more computing devices, the identifier to obtain the metadata indicating data classifications for the health data stored in the data storage area, the metadata being obtained from the server system over the communication network;
determining, by the one or more computing devices, a second set of types of health data to collect from the user of the health application, the second set being customized for the user based on the data classifications indicated by the metadata for the data storage area indicated by the identifier provided by the user, wherein the second set of types of health data includes a subset of the types of health data in the first set and omits one or more types of health data in the first set; and
customizing, by the one or more computing devices, interaction of the health application with the user, including generating user interface data used to automatically provide a customized user interface that is customized for the user, wherein the customized user interface is customized to present a subset of content of the health application, wherein the subset of content is selected based on the second set of types of health data determined based on the data classifications indicated by the metadata for the data storage area.

15. The system of claim 14, wherein the operations further comprise:
determining multiple types of health data that the health application is configured to obtain from users of the health application, wherein the determined types of health data are the first set of types of health data; and
for each of the multiple types of health data that the health application is configured to obtain, determining whether the metadata indicates that data of that type of health data is stored in the data storage area;
wherein determining the second set of types of health data comprises:
based on determining that the metadata indicates that data of a particular type of health data is stored in the data storage area, determining the second set of types of health data to omit the particular type of health data; and
wherein customizing interaction of the health application with the user comprises:
based on the determined second set of types of health data, customizing behavior of the health application to (i) use one or more sensors or user interfaces to collect data from the user for each of the types of health data in the second set of types of health data, and (ii) obtain data for the particular type of health data from the data storage area instead of collecting data for the particular type of health data from the user.

16. The system of claim 15, wherein the operations further comprise:
identifying, for the particular type of health data, one or more criteria for data of the particular type of health data to be used by the health application, wherein the one or more criteria specify a constraint for a time constraint, a level of precision, a source of data, or amount of data needed; and
determining, based on the metadata, that the one or more criteria is met for the data of the particular type in the data storage area;
wherein the particular type of health data is omitted from the second set of types of health data based on determining that the one or more criteria for the particular type of is met.

17. The system of claim 15, wherein the operations further comprise:
determining, based on the metadata for the data storage area, that the data storage area stores data of a particular type that is included in the first set of types of health data;
identifying a characteristic or condition that data of the particular type is required to meet to be used by the health application; and
determining, based on the metadata, that the data of the particular type in the data storage area does not have the characteristic or does not satisfy the condition;
wherein determining the second set of types of health data comprises:
based on determining that the data of the particular type in the data storage area does not have the characteristic or does not satisfy the condition, including the particular type of health data in the second set of types of health data such that the health application initiates collection of data of the particular type for the user.

18. The system of claim 14, wherein the health application is a software application for a health research study, and wherein the first set of types of health data are types of health data that a study protocol for the health research study specifies to obtain from participants in the health research study as part of the health research study.

19. The system of claim 14, wherein the first set of types of health data and the second set of types of health data each include multiple types of health data, including one or more types of physiological data for the user and one or more types of behavioral data for the user.

20. One or more non-transitory computer-readable media storing instructions that are operable, when executed by one or more computing devices, to cause the one or more computing devices to perform operations comprising:
providing, by the one or more computing devices, access to a health application to a user through a computing device, wherein the health application specifies a first set of types of health data to collect from users of the health application;
receiving, by the one or more computing devices, an identifier for a secured data storage area for the user, the identifier being provided by the user to the health application, wherein the data storage area is managed by a server system configured to (i) provide access to health data in the data storage area in response to an access token for the data storage area, (ii) disallow access to the health data in the data storage area when an access token for the data storage area is not provided, and (iii) provide metadata indicating data classifications for the health data in the data storage area without requiring an access token for the data storage area; before receiving authorization to access the health data in the data storage area, using, by the one or more computing devices, the identifier to obtain the metadata indicating data classifications for the health data stored in the data storage area, the metadata being obtained from the server system over a communication network;
determining, by the one or more computing devices, a second set of types of health data to collect from the user of the health application, the second set being customized for the user based on the data classifications indicated by the metadata for the data storage area indicated by the identifier provided by the user, wherein the second set of types of health data includes a subset of the types of health data in the first set and omits one or more types of health data in the first set; and
customizing, by the one or more computing devices, interaction of the health application with the user, including generating user interface data used to automatically provide a customized user interface that is customized for the user, wherein the customized user interface is customized to present a subset of content of the health application, wherein the subset of content is selected based on the second set of types of health data determined based on the data classifications indicated by the metadata for the data storage area.

21. The computer-implemented method of claim 1, wherein customizing the interactions of the health application with the user comprises adjusting operation of one or more sensors of the computing device of the user to collect data for the second set of types of health data.

22. The computer-implemented method of claim 1, wherein the health application is an application for a health research study configured to perform health monitoring including data collection for the first set of types of health data; and
wherein customizing the interactions of the health application with the user comprises indicating that participation of the user in the health research study would involve initiating a reduced amount of health monitoring that omits collection of the one or more types of health data collection that are omitted from the second set of types of health data.

23. The computer-implemented method of claim 1, wherein customizing the interactions of the health application with the user comprises:
requesting data from data storage area for the one or more types of health data in the first set that are omitted from the second set; and
configuring the health application to omit initiation of sensor data collection for the one or more types of health data in the first set that are omitted from the second set.

24. The computer-implemented method of claim 1, wherein the health application has a default configuration to perform monitoring to collect data for the types of health data in the first set of types of health data; and
wherein customizing the interactions of the health application with the user comprises performing adjusted monitoring to collect data for the types of health data in the second set of types of health data, such that the health application omits data collection of the one or more types of health data in the first set that are omitted from the second set.

25. The computer-implemented method of claim 1, wherein the content of the health application includes a plurality of interactive elements;
wherein the method comprises determining a subset of the interactive elements that correspond to features of the health application that make use of types of health data that the data classifications indicate to be available in the data storage area; and
wherein generating the user interface data comprises generating the user interface data to cause the customized user interface to (i) include the subset of the interactive elements that correspond to features of the health application that make use of types of health data that the data classifications indicate to be available in the data storage area and (ii) exclude one or more of the interactive elements determined to make use of health data that the data classifications do not indicate to be available in the data storage area.

26. The computer-implemented method of claim 1, comprising providing, by the one or more computing devices, the generated user interface data to the computing device of the user over the communication network.

27. The computer-implemented method of claim 1, comprising presenting, on a display of the computing device of the user, the customized user interface.

* * * * *